(12) United States Patent
Munchhof et al.

(10) Patent No.: US 8,148,401 B2
(45) Date of Patent: Apr. 3, 2012

(54) BENZIMIDAZOLE DERIVATIVES

(75) Inventors: Michael J. Munchhof, Salem, CT (US); Lawrence A. Reiter, Mystic, CT (US); Susan D. La Greca, Old Lyme, CT (US); Christopher S. Jones, Gales Ferry, CT (US); Qifang Li, Stonington, CT (US)

(73) Assignee: Pfizer Inc., New York, NY (US)

( * ) Notice: Subject to any disclaimer, the term of this patent is extended or adjusted under 35 U.S.C. 154(b) by 955 days.

(21) Appl. No.: 12/142,119

(22) Filed: Jun. 19, 2008

(65) Prior Publication Data

US 2009/0005416 A1    Jan. 1, 2009

Related U.S. Application Data

(60) Provisional application No. 61/041,645, filed on Apr. 2, 2008, provisional application No. 60/947,287, filed on Jun. 29, 2007.

(51) Int. Cl.
 A61K 31/454    (2006.01)
 A61K 31/4545   (2006.01)
 C07D 401/04    (2006.01)
 C07D 401/14    (2006.01)

(52) U.S. Cl. .................. 514/322; 546/209

(58) Field of Classification Search .............. None
 See application file for complete search history.

(56) References Cited

U.S. PATENT DOCUMENTS

| | | |
|---|---|---|
| 2004/0152690 A1 | 8/2004 | Balan et al. |
| 2005/0085519 A1 | 4/2005 | Rubin et al. |
| 2005/0197375 A1 | 9/2005 | Sircar et al. |
| 2008/0090870 A1 | 4/2008 | Defossa et al. |

FOREIGN PATENT DOCUMENTS

| | | |
|---|---|---|
| WO | WO03/011219 A2 | 2/2003 |
| WO | WO03/048154 | 6/2003 |
| WO | WO03/082186 A2 | 10/2003 |
| WO | WO2004/035549 A1 | 4/2004 |
| WO | WO2005/042495 A1 | 5/2005 |
| WO | WO2006/050506 | 5/2006 |
| WO | WO2006/099942 A2 | 9/2006 |
| WO | WO2006/124780 A2 | 11/2006 |
| WO | WO2008/075196 A1 | 6/2008 |

OTHER PUBLICATIONS

Golub et al., Science, 286, 531-537, Oct. 1999.*
Li, C. et al., "IFNα Induces Fas Expression and Apoptosis in Hedgehog Pathway Activated BCC Cells Through Inhibiting Ras-Erk Signaling," Oncogene, 2004, 1608-1617, vol. 23, No. 8.

* cited by examiner

*Primary Examiner* — Fiona T Powers
(74) *Attorney, Agent, or Firm* — Raj Advani; Leslie A. Robinson

(57) ABSTRACT

The present invention relates to a compound of the Formula I

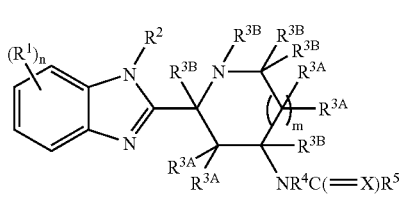

or a pharmaceutically acceptable salt thereof, wherein $R^1$, $R^2$, $R^{3A}$, $R^{3B}$, $R^4$, $R^5$, X, m, and n are as defined herein. Such novel benzamidazole derivatives are useful in the treatment of abnormal cell growth, such as cancer, in mammals. This invention also relates to a method of using such compounds in the treatment of abnormal cell growth in mammals, especially humans, and to pharmaceutical compositions containing such compounds.

17 Claims, No Drawings

BENZIMIDAZOLE DERIVATIVES

This application claims the benefit of U.S. Patent Application Nos. 60/947,287, filed Jun. 29, 2007, and 61/041,645, filed Apr. 2, 2008, both of which are hereby incorporated by reference in their entirety.

FIELD OF INVENTION

This invention relates to novel benzimidazole derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

BACKGROUND

Hedgehog (Hh) proteins are secreted morphogens that are involved in many biological processes during embryonic development. Postnatally, Hh has important roles in tissue homeostasis and aberrant Hh signaling is associated with developmental disorders and several types of cancer. At the cell surface, the Hh signal is thought to be relayed by the 12 transmembrane domain protein Patched (Ptc) (Hooper and Scott, Cell 59: 751-65 (1989); Nakano et al., Nature 341: 508-13 (1989)) and the G-protein-coupled-like receptor Smoothened (Smo) (Alcedo et al., Cell 86: 221-232 (1996); van den Heuvel and Tngham, Nature 382: 547-551 (1996)). Both genetic and biochemical evidence support a receptor model where Ptch and Smo are part of a multi-component receptor complex (Chen and Struhl, Cell 87: 553-63 (1996); Mango et al., Nature 384: 176-9 (1996); Stone et al., Nature 384:129-34 (1996)). Upon binding of Hh to Ptch, the normal inhibitory effect of Ptch on Smo is relieved, allowing Smo to transduce the Hh signal across the plasma membrane. However, the exact mechanism by which Ptch controls Smo activity still has yet to be clarified.

The signaling cascade initiated by Smo results in activation of Gli transcription factors that translocate into the nucleus where they control transcription of target genes. Gli has been shown to influence transcription of Hh pathway inhibitors such as Ptc and Hip I in a negative feedback loop indicating that tight control of the Hh pathway activity is required for proper cellular differentiation and organ formation. Uncontrolled activation of Hh signaling pathway is associated with malignancies in particular those of the brain, skin and muscle as well as angiogenesis. An explanation for this is that the Hh pathway has been shown to regulate cell proliferation in adults by activation of genes involved in cell cycle progression such as cyclin D which is involved in G1-S transition. Also, Sonic Hedgehog (SHh), an ortholog of Hh, blocks cell-cycle arrest mediated by p21, an inhibitor of cyclin dependent kinases. Hh signaling is further implicated in cancer by inducing components in the EGFR pathway (EGF, Her2) involved in proliferation as well as components in the PDGF (PDGFa) and VEGF pathways involved in angiogenesis. Loss of function mutations in the Ptch gene have been identified in patients with the basal cell nevus syndrome (BCNS), a hereditary disease characterized by multiple basal cell carcinomas (BCCs). Dysfunctional Ptch gene mutations have also been associated with a large percentage of sporadic basal cell carcinoma tumors (Chidambaram et al., Cancer Research 56: 4599-601 (1996); Gailani et al., Nature Genet. 14: 78-81 (1996); Hahn et al., Cell 85: 841-51 (1996); Johnson et al., Science 272: 1668-71 (1996); Unden et al., Cancer Res. 56: 4562-5; Wicking et al., Am. J. Hum. Genet. 60: 21-6 (1997)). Loss of Ptch function is thought to cause an uncontrolled Smo signaling in basal cell carcinoma. Similarly, activating Smo mutations have been identified in sporadic BCC tumors (Xie et al., Nature 391: 90-2 (1998)), emphasizing the role of Smo as the signaling subunit in the receptor complex for SHh. Various inhibitors of hedgehog signaling have been investigated such as Cyclopamine, a natural alkaloid that has been shown to arrest cell cycle at G0-GI and to induce apoptosis in SCLC. Cyclopamine is believed to inhibit Smo by binding to its heptahelical bundle. Forskolin has been shown to inhibit the Hh pathway downstream from Smo by activating protein kinase A (PKA) which maintains Gli transcription factors inactive. Despite advances with these and other compounds, there remains a need for potent inhibitors of the hedgehog signaling pathway.

SUMMARY OF THE INVENTION

The present invention relates to a compound of Formula I:

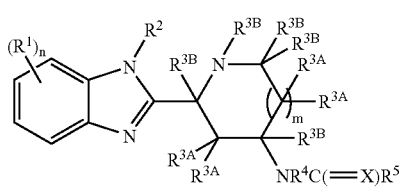

or a pharmaceutically acceptable salt wherein:

each $R^1$ is independently selected from the group consisting of halo, $-(CH_2)_tOH$, $-(CH_2)_tCF_3$, $-(CH_2)_tC\equiv N$, $-NO_2$, $-(CH_2)_tN[(CH_2)_tR^9]_2$, $-(CH_2)_t(C=O)N[(CH_2)_tR^9]_2$, $-(CH_2)_tN[(CH_2)_tR^9](C=O)[(CH_2)_tR^9]$, $-(CH_2)_tN[(CH_2)_tR^9]S(O)_w[(CH_2)_tR^9]$, $-(CH_2)_tS(O)_wN[(CH_2)_tR^9]_2$, $-(CH_2)_tS(O)_w[(CH_2)_tR^9]$, $-(CH_2)_tR^9$, $-(CH_2)_tO[(CH_2)_tR^9]$, $-(CH_2)_t(C=O)[(CH_2)_tR^9]$, $-(CH_2)_t(C=O)O[(CH_2)_tR^9]$, $-(CH_2)_tO(C=O)[(CH_2)_tR^9]$, $-N[(CH_2)_tR^9](C=O)N[(CH_2)_tR^9]_2$, $-(CH_2)_t(C_3-C_{12})$carbocyclyl, $-(CH_2)_t(C_6-C_{10}$ aryl), and $-(CH_2)_t(4$ to 14 membered heterocyclyl) wherein each said $(CH_2)$ moiety may optionally be substituted by one to two substituents independently selected from the group consisting of $-(C_1-C_6)$alkyl, halo, hydroxy, $-(C_1-C_6)$alkoxy, $-CN$, $-(CH_2)_tCF_3$, and $-N[(CH_2)_tR^9]_2$;

$R^2$ is selected from the group consisting of hydrogen, $-(C_1-C_6)$alkyl, $-(CH_2)_qOH$, $-(C=O)O(CH_2)_t(C_6-C_{10}$ aryl), $-(CH_2)_qO(C_1-C_6)$alkyl, $-(CH_2)_qO(C_1-C_6)$alkylOH, $-(CH_2)_pCH_3$, and $-(CH_2)_pCN$;

each $R^{3A}$ is independently selected from the group consisting of hydrogen, $-CN$, halo, hydroxy, $-(C_1-C_6)$alkyl, $-(C_2-C_6)$alkenyl, $-(C_2-C_6)$alkynyl, $-(C_1-C_6)$alkoxy, $-CF_3$, $-OCF_3$, $-N[(CH_2)_tR^9]_2$, $-S(C_1-C_6)$alkyl, $-(S=O)(C_1-C_6)$alkyl, $-S(=O)_2(C_1-C_6)$alkyl, $-(C=O)O(C_1-C_6)$alkyl, $-(C=O)(C_1-C_6)$alkyl, $-(CH_2)_t(C_3-C_{12})$carbocyclyl, $-(CH_2)_t(C_6-C_{10}$ aryl), $-(CH_2)_t(4$ to 14 membered heterocyclyl), $-(CH_2)_tO(CH_2)_t(C_6-C_{10}$ aryl), $-(CH_2)_tO(CH_2)_t(4$ to 14 membered heterocyclyl), $-(CH_2)_t(C=O)(CH_2)_t(C_6-C_{10}$ aryl), $-(CH_2)_t(C=O)(CH_2)_t(4$ to 14 membered heterocyclyl), wherein said heterocyclyl has 1 to 4 ring heteroatoms selected from the group consisting of N, O, and S, and wherein each said alkyl, cycloalkyl, aryl, and heterocyclyl may optionally be substituted by one to three substituents independently selected from the group consisting of halo, hydroxy, $-CN$, $-(C_1-C_6)$alkyl, $-(C_1-C_6)$alkoxy, $-CF_3$, $-OCF_3$, $-N[(CH_2)_tR^9]_2$, $-NO_2$, $-S(C_1-$ C₆)alkyl, —S(=O)(C₁-C₆)alkyl, —S(=O)₂(C₁-C₆)alkyl, —(C=O)O(C₁-C₆)alkyl, —(C=O)(C₁-C₆)alkyl, and —(C₃-C₁₂)carbocyclyl;

each R³ᴮ is selected from the group consisting of hydrogen, —(C₁-C₆)alkyl, —(C₂-C₆)alkenyl, —(C₂-C₆)alkynyl, —CF₃, —(C=O)O(C₁-C₆)alkyl, —(C=O)(C₁-C₆)alkyl, —(CH₂)ₜ(C₃-C₁₂)carbocyclyl, —(CH₂)ₜ(C₆-C₁₀ aryl), —(CH₂)ₜ(4 to 14 membered heterocyclyl), —(CH₂)ₜO(CH₂)ₜ(C₆-C₁₀ aryl), —(CH₂)ₜO(CH₂)ₜ(4 to 14 membered heterocyclyl), —(CH₂)ₜ(C=O)(CH₂)ₜ(C₆-C₁₀ aryl), —(CH₂)ₜ(C=O)(CH₂)ₜ(4 to 14 membered heterocyclyl), wherein said heterocyclyl ring has 1 to 4 ring heteroatoms selected from N, O, or S, and wherein said alkyl, cycloalkyl, aryl, and heterocyclyl may optionally be substituted by one to three substituents independently selected from the group consisting of halo, hydroxy, —CN, —(C₁-C₆)alkyl, —(C₁-C₆)alkoxy, —CF₃, —OCF₃, —N[(CH₂)ₜR⁹]₂, —NO₂, —S(C₁-C₆)alkyl, —(S=O)(C₁-C₆)alkyl, —S(=O)₂(C₁-C₆)alkyl, —(C=O)O(C₁-C₆)alkyl, —(C=O)(C₁-C₆)alkyl, and —(C₃-C₁₂)carbocyclyl;

any R³ᴬ and R³ᴮ or any two R³ᴬ or any two R³ᴮ can be taken together to form an additional carbocyclic ring of from 3 to 9 members thereby forming bridged, fused or spiro cyclic systems, said carbocyclic ring may optionally contain up to 2 double bonds;

R² and R³ᴮ on the nitrogen can be taken together to form an additional heterocyclic ring of from 6 to 9 members thereby forming bridged, fused or spiro cyclic systems, said carbocyclic ring may optionally contain up to 2 double bonds;

R⁴ is selected from the group consisting of hydrogen, —(C₁-C₆)alkyl, —(CH₂)qOH, —(CH₂)qO(C₁-C₆)alkyl, —(CH₂)qO(C₁-C₆)alkylOH, —(CH₂)pCF₃, —(CH₂)pCN, —(CH₂)pNH₂, —(CH₂)pNH(C₁-C₆)alkyl, and —(CH₂)pN[(C₁-C₆)alkyl]₂;

R⁵ is selected from the group consisting of —(C₁-C₆)alkyl, —(C₂-C₆)alkenyl, —(C₂-C₆)alkynyl, —(CH₂)ₜ(C₃-C₁₂)carbocyclyl, —(CH₂)ₜ(C₆-C₁₀)aryl, —(CH₂)p(C₁-C₆)alkoxy, —(CH₂)ₜO(CH₂)ₜ(C₆-C₁₀)aryl, —(CH₂)ₜN[(CH₂)ₜR⁹]₂, —(CH₂)ₜN[(CH₂)ₜR⁹](C₆-C₁₀)aryl, —(CH₂)ₜ(4 to 14 membered heterocyclyl), —(CH₂)ₜO(CH₂)ₜ(4 to 14 membered heterocyclyl) and —(CH₂)ₜ(N[(CH₂)ₜR⁹])(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, and wherein each said (CH₂) moiety, alkyl, alkynyl, alkenyl, carbocyclyl, aryl, and heterocyclyl are independently optionally substituted by 1 to 5 substituents selected from R⁶;

each R⁶ is independently selected from the group consisting of azide, halo, —NO₂, —OR⁷, —(CH₂)ₜ(R⁷), —CF₃, —OCF₃, —OCHF₂, —OCH₂F, —O(CH₂)ₜ(C₆-C₁₀)aryl(R⁷), —(CH₂)ₜC≡N, —(C₁-C₆)alkyl, —(CH₂)ₜ(C₃-C₁₂)carbocyclyl(R⁷), —(CH₂)ₜ(C₆-C₁₀)aryl(R⁷), —(CH₂)ₜ(4 to 14 membered heterocyclyl)(R⁷), —(CH₂)ₜSR⁷, —(CH₂)ₜ(S=O)R⁷, —(CH₂)ₜS(=O)₂R⁷, —[C(R⁶)₂]ₜN(R⁷)S(=O)₂R⁷, —S(=O)₂N(R⁷)₂, —(C=O)R⁷, —(C=O)R⁷, —[C(R⁷)₂]ₜO(C=O)R⁷, —[C(R⁷)₂]ₜO(C=O)N(R⁷)₂, —[C(R⁷)₂]ₜN(R⁷)(C=O)R⁷, —[C(R⁷)₂]ₜN(R⁷)₂, —[C(R⁷)₂]ₜOR⁷, —[C(R⁷)₂]ₜN(R⁷)(C=O)OR⁷, —[C(R⁷)₂]ₜN(R⁷)(C=O)N(R⁷)₂, —[C(R⁷)₂]ₜN(R⁷)S(=O)₂N(R⁷)₂, —[C(R⁷)₂]ₜN(R⁷)N(R⁷)₂, —(C=O)N(R⁷)₂, —O(C=O)N(R⁷)₂, —[C(R⁷)₂]ₜOR⁷, —C(R⁷)₂SR⁷, —[C(R⁷)₂]ₜ(S=O)R⁷, —[C(R⁷)₂]ₜS(=O)₂R⁷, —[C(R⁷)₂]ₜS(=O)₂N(R⁷)₂, —[C(R⁷)₂]ₜN(R⁷)(C=O)R⁷, —[C(R⁷)₂]ₜN(R⁷)(C=O)OR⁷, —C(R⁷)=NN(R⁷)₂, —C(R⁷)=NOR⁷, —C(R⁷)₂N(R⁷)N(R⁷)₂, —[C(R⁷)₂]ₜN(R⁷)S(=O)₂N(R⁷)₂, and —[C(R⁷)₂]ₜN(R⁷)(C=O)N(R⁷)₂;

each R⁷ is independently selected from H, —CF₃, —(C₁-C₆)alkyl, —(C₂-C₆)alkenyl, —(C₂-C₆)alkynyl, —(C₃-C₁₂)carbocyclyl, and —(C₆-C₁₀)aryl, or two R⁷ groups on the same nitrogen atom may be taken together with the nitrogen atom to form a 5 to 8 membered heterocyclyl ring, wherein said heterocyclyl ring has 1 to 3 ring heteroatoms selected from the group consisting of N, O, and S, or two R⁷ groups on the same carbon atom may be taken together with the carbon atom to form a 3 to 7 membered carbocyclyl ring and wherein each said alkyl, alkenyl, aryl, heterocyclyl and carbocyclyl may optionally be substituted by one to three substituents independently selected from the group consisting of halo, hydroxy, —CN, —(C₁-C₆)alkyl, —(C₁-C₆)alkoxy, —CF₃, —OCF₃, —N[(CH₂)ₜR⁹]₂, —NO₂, —S(C₁-C₆)alkyl, —(S=O)(C₁-C₆)alkyl, —S(=O)₂(C₁-C₆)alkyl, —(C=O)O(C₁-C₆)alkyl, —C(=O)(C₁-C₆)alkyl, and —(C₃-C₁₂)carbocyclyl;

X is selected from the group consisting of O, S, and NR⁸;

R⁸ is selected from the group consisting of hydrogen, —(C₁-C₆)alkyl, —(CH₂)ₜC≡N, —NO₂, and —S(=O)₂R⁹;

each R⁹ is independently selected from the group consisting of H, —(C₁-C₆)alkyl, —(CH₂)ₜOH, —(CH₂)ₜ(C₆-C₁₀ aryl), —(CH₂)ₜ(C₃-C₁₂)carbocyclyl, and —(CH₂)ₜ(4 to 14 membered heterocyclyl), wherein said heterocyclyl has 1 to 3 ring heteroatoms selected from the group consisting of N, O, and S, or two R⁹ groups on the same nitrogen atom may be taken together with the nitrogen atom to form a 5 to 8 membered heterocyclyl ring wherein said heterocyclyl ring optionally has 1 to 3 ring additional heteroatoms selected from the group consisting of N, O, and S, or two R⁹ groups on the same carbon atom may be taken together with the carbon atom to form a 3 to 7 membered carbocyclyl ring, wherein each said alkyl, aryl, (CH₂) moiety, carbocyclyl, and heterocyclyl may optionally be substituted by one to three substituents independently selected from the group consisting of —(C₁-C₆)alkyl, halo, hydroxy, —(C₁-C₆)alkoxy, —CN, —(CH₂)ₜCF₃, —(CH₂)ₜ(C₆-C₁₀ aryl), —NH(C₁-C₆)alkyl, —N[(C₁-C₆)alkyl]₂ and —(CH₂)ₜ(4 to 14 membered heterocyclyl) wherein said heterocyclyl has 1 to 3 ring heteroatoms selected from the group consisting of N, O, and S;

each p is an integer independently selected from 1, 2, 3, 4, or 5;

each t is an integer independently selected from 0, 1, 2, 3, 4, or 5;

each m is an integer independently selected from 0, 1 or 2;

each n is an integer independently selected from 0, 1, 2, 3, or 4;

each q is an integer independently selected from 2, 3, 4, or 5; and each w is an integer independently selected from 0, 1, or 2.

In another embodiment is provided a compound of Formula I:

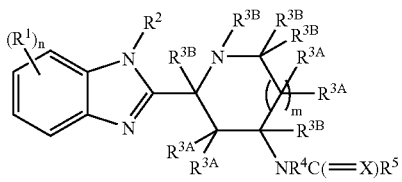

or a pharmaceutically acceptable salt wherein:

each R¹ is independently selected from the group consisting of halo, —(CH₂)ₜOH, —(CH₂)ₜCF₃, —(CH₂)ₜC≡N, —NO₂, —(CH₂)ₜN[(CH₂)ₜR⁹]₂, —(CH₂)ₜ(C=O)N[(CH₂)ₜ

$R^9]_2$, —$(CH_2)_tN[(CH_2)_tR^9](C=O)[(CH_2)_tR^9]$, —$(CH_2)_t[(CH_2)_tR^9]S(O)_w[(CH_2)_tR^9]$, —$(CH_2)_tS(O)_wN[(CH_2)_tR^9]_2$, —$(CH_2)_tS(O)_w[(CH_2)_tR^9]$, —$(CH_2)_tR^9$, —$(CH_2)_tO[(CH_2)_tR^9]$, —$(CH_2)_t(C=O)[(CH_2)_tR^9]$, —$(CH_2)_t(C=O)O[(CH_2)_tR^9]$, —$(CH_2)_tO(C=O)[(CH_2)_tR^9]$, —$N[(CH_2)_tR^9](C=O)N[(CH_2)_tR^9]_2$, —$(CH_2)_t(C_3-C_{12})$carbocyclyl, —$(CH_2)_t(C_6-C_{10})$aryl, and —$(CH_2)_t$(4 to 14 membered heterocyclyl) wherein each said $(CH_2)$ moiety may optionally be substituted by one to two substituents independently selected from the group consisting of —$(C_1-C_6)$alkyl, halo, hydroxy, —$(C_1-C_6)$alkoxy, —CN, —$(CH_2)_tCF_3$, and —$N[(CH_2)_tR^9]_2$;

$R^2$ is selected from the group consisting of hydrogen, —$(C_1-C_6)$alkyl, —$(CH_2)_qOH$, —$(C=O)O(CH_2)_t(C_6-C_{10})$aryl, —$(CH_2)_qO(C_1-C_6)$alkyl, —$(CH_2)_q(C_1-C_6)$alkylOH, —$(CH_2)_pCF_3$, and —$(CH_2)_pCN$;

each $R^{3A}$ is independently selected from the group consisting of hydrogen, —CN, halo, hydroxy, —$(C_1-C_6)$alkyl, —$(C_2-C_6)$alkenyl, —$(C_2-C_6)$alkynyl, —$(C_1-C_6)$alkoxy, —$CF_3$, —$OCF_3$, —$N[(CH_2)_tR^9]_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, —$(CH_2)_t(C_3-C_{12})$carbocyclyl, —$(CH_2)_t(C_6-C_{10})$aryl, —$(CH_2)_t$(4 to 14 membered heterocyclyl), —$(CH_2)_tO(CH_2)_t(C_6-C_{10}$ aryl), —$(CH_2)_tO(CH_2)_t$(4 to 14 membered heterocyclyl), —$(CH_2)_t(C=O)(CH_2)_t(C_6-C_{10}$ aryl), and —$(CH_2)_t(C=O)(CH_2)_t$(4 to 14 membered heterocyclyl), wherein each said heterocyclyl has 1 to 4 ring heteroatoms selected from the group consisting of N, O, and S, and wherein each said alkyl, carbocyclyl, aryl, and heterocyclyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl;

each $R^{3B}$ is independently selected from the group consisting of hydrogen, —$(C_1-C_6)$alkyl, —$(C_2-C_6)$alkenyl, —$(C_2-C_6)$alkynyl, —$CF_3$, —$(C=O)O(C_1-C_6)$alkyl, —$(C=O)(C_1-C_6)$alkyl, —$(CH_2)_t(C_3-C_{12})$carbocyclyl, —$(CH_2)_t(C_6-C_{10})$aryl, —$(CH_2)_t$(4 to 14 membered heterocyclyl), —$(CH_2)_tO(CH_2)_t(C_6-C_{10})$aryl, —$(CH_2)_tO(CH_2)_t$(4 to 14 membered heterocyclyl), —$(CH_2)_t(C=O)(CH_2)_t(C_6-C_{10})$aryl, and —$(CH_2)_t(C=O)(CH_2)_t$(4 to 14 membered heterocyclyl), wherein each said heterocyclyl ring has 1 to 4 ring heteroatoms selected from N, O, and S, and wherein each said alkyl, carbocyclyl, aryl, and heterocyclyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl; or any $R^{3A}$ and $R^{3B}$ or any two $R^{3A}$ or any two $R^{3B}$ can be taken together to form an additional carbocyclic ring of from 3 to 9 members thereby forming bridged, fused or spiro cyclic system, said carbocyclic ring may optionally contain up to 2 double bonds; or $R^2$ and $R^{3B}$ on the nitrogen can be taken together to form an additional heterocyclic ring of from 6 to 9 members thereby forming bridged, fused or spiro cyclic system, said heterocyclic ring may optionally contain up to 2 double bonds;

$R^4$ is selected from the group consisting of hydrogen, —$(C_1-C_6)$alkyl, —$(CH_2)_qOH$, —$(CH_2)_qO(C_1-C_6)$alkyl, —$(CH_2)_qO(C_1-C_6)$alkylOH, —$(CH_2)_pCF_3$, —$(CH_2)_pCN$, —$(CH_2)_pNH_2$, —$(CH_2)_pNH(C_1-C_6)$alkyl, and —$(CH_2)_pN[(C_1-C_6)$alkyl$]_2$;

$R^5$ is selected from the group consisting of —$(C_1-C_6)$alkyl, —$(C_2-C_6)$alkenyl, —$(C_2-C_6)$alkynyl, —$(CH_2)_t(C_3-C_{12})$carbocyclyl, —$(CH_2)_t(C_6-C_{10})$aryl, —$(CH_2)_p(C_1-C_6)$alkoxy, —$(CH_2)_tO(CH_2)_t(C_6-C_{10})$aryl, —$(CH_2)_tN[(CH_2)_tR^9]_2$, —$(CH_2)_tN[(CH_2)_tR^9](C_6-C_{10})$aryl, —$(CH_2)_t$(4 to 14 membered heterocyclyl), —$(CH_2)_tO$(4 to 14 membered heterocyclyl) and —$(CH_2)_t(N[(CH_2)_tR^9])$(4 to 14 membered heterocyclyl), wherein each said heterocyclyl has 1 to 3 ring heteroatoms selected from the group consisting of N, O, and S, and wherein one or two carbon atoms of said heterocyclyl are optionally substituted with an oxo group, and wherein each said $(CH_2)$ moiety, alkyl, alkynyl, alkenyl, carbocyclyl, aryl, and heterocyclyl are independently optionally substituted by 1 to 5 substituents selected from $R^6$;

each $R^6$ is independently selected from the group consisting of azide, halo, —$NO_2$, —$OR^7$, —$(CH_2)_t(R^7)$, —$CF_3$, —$OCF_3$, —$OCHF_2$, —$OCH_2F$, —$O(CH_2)_t(C_6-C_{10})$aryl$(R^7)$, —$(CH_2)_tC\equiv N$, —$(C_1-C_6)$alkyl, —$(CH_2)_t(C_3-C_{12})$carbocyclyl$(R^7)$, —$(CH_2)_t(C_6-C_{10})$aryl$(R^7)$, —$(CH_2)_t$(4 to 14 membered heterocyclyl)$(R^7)$, —$(CH_2)_tSR^7$, —$(CH_2)_t(S=O)R^7$, —$(CH_2)_tS(=O)_2R^7$, —$[C(R^7)_2]_tN(R^7)S(=O)_2R^7$, —$S(=O)_2N(R^7)_2$, —$(C=O)R^7$, —$(C=O)OR^7$, —$[C(R^7)_2]_tO(C=O)R^7$, —$[C(R^7)_2]_tO(C=O)N(R^7)_2$, —$[C(R^7)_2]_tN(R^7)(C=O)R^7$, —$[C(R^7)_2]_tN(R^7)_2$, —$[C(R^7)_2]_tOR^7$, —$[C(R^7)_2]_tN(R^7)(C=O)OR^7$, —$[C(R^7)_2]_tN(R^7)(C=O)N(R^7)_2$, —$[C(R^7)_2]_tN(R^7)S(=O)_2N(R^7)_2$, —$[C(R^7)_2]_tN(R^7)N(R^7)_2$, —$(C=O)N(R^7)_2$, —$O(C=O)N(R^7)_2$, —$[C(R^7)_2]_tOR^7$, —$C(R^7)_2SR^7$, —$[C(R^7)_2]_t(S=O)R^7$, —$[C(R^7)_2]_tS(=O)_2R^7$, —$[C(R^7)_2]_tS(=O)_2N(R^7)_2$, —$[C(R^7)_2]_tN(R^7)(C=O)R^7$, —$[C(R^7)_2]_tN(R^7)(C=O)OR^7$, —$C(R^7)=NN(R^7)_2$, —$C(R^7)=NOR^7$, —$C(R^7)_2N(R^7)N(R^7)_2$, —$[C(R^7)_2]_tN(R^7)S(=O)_2N(R^7)_2$, and —$[C(R^7)_2]_tN(R^7)(C=O)N(R^7)_2$, each $R^7$ is independently selected from H, —$CF_3$, —$(C_1-C_6)$alkyl, —$(C_2-C_6)$alkenyl, —$(C_2-C_6)$alkynyl, —$(C_3-C_{12})$carbocyclyl, and —$(C_6-C_{10})$aryl, or two $R^7$ groups on the same nitrogen atom may be taken together with the nitrogen atom to form a 5 to 8 membered heterocyclyl ring, wherein said heterocyclyl ring has 1 to 3 ring heteroatoms selected from the group consisting of N, O, and S, or two $R^7$ groups on the same carbon atom may be taken together with the carbon atom to form a 3 to 7 membered carbocyclyl ring and wherein each said alkyl, alkenyl, aryl, heterocyclyl and carbocyclyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$C(=O)(C_1-C_6)$alkyl, and —$(C_3-C_{12})$carbocyclyl;

X is selected from the group consisting of O, S, and $NR^8$;

$R^8$ is selected from the group consisting of hydrogen, —$(C_1-C_6)$alkyl, —$(CH_2)_tC\equiv N$, —$NO_2$, and —$S(=O)_2R^9$;

each $R^9$ is independently selected from the group consisting of hydrogen, —$(C_1-C_6)$alkyl, —$(CH_2)_tOH$, —$(CH_2)_t(C_6-C_{10})$aryl, —$(CH_2)_t(C_3-C_{12})$carbocyclyl, and —$(CH_2)_t$(4 to 14 membered heterocyclyl), wherein said heterocyclyl has 1 to 3 ring heteroatoms selected from the group consisting of N, O, and S, or two $R^9$ groups on the same nitrogen atom may be taken together with the nitrogen atom to form a 5 to 8 membered heterocyclyl ring wherein said heterocyclyl ring optionally has 1 to 3 ring additional heteroatoms selected from the group consisting of N, O, and S, or two $R^9$ groups on the same carbon atom may be taken together with the carbon atom to form a 3 to 7 membered carbocyclyl ring, wherein each said alkyl, aryl, $(CH_2)$ moiety, carbocyclyl, and heterocyclyl may optionally be substituted by one to three substituents independently selected from the group consisting of —($C_1$-$C_6$)alkyl, halo, hydroxy, —($C_1$-$C_6$)alkoxy, —CN, —($CH_2$)$_t$$CF_3$, —($CH_2$)$_t$($C_6$-$C_{10}$)aryl, —NH($C_1$-$C_6$)alkyl, —N[($C_1$-$C_6$)alkyl]$_2$ and —($CH_2$)$_t$(4 to 14 membered heterocyclyl) wherein said heterocyclyl has 1 to 3 ring heteroatoms selected from the group consisting of N, O, and S;

each p is independently 1, 2, 3, 4, or 5;
each t is independently 0, 1, 2, 3, 4, or 5;
each m is independently 0, 1 or 2;
each n is independently 0, 1, 2, 3, or 4;
each q is independently 2, 3, 4, or 5; and
each w is independently 0, 1, or 2;

provided that the compound of Formula I is not 2-amino-N-[(3R,5S)-5-[5-(phenylmethyl)-1H-benzimidazol-2-yl]-3-pyrrolidinyl]-acetamide.

In still another embodiment is provided a compound of Formula I:

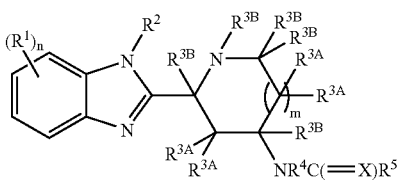

1 or a pharmaceutically acceptable salt wherein:

each $R^1$ is independently selected from the group consisting of halo, —($CH_2$)$_t$OH, —($CH_2$)$_t$$CF_3$, —($CH_2$)$_t$C≡N, —$NO_2$, —($CH_2$)$_t$N[($CH_2$)$_t$$R^9$]$_2$, —($CH_2$)$_t$(C═O)N[($CH_2$)$_t$$R^9$]$_2$, —($CH_2$)$_t$N[($CH_2$)$_t$$R^9$](C═O)[($CH_2$)$_t$$R^9$], —($CH_2$)$_t$N[($CH_2$)$_t$$R^9$]S(O)$_w$[($CH_2$)$_t$$R^9$], —($CH_2$)$_t$S(O)$_w$N[($CH_2$)$_t$$R^9$]$_2$, —($CH_2$)$_t$S(O)$_w$[($CH_2$)$_t$$R^9$], —($CH_2$)$_t$$R^9$, —($CH_2$)$_t$O[($CH_2$)$_t$$R^9$], —($CH_2$)$_t$(C═O)[($CH_2$)$_t$$R^9$], —($CH_2$)$_t$(C═O)O[($CH_2$)$_t$$R^9$], —($CH_2$)$_t$O(C═O)[($CH_2$)$_t$$R^9$], —N[($CH_2$)$_t$$R^9$](C═O)N[($CH_2$)$_t$$R^9$]$_2$, —($CH_2$)$_t$($C_3$-$C_{12}$)carbocyclyl, —($CH_2$)$_t$($C_6$-$C_{10}$)aryl, and —($CH_2$)$_t$(4 to 14 membered heterocyclyl) wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —($CH_2$)$_t$$CF_3$, and —N[($CH_2$)$_t$$R^9$]$_2$;

$R^2$ is selected from the group consisting of hydrogen, —($C_1$-$C_6$)alkyl, —($CH_2$)$_q$OH, —(C═O)O($CH_2$)$_t$($C_6$-$C_{10}$) aryl, —($CH_2$)$_q$O($C_1$-$C_6$)alkyl, —($CH_2$)$_q$O($C_1$-$C_6$)alkylOH, —($CH_2$)$_p$$CF_3$, and —($CH_2$)$_p$CN;

each $R^{3A}$ is independently selected from the group consisting of hydrogen, —CN, halo, hydroxy, —($C_1$-$C_6$)alkyl, —($C_2$-$C_6$)alkenyl, —($C_2$-$C_6$)alkynyl, —($C_1$-$C_6$)alkoxy, —$CF_3$, —$OCF_3$, —N[($CH_2$)$_t$$R^9$]$_2$, —S($C_1$-$C_6$)alkyl, —(S═O)($C_1$-$C_6$)alkyl, —S(═O)$_2$($C_1$-$C_6$)alkyl, —(C═O)O($C_1$-$C_6$)alkyl, —(C═O)($C_1$-$C_6$)alkyl, —($CH_2$)$_t$($C_3$-$C_{12}$)carbocyclyl, —($CH_2$)$_t$($C_6$-$C_{10}$)aryl, —($CH_2$)$_t$(4 to 14 membered heterocyclyl), —($CH_2$)$_t$O($CH_2$)$_t$($C_6$-$C_{10}$ aryl), —($CH_2$)$_t$O($CH_2$)$_t$(4 to 14 membered heterocyclyl), —($CH_2$)$_t$(C═O)($CH_2$)$_t$($C_6$-$C_{10}$ aryl), and —($CH_2$)$_t$(C═O)($CH_2$)$_t$(4 to 14 membered heterocyclyl), wherein each said heterocyclyl has 1 to 4 ring heteroatoms selected from the group consisting of N, O, and S, and wherein each said alkyl, carbocyclyl, aryl, and heterocyclyl may optionally be substituted by one to three substituents independently selected from the group consisting of halo, hydroxy, —CN, —($C_1$-$C_6$)alkyl, —($C_1$-$C_6$)alkoxy, —$CF_3$, —$OCF_3$, —N[($CH_2$)$_t$$R^9$]$_2$, —$NO_2$, —S($C_1$-$C_6$)alkyl, —(S═O)($C_1$-$C_6$)alkyl, —S(═O)$_2$($C_1$-$C_6$) alkyl, —(C═O)O($C_1$-$C_6$)alkyl, —(C═O)($C_1$-$C_6$)alkyl, and —($C_3$-$C_{12}$)carbocyclyl;

each $R^{3B}$ is independently selected from the group consisting of hydrogen, —($C_1$-$C_6$)alkyl, —($C_2$-$C_6$)alkenyl, —($C_2$-$C_6$)alkynyl, —$CF_3$, —(C═O)O($C_1$-$C_6$)alkyl, —(C═O)($C_1$-$C_6$)alkyl, —($CH_2$)$_t$($C_3$-$C_{12}$)carbocyclyl, —($CH_2$)$_t$($C_6$-$C_{10}$) aryl, —($CH_2$)$_t$(4 to 14 membered heterocyclyl), —($CH_2$)$_t$O ($CH_2$)$_t$($C_6$-$C_{10}$)aryl, —($CH_2$)$_t$O($CH_2$)$_t$(4 to 14 membered heterocyclyl), —($CH_2$)$_t$(C═O)($CH_2$)$_t$($C_6$-$C_{10}$)aryl, and —($CH_2$)$_t$(C═O)($CH_2$)$_t$(4 to 14 membered heterocyclyl), wherein each said heterocyclyl ring has 1 to 4 ring heteroatoms selected from N, O, and S, and wherein each said alkyl, carbocyclyl, aryl, and heterocyclyl may optionally be substituted by one to three substituents independently selected from the group consisting of halo, hydroxy, —CN, —($C_1$-$C_6$)alkyl, —($C_1$-$C_6$)alkoxy, —$CF_3$, —$OCF_3$, —N[($CH_2$)$_t$$R^9$]$_2$, —$NO_2$, —S($C_1$-$C_6$)alkyl, —(S═O)($C_1$-$C_6$)alkyl, —S(═O)$_2$($C_1$-$C_6$) alkyl, —(C═O)O($C_1$-$C_6$)alkyl, —(C═O)($C_1$-$C_6$)alkyl, and —($C_3$-$C_{12}$)carbocyclyl; or any $R^{3A}$ and $R^{3B}$ or any two $R^{3A}$ or any two $R^{3B}$ can be taken together to form an additional carbocyclic ring of from 3 to 9 members thereby forming bridged, fused or spiro cyclic system, said carbocyclic ring may optionally contain up to 2 double bonds; or $R^2$ and $R^{3B}$ on the nitrogen can be taken together to form an additional heterocyclic ring of from 6 to 9 members thereby forming bridged, fused or spiro cyclic system, said heterocyclic ring may optionally contain up to 2 double bonds;

$R^4$ is selected from the group consisting of hydrogen, —($C_1$-$C_6$)alkyl, —($CH_2$)$_q$OH, —($CH_2$)$_q$O($C_1$-$C_6$)alkyl, —($CH_2$)$_q$O($C_1$-$C_6$)alkylOH, —($CH_2$)$_p$$CF_3$, —($CH_2$)$_p$CN, —($CH_2$)$_p$$NH_2$, —($CH_2$)$_p$NH($C_1$-$C_6$)alkyl, and —($CH_2$)$_p$N [($C_1$-$C_6$)alkyl]$_2$;

$R^5$ is selected from the group consisting of —($C_1$-$C_6$)alkyl, —($C_2$-$C_6$)alkenyl, —($C_2$-$C_6$)alkynyl, —($CH_2$)$_t$($C_3$-$C_{12}$)carbocyclyl, —($CH_2$)$_t$($C_6$-$C_{10}$)aryl, —($CH_2$)$_p$($C_1$-$C_6$)alkoxy, —($CH_2$)$_t$O($CH_2$)$_t$($C_6$-$C_{10}$)aryl, —($CH_2$)$_t$N[($CH_2$)$_t$$R^9$]$_2$, —($CH_2$)$_t$N[($CH_2$)$_t$$R^9$]($C_6$-$C_{10}$)aryl, —($CH_2$)$_t$(4 to 14 membered heterocyclyl), —($CH_2$)$_t$O($CH_2$)$_t$(4 to 14 membered heterocyclyl) and —($CH_2$)$_t$(N[($CH_2$)$_t$$R^9$])(4 to 14 membered heterocyclyl), wherein each said heterocyclyl has 1 to 3 ring heteroatoms selected from the group consisting of N, O, and S, and wherein one or two carbon atoms of said heterocyclyl are optionally substituted with an oxo group, and wherein each said ($CH_2$) moiety, alkyl, alkynyl, alkenyl, carbocyclyl, aryl, and heterocyclyl are independently optionally substituted by 1 to 5 substituents selected from $R^6$;

each $R^6$ is independently selected from the group consisting of azide, halo, —$NO_2$, —$OR^7$, —($CH_2$)$_t$($R^7$), —$CF_3$, —$OCF_3$, —$OCHF_2$, —$OCH_2$F, —O($CH_2$)$_t$($C_6$-$C_{10}$)aryl($R^7$), —($CH_2$)$_t$C≡N, —($C_1$-$C_6$)alkyl, —($CH_2$)$_t$($C_3$-$C_{12}$)carbocyclyl($R^7$), —($CH_2$)$_t$($C_6$-$C_{10}$)aryl($R^7$), —($CH_2$)$_t$(4 to 14 membered heterocyclyl)($R^7$), —($CH_2$)$_t$$SR^7$, —($CH_2$)$_t$(S═O)$R^7$, —($CH_2$)$_t$S(═O)$_2$$R^7$, —[C($R^7$)$_2$]$_t$N($R^7$)S(═O)$_2$$R^7$, —S(═O)$_2$N($R^7$)$_2$, —(C═O)$R^7$, —(C═O)$OR^7$, —[C($R^7$)$_2$]$_t$O(C═O)$R^7$, —[C($R^7$)$_2$]$_t$O(C═O)N($R^7$)$_2$, —[C($R^7$)$_2$]$_t$N ($R^7$)(C═O)$R^7$, —[C($R^7$)$_2$]$_t$N($R^7$)$_2$, —[C($R^7$)$_2$]$_t$$OR^7$, —[C($R^7$)$_2$]$_t$N($R^7$)(C═O)$OR^7$, —[C($R^7$)$_2$]$_t$N($R^7$)(C═O)N($R^7$)$_2$, —[C($R^7$)$_2$]$_t$N($R^7$)S(═O)$_2$N($R^7$)$_2$, —[C($R^7$)$_2$]$_t$N($R^7$)N($R^7$)$_2$, —(C═O)N($R^7$)$_2$, —O(C═O)N($R^7$)$_2$, —[C($R^7$)$_2$]$_t$$OR^7$, —C($R^7$)$_2$$SR^7$, —[C($R^7$)$_2$]$_t$(S═O)$R^7$, —[C($R^7$)$_2$]$_t$S(═O)$_2$$R^7$, —[C($R^7$)$_2$]$_t$S(═O)$_2$N($R^7$)$_2$, —[C($R^7$)$_2$]$_t$N($R^7$)(C═O) $R^7$, —[C($R^7$)$_2$]$_t$N($R^7$)(C═O)$OR^7$, —C($R^7$)═NN($R^7$)$_2$, —C($R^7$)═$NOR^7$, —C($R^7$)$_2$N($R^7$)N($R^7$)$_2$, —[C($R^7$)$_2$]$_t$N($R^7$) S(═O)$_2$N($R^7$)$_2$, and —[C($R^7$)$_2$]$_t$N($R^7$)(C═O)N($R^7$)$_2$;

each $R^7$ is independently selected from H, —$CF_3$, —($C_1$-$C_6$)alkyl, —($C_2$-$C_6$)alkenyl, —($C_2$-$C_6$)alkynyl, —($C_3$-$C_{12}$) carbocyclyl, and —($C_6$-$C_{10}$)aryl, or two $R^7$ groups on the same nitrogen atom may be taken together with the nitrogen atom to form a 5 to 8 membered heterocyclyl ring, wherein said heterocyclyl ring has 1 to 3 ring heteroatoms selected from the group consisting of N, O, and S, or two $R^7$ groups on the same carbon atom may be taken together with the carbon atom to form a 3 to 7 membered carbocyclyl ring and wherein each said alkyl, alkenyl, aryl, heterocyclyl and carbocyclyl may optionally be substituted by one to three substituents independently selected from the group consisting of halo, hydroxy, —CN, —($C_1$-$C_6$)alkyl, —($C_1$-$C_6$)alkoxy, —$CF_3$, —$OCF_3$, —$N[(CH_2)_tR^9]_2$, —$NO_2$, —$S(C_1$-$C_6)$alkyl, —$S(=O)(C_1$-$C_6)$alkyl, —$S(=O)_2(C_1$-$C_6)$alkyl, —(C=O)O($C_1$-$C_6$)alkyl, —C(=O)($C_1$-$C_6$)alkyl, and —($C_3$-$C_{12}$)carbocyclyl;

X is selected from the group consisting of O, S, and $NR^8$;

$R^8$ is selected from the group consisting of hydrogen, —($C_1$-$C_6$)alkyl, —$(CH_2)_tC\equiv N$, —$NO_2$, and —$S(=O)_2R^9$;

each $R^9$ is independently selected from the group consisting of hydrogen, —($C_1$-$C_6$)alkyl, —$(CH_2)_tOH$, —$(CH_2)_t(C_6$-$C_{10})$aryl, —$(CH_2)_t(C_3$-$C_{12})$carbocyclyl, and —$(CH_2)_t$(4 to 14 membered heterocyclyl), wherein said heterocyclyl has 1 to 3 ring heteroatoms selected from the group consisting of N, O, and S, or two $R^9$ groups on the same nitrogen atom may be taken together with the nitrogen atom to form a 5 to 8 membered heterocyclyl ring wherein said heterocyclyl ring optionally has 1 to 3 ring additional heteroatoms selected from the group consisting of N, O, and S, or two $R^9$ groups on the same carbon atom may be taken together with the carbon atom to form a 3 to 7 membered carbocyclyl ring, wherein each said alkyl, aryl, ($CH_2$) moiety, carbocyclyl, and heterocyclyl may optionally be substituted by one to three substituents independently selected from the group consisting of —($C_1$-$C_6$)alkyl, halo, hydroxy, —($C_1$-$C_6$)alkoxy, —CN, —$(CH_2)_tCF_3$, —$(CH_2)_t(C_6$-$C_{10})$aryl, —$NH(C_1$-$C_6)$alkyl, —$N[(C_1$-$C_6)$alkyl$]_2$ and —$(CH_2)_t$(4 to 14 membered heterocyclyl) wherein said heterocyclyl has 1 to 3 ring heteroatoms selected from the group consisting of N, O, and S;

each p is independently 1, 2, 3, 4, or 5;
each t is independently 0, 1, 2, 3, 4, or 5;
each m is independently 1 or 2;
each n is independently 0, 1, 2, 3, or 4;
each q is independently 2, 3, 4, or 5; and
each w is independently 0, 1, or 2.

In one embodiment the invention relates to a compound of Formula I or a pharmaceutically acceptable salt thereof wherein the 4 position has absolute configuration R.

In one embodiment the invention relates to a compound of Formula I or a pharmaceutically acceptable salt thereof wherein the 4 position has absolute configuration R and the 2 position has absolute configuration R.

In one embodiment the invention relates to a compound of Formula I or a pharmaceutically acceptable salt thereof wherein each $R^1$ is independently selected from the group consisting of halo, —$(CH_2)_tOH$, —$(CH_2)_tCF_3$, —$(CH_2)_tC\equiv N$, —$NO_2$, —$(CH_2)_tN[(CH_2)_tR^9]_2$, —$(CH_2)_t(C=O)N[(CH_2)_tR^9]_2$, —$(CH_2)_tN[(CH_2)_tR^9](C=O)[(CH_2)_tR^9]$, —$(CH_2)_tR^9$, —$(CH_2)_tO[(CH_2)_tR^9]$, —$(CH_2)_t(C=O)[(CH_2)_tR^9]$, —$(CH_2)_t(C=O)O[(CH_2)_tR^9]$, —$(CH_2)_t(C_3$-$C_{12})$carbocyclyl, —$(CH_2)_t(C_6$-$C_{10}$ aryl), and —$(CH_2)_t$(4 to 14 membered heterocyclyl) wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In another embodiment the invention relates to a compound of Formula I or a pharmaceutically acceptable salt thereof wherein each $R^1$ is independently selected from the group consisting of halo, —$(CH_2)_tOH$, —$(CH_2)_tCF_3$, —$(CH_2)_tC\equiv N$, —$NO_2$, —$(CH_2)_tN[(CH_2)_tR^9]_2$, —$(CH_2)_t(C=O)N[(CH_2)_tR^9]_2$, —$(CH_2)_tN[(CH_2)_tR^9](C=O)[(CH_2)_tR^9]$, —$(CH_2)_tR^9$, —$(CH_2)_tO[(CH_2)_tR^9]$, —$(CH_2)_t(C=O)[(CH_2)_tR^9]$, and —$(CH_2)_t(C=O)O[(CH_2)_tR^9]$, wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In another embodiment the invention relates to a compound of Formula I or a pharmaceutically acceptable salt thereof wherein each $R^1$ is independently selected from the group consisting of halo, —$(CH_2)_tCF_3$, —$(CH_2)_tC\equiv N$, —$(CH_2)_tN[(CH_2)_tR^9]_2$, —$(CH_2)_tR^9$, and —$(CH_2)_tO[(CH_2)_tR^9]$ wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In another embodiment the invention relates to a compound of Formula I or a pharmaceutically acceptable salt thereof wherein each $R^1$ is halo.

In another embodiment the invention relates to a compound of Formula I or a pharmaceutically acceptable salt thereof wherein each $R^1$ is —$(CH_2)_tCF_3$, wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In another embodiment the invention relates to a compound of Formula I or a pharmaceutically acceptable salt thereof wherein each $R^1$ is —$(CH_2)_tC\equiv N$, wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In one embodiment the invention relates to a compound of Formula I or a pharmaceutically acceptable salt thereof wherein each $R^1$ is —$(CH_2)_tN[(CH_2)_tR^9]_2$, wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In one embodiment the invention relates to a compound of Formula I or a pharmaceutically acceptable salt thereof wherein each $R^1$ is —$(CH_2)_tR^9$, wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In one embodiment the invention relates to a compound of Formula I or a pharmaceutically acceptable salt thereof wherein each $R^1$ is —$(CH_2)_tO[(CH_2)_tR^9]$, wherein each said ($CH_2$) moiety may optionally be substituted by one to two substituents independently selected from the group consisting of —($C_1$-$C_6$)alkyl, halo, hydroxy, —($C_1$-$C_6$)alkoxy, —CN, —$(CH_2)_tCF_3$, and —$N[(CH_2)_tR^9]_2$.

In another embodiment the invention relates to a compound of Formula I or a pharmaceutically acceptable salt thereof wherein $R^2$ is selected from the group consisting of hydrogen, —($C_1$-$C_6$)alkyl, —$(CH_2)_qOH$, —(C=O)O($CH_2$)$_t$($C_6$-$C_{10}$ aryl), —$(CH_2)_qO(C_1$-$C_6)$alkyl, —$(CH_2)_qO(C_1$-$C_6)$alkylOH, —$(CH_2)_pCF_3$, and —$(CH_2)_pCN$.

In one embodiment the invention relates to a compound of Formula I or a pharmaceutically acceptable salt thereof wherein $R^2$ is selected from the group consisting of hydrogen, —($C_1$-$C_6$)alkyl, —$(CH_2)_qOH$, —$(CH_2)_pCF_3$, and —$(CH_2)_p$CN.

In one embodiment the invention relates to a compound of Formula I or a pharmaceutically acceptable salt thereof wherein $R^2$ is hydrogen.

In one embodiment the invention relates to a compound of Formula I or a pharmaceutically acceptable salt thereof wherein $R^2$ is —$(C_1-C_6)$alkyl.

In one embodiment the invention relates to a compound of Formula I or a pharmaceutically acceptable salt thereof wherein each $R^{3A}$ is independently selected from the group consisting of hydrogen, —CN, halo, hydroxy, —$(C_1-C_6)$alkyl, —$(C_2-C_6)$alkenyl, —$(C_2-C_6)$alkynyl, —$(C_1-C_6)$alkoxy, —$CF_3$, —$OCF_3$, —$N[(CH_2)_tR^9]_2$, —$S(C_1-C_6)$alkyl, —$S(=O)(C_1-C_6)$alkyl, —$S(=O)_2(C_1-C_6)$alkyl, —$(C=O)O(C_1-C_6)$alkyl, —$(C=O)(C_1-C_6)$alkyl, —$(CH_2)_t(C_3-C_{12})$carbocyclyl, —$(CH_2)_t(C_6-C_{10}$ aryl), —$(CH_2)_tO(CH_2)_t(C_6-C_{10}$ aryl), —$(CH_2)_t(C=O)(CH_2)_t(C_6-C_{10}$ aryl), wherein each said alkyl, cycloalkyl, aryl, and heterocyclyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$S(=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3A}$ is independently selected from the group consisting of hydrogen, —CN, halo, hydroxy, —$(C_1-C_6)$alkyl, —$(C_2-C_6)$alkenyl, —$(C_2-C_6)$alkynyl, —$(C_1-C_6)$alkoxy, —$CF_3$, —$OCF_3$, —$N[(CH_2)_tR^9]_2$, —$(CH_2)_t(C_3-C_{12})$carbocyclyl, —$(CH_2)_t(C_6-C_{10}$ aryl), —$(CH_2)_tO(CH_2)_t(C_6-C_{10}$ aryl), —$(CH_2)_t(C=O)(CH_2)_t(C_6-C_{10}$ aryl), wherein each said alkyl, cycloalkyl, and aryl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$S(=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3A}$ is independently selected from the group consisting of hydrogen and —$(C_1-C_6)$alkyl, wherein each said alkyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$S(=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3B}$ is independently selected from the group consisting of hydrogen, —CN, halo, hydroxy, —$(C_1-C_6)$alkyl, —$(C_2-C_6)$alkenyl, —$(C_2-C_6)$alkynyl, —$(C_1-C_6)$alkoxy, —$CF_3$, —$OCF_3$, —$(C=O)O(C_1-C_6)$alkyl, —$(C=O)(C_1-C_6)$alkyl, —$(CH_2)_t(C_3-C_{12})$carbocyclyl, —$(CH_2)_t(C_6-C_{10}$ aryl), and —$(CH_2)_t$(4 to 14 membered heterocyclyl), wherein said heterocyclyl has 1 to 4 ring heteroatoms selected from the group consisting of N, O, and S, and wherein each said alkyl, cycloalkyl, aryl, and heterocyclyl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$S(=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3B}$ is independently selected from the group consisting of hydrogen, —CN, halo, hydroxy, —$(C_1-C_6)$alkyl, —$CF_3$, —$OCF_3$, —$(C=O)O(C_1-C_6)$alkyl, —$(C=O)(C_1-C_6)$alkyl, —$(CH_2)_t(C_3-C_{12})$carbocyclyl, and —$(CH_2)_t(C_6-C_{10}$ aryl), wherein each said alkyl, cycloalkyl, and aryl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3B}$ is independently selected from the group consisting of hydrogen, —$(C_1-C_6)$alkyl, —$(C=O)O(C_1-C_6)$alkyl, —$(CH_2)_t(C_3-C_{12})$carbocyclyl, —$(CH_2)_t(C_6-C_{10}$ aryl), wherein each said alkyl, cycloalkyl, and aryl, may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3B}$ is hydrogen.

In one embodiment the invention relates to a compound of Formula I or a pharmaceutically acceptable salt thereof wherein each $R^{3B}$ is independently selected from the group consisting of —$(C_1-C_6)$alkyl, wherein said alkyl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3B}$ is independently selected from the group consisting of —$(C=O)O(C_1-C_6)$alkyl, wherein said alkyl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3B}$ is independently selected from the group consisting of —$(CH_2)_t(C_3-C_{12})$carbocyclyl, wherein said carbocyclyl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein each $R^{3B}$ is independently selected from the group consisting of —$(CH_2)_t(C_6-C_{10}$ aryl), wherein said aryl may optionally be substituted by one to three substituents independently selected from the group consisting of halo, hydroxy, —CN, —($C_1$-$C_6$)alkyl, —($C_6$-$C_{10}$)aryl, —($C_1$-$C_6$)alkoxy, —$CF_3$, —$OCF_3$, —$N[(CH_2)_rR^9]_2$, —$NO_2$, —$S(C_1$-$C_6)$alkyl, —$(S=O)(C_1$-$C_6)$alkyl, —$S(=O)_2(C_1$-$C_6)$alkyl, —(C=O)O($C_1$-$C_6$)alkyl, —(C=O)($C_1$-$C_6$)alkyl, and —($C_3$-$C_{12}$)carbocyclyl.

In one embodiment the invention relates to a compound of Formula I or a pharmaceutically acceptable salt thereof wherein $R^4$ is selected from the group consisting of hydrogen and —($C_1$-$C_6$)alkyl.

In an embodiment the invention relates to a compound of Formula I or a pharmaceutically acceptable salt thereof wherein $R^4$ is hydrogen.

In one embodiment the invention relates to a compound of Formula I or a pharmaceutically acceptable salt thereof wherein $R^4$ is —($C_1$-$C_6$)alkyl.

In one embodiment the invention relates to a compound of Formula I or a pharmaceutically acceptable salt thereof wherein $R^5$ is selected from the group consisting of —$(CH_2)_t$($C_3$-$C_{12}$)carbocyclyl, —$(CH_2)_t$($C_6$-$C_{10}$)aryl, —$(CH_2)_p$($C_1$-$C_6$)alkoxy, —$(CH_2)_tO(CH_2)_t$($C_6$-$C_{10}$)aryl, —$(CH_2)_tN[(CH_2)_rR^9]_2$, —$(CH_2)_tN[(CH_2)_rR^9]$($C_6$-$C_{10}$)aryl, —$(CH_2)_t$(4 to 14 membered heterocyclyl), —$(CH_2)_tO(CH_2)_t$(4 to 14 membered heterocyclyl) and —$(CH_2)_t(N[(CH_2)_rR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, and wherein each said ($CH_2$) moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein $R^5$ is selected from the group consisting of —$(CH_2)_t$($C_3$-$C_{12}$)carbocyclyl, —$(CH_2)_t$($C_6$-$C_{10}$)aryl, —$(CH_2)_tN[(CH_2)_rR^9]$($C_6$-$C_{10}$)aryl, —$(CH_2)_t$(4 to 14 membered heterocyclyl), and —$(CH_2)_t(N[(CH_2)_rR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said ($CH_2$) moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein $R^5$ is —$(CH_2)_t$($C_6$-$C_{10}$)aryl, wherein each said ($CH_2$) moiety may optionally be substituted by one to two substituents independently selected from $R^6$, and wherein each said aryl and heterocyclyl are independently optionally substituted by 1 to 3 substituents selected from $R^6$.

In one embodiment the invention relates to a compound of Formula I or a pharmaceutically acceptable salt thereof wherein $R^5$ is —$(CH_2)_t$($C_6$-$C_{10}$)aryl, and is selected from the group consisting of:

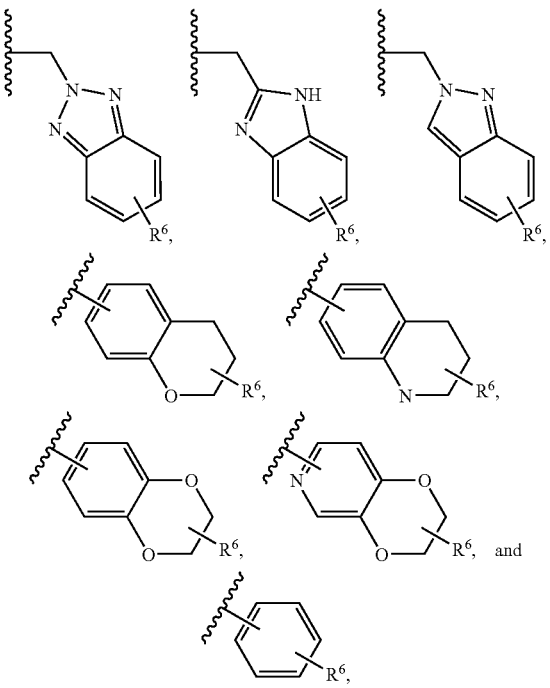

wherein each said ($CH_2$) moiety may optionally be substituted by one to two substituents independently selected substituents selected from $R^6$, and wherein each said aryl is independently optionally substituted by 1 to 3 substituents selected from $R^6$.

In one embodiment the invention relates to a compound of Formula I or a pharmaceutically acceptable salt thereof wherein $R^5$ is —$(CH_2)_t$($C_6$-$C_{10}$)aryl is selected from the group consisting of:

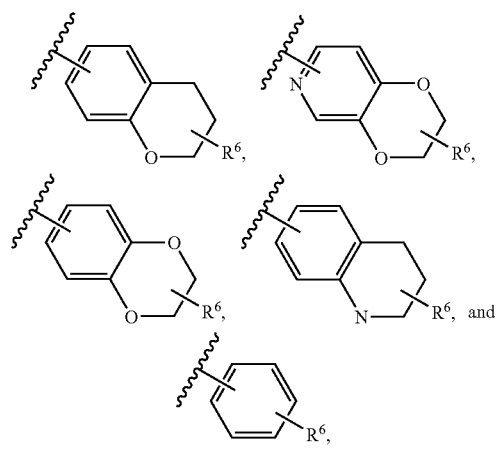

wherein each said ($CH_2$) moiety may optionally be substituted by one to two substituents independently selected substituents selected from $R^6$, and wherein each said aryl is independently optionally substituted by 1 to 3 substituents selected from $R^6$.

In one embodiment the invention relates to a compound of Formula I or a pharmaceutically acceptable salt thereof wherein $R^5$ is —$(CH_2)_t$($C_6$-$C_{10}$)aryl is selected from the group consisting of:

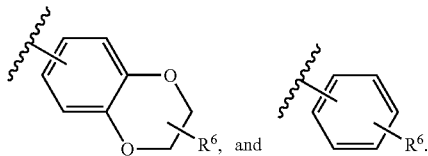

wherein each said (CH$_2$) moiety may optionally be substituted by one to two substituents independently selected substituents selected from R$^6$, and wherein each said aryl is independently optionally substituted by 1 to 3 substituents selected from R$^6$.

In one embodiment the invention relates to a compound of Formula I or a pharmaceutically acceptable salt thereof wherein R$^5$ is —(CH$_2$)$_t$(C$_3$-C$_{12}$)carbocyclyl, wherein each said (CH$_2$) moiety may optionally be substituted by one to two substituents independently selected substituents selected from R$^6$, and wherein each said carbocyclyl is independently optionally substituted by 1 to 3 substituents selected from R$^6$.

In one embodiment the invention relates to a compound of Formula I or a pharmaceutically acceptable salt thereof wherein R$^5$ is —(CH$_2$)$_t$N[(CH$_2$)$_t$R$^9$](C$_6$-C$_{10}$)aryl, wherein each said (CH$_2$) moiety may optionally be substituted by one to two substituents independently selected substituents selected from R$^6$, and wherein each said aryl is independently optionally substituted by 1 to 3 substituents selected from R$^6$.

In one embodiment the invention relates to a compound of Formula I or a pharmaceutically acceptable salt thereof wherein R$^5$ is —(CH$_2$)$_t$N[(CH$_2$)$_t$R$^9$](C$_6$-C$_{10}$)aryl and is selected from the group consisting of:

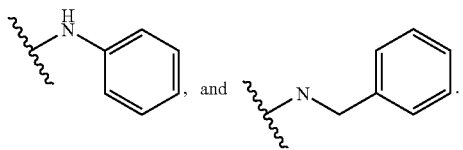

wherein each said (CH$_2$) moiety may optionally be substituted by one to two substituents independently selected substituents selected from R$^6$, and wherein each said aryl is independently optionally substituted by 1 to 3 substituents selected from R$^6$.

In one embodiment the invention relates to a compound of Formula I or a pharmaceutically acceptable salt thereof wherein R$^5$ is —(CH$_2$)$_t$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, and wherein each said (CH$_2$) moiety may optionally be substituted by one to two substituents independently selected substituents selected from R$^6$.

In one embodiment the invention relates to a compound of Formula I or a pharmaceutically acceptable salt thereof wherein R$^5$ is —(CH$_2$)$_t$(N[(CH$_2$)$_t$R$^9$])(4 to 14 membered heterocyclyl), wherein said heterocyclyl has 1 to 3 ring heteroatoms selected from the group consisting of N, O, and S, and wherein each said (CH$_2$) moiety may optionally be substituted by one to two substituents independently selected substituents selected from R$^6$.

In one embodiment the invention relates to a compound of Formula I or a pharmaceutically acceptable salt thereof wherein R$^5$ is —(CH$_2$)$_t$(N[(CH$_2$)$_t$R$^9$])(4 to 14 membered heterocyclyl) is selected from the group consisting of:

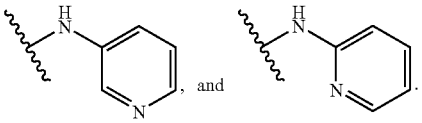

wherein each said (CH$_2$) moiety may optionally be substituted by one to two substituents independently selected substituents selected from R$^6$, and wherein each said heterocyclyl is independently optionally substituted by 1 to 3 substituents selected from R$^6$.

In one embodiment the invention relates to a compound of Formula I or a pharmaceutically acceptable salt thereof wherein each R$^6$ is independently selected from the group consisting of azide, halo, —NO$_2$, —OR$^7$, —(CH$_2$)$_t$(R$^7$), —CF$_3$, —OCF$_3$, —OCHF$_2$, —OCH$_2$F, —O(CH$_2$)$_t$(C$_6$-C$_{10}$)aryl(R$^7$), —(CH$_2$)$_t$C≡N, —(C$_1$-C$_6$)alkyl, —(CH$_2$)$_t$(C$_3$-C$_{12}$)carbocyclyl(R$^7$), —(CH$_2$)$_t$(C$_6$-C$_{10}$)aryl(R$^7$), —(CH$_2$)$_t$(4 to 14 membered heterocyclyl)(R$^7$), —(CH$_2$)$_t$SR$^7$, —(C=O)R$^7$, —(C=O)OR$^7$, —[C(R$^7$)$_2$]$_t$O(C=O)R$^7$, —[C(R$^7$)$_2$]$_t$O(C=O)N(R$^7$)$_2$, —[C(R$^7$)$_2$]$_t$N(R$^7$)(C=O)R$^7$, —[C(R$^7$)$_2$]$_t$N(R$^7$)$_2$, —[C(R$^7$)$_2$]$_t$OR$^7$, —[C(R$^7$)$_2$]$_t$N(R$^7$)(C=O)OR$^7$, —[C(R$^7$)$_2$]$_t$N(R$^7$)(C=O)N(R$^7$)$_2$, —[C(R$^7$)$_2$]$_t$N(R$^7$)N(R$^7$)$_2$, —(C=O)N(R$^7$)$_2$, —O(C=O)N(R$^7$)$_2$, —[C(R$^7$)$_2$]$_t$OR$^7$, —C(R$^7$)$_2$SR$^7$, —[C(R$^7$)$_2$]$_t$N(R$^7$)(C=O)R$^7$, —[C(R$^7$)$_2$]$_t$N(R$^7$)(C=O)OR$^7$, —C(R$^7$)=NOR$^7$ and —[C(R$^7$)$_2$]$_t$N(R$^7$)(C=O)N(R$^7$)$_2$.

In one embodiment the invention relates to a compound of Formula I or a pharmaceutically acceptable salt thereof wherein each R$^6$ is independently selected from the group consisting of azide, halo, —NO$_2$, —OR$^7$, —(CH$_2$)$_t$(R$^7$), —CF$_3$, —OCF$_3$, —(CH$_2$)$_t$C≡N, —(C$_1$-C$_6$)alkyl, —(CH$_2$)$_t$(C$_3$-C$_{12}$)carbocyclyl(R$^7$), —(CH$_2$)$_t$(C$_6$-C$_{10}$)aryl(R$^7$), —(CH$_2$)$_t$(4 to 14 membered heterocyclyl)(R$^7$), —(CH$_2$)$_t$SR$^7$, —(C=O)R$^7$, —(C=O)OR$^7$, —[C(R$^7$)$_2$]$_t$O(C=O)R$^7$, —[C(R$^7$)$_2$]$_t$O(C=O)N(R$^7$)$_2$, —[C(R$^7$)$_2$]$_t$N(R$^7$)(C=O)R$^7$, —[C(R$^7$)$_2$]$_t$N(R$^7$)$_2$, and —[C(R$^7$)$_2$]$_t$OR$^7$.

In one embodiment the invention relates to a compound of Formula I or a pharmaceutically acceptable salt thereof wherein each R$^6$ is independently selected from the group consisting of azide, halo, —OR$^7$, —CF$_3$, —OCF$_3$, —(CH$_2$)$_t$C≡N, —(C$_1$-C$_6$)alkyl, —(CH$_2$)$_t$(C$_6$-C$_{10}$)aryl(R$^7$), —(CH$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]$_t$OR$^7$.

In one embodiment the invention relates to a compound of Formula I or a pharmaceutically acceptable salt thereof wherein each R$^7$ is independently selected from the group consisting of H, —CF$_3$, —(C$_1$-C$_6$)alkyl, —(C$_6$-C$_{10}$)aryl, or two R$^7$ groups on the same nitrogen atom may be taken together with the nitrogen atom to form a 5 to 8 membered heterocyclyl ring, wherein said heterocyclyl ring has 1 to 3 ring heteroatoms selected from the group consisting of N, O, and S, or two R$^7$ groups on the same carbon atom may be taken together with the carbon atom to form a 3 to 7 membered carbocyclyl ring and wherein said alkyl, cycloalkyl, aryl, heterocyclyl and carbocyclyl may optionally be substituted by one to three substituents independently selected from the group consisting of halo, hydroxy, —CN, —(C$_1$-C$_6$)alkyl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —C(=O)(C$_1$-C$_6$)alkyl, and —(C$_3$-C$_{12}$)carbocyclyl.

In one embodiment the invention relates to a compound of Formula I or a pharmaceutically acceptable salt thereof wherein each R$^7$ is independently selected from the group consisting of H, —$CF_3$, —$(C_1-C_6)$alkyl, —$(C_6-C_{10})$aryl, wherein said alkyl, and aryl, may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$C(=O)(C_1-C_6)$alkyl, and —$(C_3-C_{12})$carbocyclyl.

In one embodiment the invention relates to a compound of Formula I or a pharmaceutically acceptable salt thereof wherein each $R^7$ is H.

In one embodiment the invention relates to a compound of Formula I or a pharmaceutically acceptable salt thereof wherein each $R^7$ is —$CF_3$.

In one embodiment the invention relates to a compound of Formula I or a pharmaceutically acceptable salt thereof wherein each $R^7$ is —$(C_1-C_6)$alkyl, wherein said alkyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$C(=O)(C_1-C_6)$alkyl, and —$(C_3-C_{12})$carbocyclyl.

In one embodiment the invention relates to a compound of Formula I or a pharmaceutically acceptable salt thereof wherein each $R^7$ is —$(C_6-C_{10})$aryl, wherein said aryl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$C(=O)(C_1-C_6)$alkyl, and —$(C_3-C_{12})$carbocyclyl.

In one embodiment the invention relates to a compound of Formula I or a pharmaceutically acceptable salt thereof wherein X is selected from the group consisting of O and S.

In one embodiment the invention relates to a compound of Formula I or a pharmaceutically acceptable salt thereof wherein X is O.

In one embodiment the invention relates to a compound of Formula I or a pharmaceutically acceptable salt thereof wherein X is S.

In one embodiment the invention relates to a compound of Formula I or a pharmaceutically acceptable salt thereof wherein $R^8$ is selected from the group consisting of hydrogen and —$(C_1-C_6)$alkyl.

In one embodiment the invention relates to a compound of Formula I or a pharmaceutically acceptable salt thereof wherein $R^8$ is hydrogen.

In one embodiment the invention relates to a compound of Formula I or a pharmaceutically acceptable salt thereof wherein $R^8$ is —$(C_1-C_6)$alkyl.

In one embodiment the invention relates to a compound of Formula I or a pharmaceutically acceptable salt thereof wherein each $R^9$ is independently selected from the group consisting of hydrogen, —$(C_1-C_6)$alkyl, —$(CH_2)_t(C_6-C_{10}$ aryl), —$(CH_2)_t(C_3-C_{12})$carbocyclyl, and —$(CH_2)_t$(4 to 14 membered heterocyclyl), wherein said heterocyclyl has 1 to 3 ring heteroatoms selected from the group consisting of N, O, and S, or two $R^9$ groups on the same nitrogen atom may be taken together with the nitrogen atom to form a 5 to 8 membered heterocyclyl ring wherein said heterocyclyl ring optionally has 1 to 3 ring additional heteroatoms selected from the group consisting of N, O, and S, or two $R^9$ groups on the same carbon atom may be taken together with the carbon atom to form a 3 to 7 membered carbocyclyl ring, wherein each said alkyl, aryl, ($CH_2$) moiety, carbocyclyl, and heterocyclyl may optionally be substituted by one to three substituents independently selected from the group consisting of —$(C_1-C_6)$alkyl, halo, hydroxy, —$(C_1-C_6)$alkoxy, —CN, —$(CH_2)_tCF_3$, —$(CH_2)_t(C_6-C_{10}$ aryl), —$NH(C_1-C_6)$alkyl, —$N[(C_1-C_6)$alkyl$]_2$ and —$(CH_2)_t$(4 to 14 membered heterocyclyl) wherein said heterocyclyl has 1 to 3 ring heteroatoms selected from the group consisting of N, O, and S.

In one embodiment the invention relates to a compound of Formula I or a pharmaceutically acceptable salt thereof wherein each $R^9$ is —$(C_1-C_6)$alkyl, or wherein two $R^9$ groups on the same carbon atom may be taken together with the carbon atom to form a 3 to 7 membered carbocyclyl ring, wherein each ($CH_2$) moiety may optionally be substituted by one to two substituents independently selected from the group consisting of —$(C_1-C_6)$alkyl, halo, hydroxy, —$(C_1-C_6)$alkoxy, —CN, —$(CH_2)_tCF_3$, —$(CH_2)_t(C_6-C_{10}$ aryl), —$NH(C_1-C_6)$alkyl, —$N[(C_1-C_6)$alkyl$]_2$ and —$(CH_2)_t$(4 to 14 membered heterocyclyl) wherein said heterocyclyl has 1 to 3 ring heteroatoms selected from the group consisting of N, O, and S, and wherein each said alkyl may optionally be substituted by one to three substituents independently selected from the group consisting of —$(C_1-C_6)$alkyl, halo, hydroxy, —$(C_1-C_6)$alkoxy, —CN, —$(CH_2)_tCF_3$, —$(CH_2)_t$ ($C_6-C_{10}$ aryl), —$NH(C_1-C_6)$alkyl, —$N[(C_1-C_6)$alkyl$]_2$ and —$(CH_2)_t$(4 to 14 membered heterocyclyl) wherein said heterocyclyl has 1 to 3 ring heteroatoms selected from the group consisting of N, O, and S.

In one embodiment the invention relates to a compound of Formula I or a pharmaceutically acceptable salt thereof wherein each $R^9$ is hydrogen.

In a embodiment the invention relates to a compound of Formula I or a pharmaceutically acceptable salt thereof wherein $R^1$ is selected from the group consisting of halo, —$(CH_2)_tCF_3$, —$(CH_2)_tC\equiv N$, —$(CH_2)_tN[(CH_2)_tR^9]_2$, —$(CH_2)_tR^9$, and —$(CH_2)_tO[(CH_2)_tR^9]$, and wherein $R^2$ is selected from the group consisting of hydrogen and —$(C_1-C_6)$alkyl, wherein each ($CH_2$) moiety may optionally be substituted by one to two substituents independently selected from the group consisting of —$(C_1-C_6)$alkyl, halo, hydroxy, —$(C_1-C_6)$alkoxy, —CN, —$(CH_2)_tCF_3$, and —$N[(CH_2)_tR^9]_2$.

In one embodiment the invention relates to a compound of Formula I or a pharmaceutically acceptable salt thereof wherein $R^1$ is selected from the group consisting of halo, —$(CH_2)_tCF_3$, —$(CH_2)_tC\equiv N$, —$(CH_2)_tN[(CH_2)_tR^9]_2$, —$(CH_2)_tR^9$, and —$(CH_2)_tO[(CH_2)_tR^9]$, and wherein $R^2$ is hydrogen, wherein each ($CH_2$) moiety may optionally be substituted by one to two substituents independently selected from the group consisting of —$(C_1-C_6)$alkyl, halo, hydroxy, —$(C_1-C_6)$alkoxy, —CN, —$(CH_2)_tCF_3$, and —$N[(CH_2)_tR^9]_2$.

In one embodiment the invention relates to a compound of Formula I or a pharmaceutically acceptable salt thereof wherein $R^1$ is selected from the group consisting of halo, —$(CH_2)_tCF_3$, —$(CH_2)_tC\equiv N$, —$(CH_2)_tN[(CH_2)_tR^9]_2$, —$(CH_2)_tR^9$, and —$(CH_2)_tO[(CH_2)_tR^9]$, and wherein each $R^{3A}$ is independently selected from the group consisting of hydrogen and —$(C_1-C_6)$alkyl, wherein each said alkyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$C(=O)(C_1-C_6)$alkyl, and —$(C_3-C_{12})$carbocyclyl.

In one embodiment the invention relates to a compound of Formula I or a pharmaceutically acceptable salt thereof wherein $R^1$ is selected from the group consisting of halo, —(CH$_2$)$_t$CF$_3$, —(CH$_2$)$_t$C≡N, —(CH$_2$)$_t$N[(CH$_2$)$_t$R$^9$]$_2$, —(CH$_2$)$_t$R$^9$, and —(CH$_2$)$_t$O[(CH$_2$)$_t$R$^9$], and wherein each R$^{3A}$ is hydrogen.

In one embodiment the invention relates to a compound of Formula I or a pharmaceutically acceptable salt thereof wherein each R$^{3A}$ is independently selected from the group consisting of hydrogen and —(C$_1$-C$_6$)alkyl, wherein each said alkyl may optionally be substituted by one to three substituents independently selected from the group consisting of halo, hydroxy, —CN, —(C$_1$-C$_6$)alkyl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl, and wherein each R$^{3B}$ is independently selected from the group consisting of hydrogen, —(C$_1$-C$_6$)alkyl, —(C=O)O(C$_1$-C$_6$)alkyl, —(CH$_2$)$_t$(C$_3$-C$_{12}$)carbocyclyl, and —(CH$_2$)$_t$(C$_6$-C$_{10}$ aryl), wherein said alkyl, carbocyclyl, and aryl may optionally be substituted by one to three substituents independently selected from the group consisting of halo, hydroxy, —CN, —(C$_1$-C$_6$)alkyl, —(C$_6$-C$_{10}$)aryl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl.

In one embodiment the invention relates to a compound of Formula I or a pharmaceutically acceptable salt thereof wherein each R$^{3A}$ is hydrogen and wherein each R$^{3B}$ is independently selected from the group consisting of hydrogen, —(C$_1$-C$_6$)alkyl, —(C=O)O(C$_1$-C$_6$)alkyl, —(CH$_2$)$_t$(C$_3$-C$_{12}$)carbocyclyl, and —(CH$_2$)$_t$(C$_6$-C$_{10}$ aryl), wherein said alkyl, carbocyclyl, or aryl may optionally be substituted by one to three substituents independently selected from the group consisting of halo, hydroxy, —CN, —(C$_1$-C$_6$)alkyl, —(C$_6$-C$_{10}$)aryl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl.

In one embodiment the invention relates to a compound of Formula I or a pharmaceutically acceptable salt thereof wherein R$^1$ is selected from the group consisting of halo, —(CH$_2$)$_t$CF$_3$, —(CH$_2$)$_t$C≡N, —(CH$_2$)$_t$N[(CH$_2$)$_t$R$^9$]$_2$, —(CH$_2$)$_t$R$^9$, and —(CH$_2$)$_t$O[(CH$_2$)$_t$R$^9$], and wherein each R$^{3B}$ is independently selected from the group consisting of hydrogen, —(C$_1$-C$_6$)alkyl, —(C=O)O(C$_1$-C$_6$)alkyl, —(CH$_2$)$_t$(C$_3$-C$_{12}$)carbocyclyl, and —(CH$_2$)$_t$(C$_6$-C$_{10}$ aryl), wherein said alkyl, alkenyl, carbocyclyl, and aryl may optionally be substituted by one to three substituents independently selected from the group consisting of halo, hydroxy, —CN, —(C$_1$-C$_6$)alkyl, —(C$_6$-C$_{10}$)aryl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl.

In one embodiment the invention relates to a compound of Formula I or a pharmaceutically acceptable salt thereof wherein R$^2$ is selected from the group consisting of hydrogen and —(C$_1$-C$_6$)alkyl, and wherein each R$^{3B}$ is independently selected from the group consisting of hydrogen, —(C$_1$-C$_6$)alkyl, —(C=O)O(C$_1$-C$_6$)alkyl, —(CH$_2$)$_t$(C$_3$-C$_{12}$)carbocyclyl, and —(CH$_2$)$_t$(C$_6$-C$_{10}$ aryl), wherein said alkyl, alkenyl, carbocyclyl, and aryl may optionally be substituted by one to three substituents independently selected from the group consisting of halo, hydroxy, —CN, —(C$_1$-C$_6$)alkyl, —(C$_6$-C$_{10}$)aryl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl.

In one embodiment the invention relates to a compound of Formula I or a pharmaceutically acceptable salt thereof wherein R$^2$ is hydrogen, and wherein each R$^{3B}$ is independently selected from the group consisting of hydrogen, —(C$_1$-C$_6$)alkyl, —(C=O)O(C$_1$-C$_6$)alkyl, —(CH$_2$)$_t$(C$_3$-C$_{12}$)carbocyclyl, and —(CH$_2$)$_t$(C$_6$-C$_{10}$ aryl), wherein said alkyl, alkenyl, carbocyclyl, and aryl may optionally be substituted by one to three substituents independently selected from the group consisting of halo, hydroxy, —CN, —(C$_1$-C$_6$)alkyl, —(C$_6$-C$_{10}$)aryl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl.

In one embodiment the invention relates to a compound of Formula I or a pharmaceutically acceptable salt thereof wherein R$^1$ is selected from the group consisting of halo, —(CH$_2$)$_t$CF$_3$, —(CH$_2$)$_t$C≡N, —(CH$_2$)$_t$N[(CH$_2$)$_t$R$^9$]$_2$, —(CH$_2$)$_t$R$^9$, and —(CH$_2$)$_t$O[(CH$_2$)$_t$R$^9$], and wherein R$^4$ is selected from the group consisting of hydrogen and —(C$_1$-C$_6$)alkyl.

In one embodiment the invention relates to a compound of Formula I or a pharmaceutically acceptable salt thereof wherein R$^1$ is selected from the group consisting of halo, —(CH$_2$)$_t$CF$_3$, —(CH$_2$)$_t$C≡N, —(CH$_2$)$_t$N[(CH$_2$)$_t$R$^9$]$_2$, —(CH$_2$)$_t$R$^9$, and —(CH$_2$)$_t$O[(CH$_2$)$_t$R$^9$], and wherein R$^4$ is hydrogen.

In one embodiment the invention relates to a compound of Formula I or a pharmaceutically acceptable salt thereof wherein each R$^{3B}$ is independently selected from the group consisting of hydrogen, —(C$_1$-C$_6$)alkyl, —(C=O)O(C$_1$-C$_6$)alkyl, —(CH$_2$)$_t$(C$_3$-C$_{12}$)carbocyclyl, and —(CH$_2$)$_t$(C$_6$-C$_{10}$ aryl), wherein said alkyl, alkenyl, carbocyclyl, and aryl may optionally be substituted by one to three substituents independently selected from the group consisting of halo, hydroxy, —CN, —(C$_1$-C$_6$)alkyl, —(C$_6$-C$_{10}$)aryl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl and wherein R$^4$ is selected from the group consisting of hydrogen and —(C$_1$-C$_6$)alkyl.

In one embodiment the invention relates to a compound of Formula I or a pharmaceutically acceptable salt thereof wherein each R$^{3B}$ is independently selected from the group consisting of hydrogen, —(C$_1$-C$_6$)alkyl, —(C=O)O(C$_1$-C$_6$)alkyl, —(CH$_2$)$_t$(C$_3$-C$_{12}$)carbocyclyl, and —(CH$_2$)$_t$(C$_6$-C$_{10}$ aryl), wherein said alkyl, alkenyl, carbocyclyl, and aryl may optionally be substituted by one to three substituents independently selected from the group consisting of halo, hydroxy, —CN, —(C$_1$-C$_6$)alkyl, —(C$_6$-C$_{10}$)aryl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —(C=O)(C$_1$-C$_6$)alkyl, and —(C$_3$-C$_{12}$)carbocyclyl and wherein R$^4$ is hydrogen.

In one embodiment the invention relates to a compound of Formula I or a pharmaceutically acceptable salt thereof wherein R$^1$ is selected from the group consisting of halo, —(CH$_2$)$_t$CF$_3$, —(CH$_2$)$_t$C≡N, —(CH$_2$)$_t$N[(CH$_2$)$_t$R$^9$]$_2$, —(CH$_2$)$_t$R$^9$, and —(CH$_2$)$_t$O[(CH$_2$)$_t$R$^9$], and wherein R$^5$ is selected from the group consisting of —(CH$_2$)$_t$(C$_3$-C$_{12}$)carbocyclyl, —(CH$_2$)$_t$(C$_6$-C$_{10}$)aryl, —(CH$_2$)$_t$N[(CH$_2$)$_t$R$^9$](C$_6$-C$_{10}$)aryl, —(CH$_2$)$_t$(4 to 14 membered heterocyclyl), and —(CH$_2$)$_t$(N[(CH$_2$)$_t$R$^9$])(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said (CH$_2$) moiety may optionally be substituted by one to two substituents independently selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein $R^2$ is selected from the group consisting of hydrogen and —$(C_1-C_6)$alkyl, and wherein $R^5$ is selected from the group consisting of —$(CH_2)_t(C_3-C_{12})$carbocyclyl, —$(CH_2)_t(C_6-C_{10})$aryl, —$(CH_2)_tN[(CH_2)_tR^9](C_6-C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, and wherein each said $(CH_2)$ moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein $R^2$ is hydrogen and wherein $R^5$ is selected from the group consisting of —$(CH_2)_t(C_3-C_{12})$carbocyclyl, —$(CH_2)_t(C_6-C_{10})$aryl, —$(CH_2)_tN[(CH_2)_tR^9](C_6-C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said $(CH_2)$ moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein each $R^{3A}$ is independently selected from the group consisting of hydrogen and —$(C_1-C_6)$alkyl, wherein each said alkyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$(C=O)O(C_1-C_6)$alkyl, —$(C=O)(C_1-C_6)$alkyl, and —$(C_3-C_{12})$carbocyclyl, and wherein $R^5$ is selected from the group consisting of —$(CH_2)_t(C_3-C_{12})$carbocyclyl, —$(CH_2)_t(C_6-C_{10})$aryl, —$(CH_2)_tN[(CH_2)_tR^9](C_6-C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said $(CH_2)$ moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein each $R^{3A}$ is hydrogen, and wherein $R^5$ is selected from the group consisting of —$(CH_2)_t(C_3-C_{12})$carbocyclyl, —$(CH_2)_t(C_6-C_{10})$aryl, —$(CH_2)_tN[(CH_2)_tR^9](C_6-C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said $(CH_2)$ moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein each $R^{3B}$ is independently selected from the group consisting of hydrogen, —$(C_1-C_6)$alkyl, —$(C=O)O(C_1-C_6)$alkyl, —$(CH_2)_t(C_3-C_{12})$carbocyclyl, and —$(CH_2)_t(C_6-C_{10})$aryl), wherein said alkyl, carbocyclyl, or aryl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$(C=O)O(C_1-C_6)$alkyl, —$(C=O)(C_1-C_6)$alkyl, and —$(C_3-C_{12})$carbocyclyl, and wherein $R^5$ is selected from the group consisting of —$(CH_2)_t(C_3-C_{12})$carbocyclyl, —$(CH_2)_t(C_6-C_{10})$aryl, —$(CH_2)_tN[(CH_2)_tR^9](C_6-C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said $(CH_2)$ moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein $R^4$ is selected from the group consisting of hydrogen and —$(C_1-C_6)$alkyl, and wherein $R^5$ is selected from the group consisting of —$(CH_2)_t(C_3-C_{12})$carbocyclyl, —$(CH_2)_t(C_6-C_{10})$aryl, —$(CH_2)_tN[(CH_2)_tR^9](C_6-C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said $(CH_2)$ moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein each $R^4$ is hydrogen, and wherein $R^5$ is selected from the group consisting of —$(CH_2)_t(C_3-C_{12})$carbocyclyl, —$(CH_2)_t(C_6-C_{10})$aryl, —$(CH_2)_tN[(CH_2)_tR^9](C_6-C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said heterocyclyl are optionally substituted with an oxo group, wherein each said $(CH_2)$ moiety may optionally be substituted by one to two substituents independently selected from $R^6$.

In one embodiment the invention relates to a compound of Formula I or a pharmaceutically acceptable salt thereof wherein $R^5$ is selected from the group consisting of —$(CH_2)_t(C_3-C_{12})$carbocyclyl, —$(CH_2)_t(C_6-C_{10})$aryl, —$(CH_2)_tN$

[(CH$_2$)$_t$R$^9$](C$_6$-C$_{10}$)aryl, —(CH$_2$)$_t$(4 to 14 membered heterocyclyl), and —(CH$_2$)$_t$(N[(CH$_2$)$_t$R$^9$])(4 to 14 membered heterocyclyl), wherein said heterocyclyl has 1 to 3 ring heteroatoms selected from the group consisting of N, O, and S, and wherein one or two carbon atoms of said aryl or heterocyclyl are optionally substituted with an oxo group, wherein each said (CH$_2$) moiety may optionally be substituted by one to two substituents independently selected substituents selected from R$^6$, and wherein each said carbocyclyl, aryl, and heterocyclyl are independently optionally substituted by 1 to 3 substituents selected from R$^6$, and wherein each R$^6$ is independently selected from the group consisting of azide, halo, —OR$^7$, —CF$_3$, —OCF$_3$, —(CH$_2$)$_t$C≡N, —(C$_1$-C$_6$) alkyl, —(CH$_2$)$_t$(C$_6$-C$_{10}$)aryl(R$^7$), —(CH$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]$_t$OR$^7$.

In one embodiment the invention relates to a compound of Formula I or a pharmaceutically acceptable salt thereof wherein R$^5$ is selected from the group consisting of

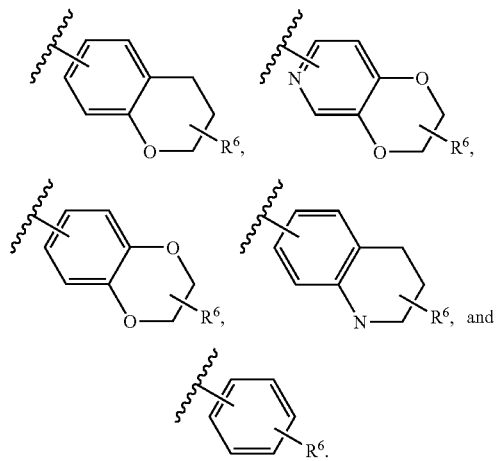

wherein one or two carbon atoms of said aryl are optionally substituted with an oxo group, wherein each said (CH$_2$) moiety may optionally be substituted by one to two substituents independently selected substituents selected from R$^6$, wherein each said aryl is independently optionally substituted by 1 to 3 substituents selected from R$^6$, and wherein each R$^6$ is independently selected from the group consisting of azide, halo, —OR$^7$, —CF$_3$, —OCF$_3$, —(CH$_2$)$_t$C≡N, —(C$_1$-C$_6$) alkyl, —(CH$_2$)$_t$(C$_6$-C$_{10}$)aryl(R$^7$), —(CH$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]$_t$OR$^7$.

In one embodiment the invention relates to a compound of Formula I or a pharmaceutically acceptable salt thereof wherein R$^5$ is selected from the group consisting of

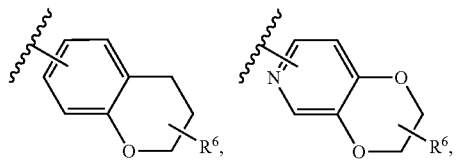

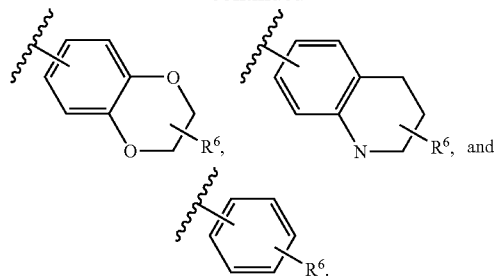

wherein one or two carbon atoms of said aryl are optionally substituted with an oxo group, wherein each said (CH$_2$) moiety may optionally be substituted by one to two substituents independently selected substituents selected from R$^6$, wherein each said aryl is independently optionally substituted by 1 to 3 substituents selected from R$^6$, wherein each R$^6$ is independently selected from the group consisting of azide, halo, —OR$^7$, —CF$_3$, —OCF$_3$, —(CH$_2$)$_t$C≡N, —(C$_1$-C$_6$) alkyl, —(CH$_2$)$_t$(C$_6$-C$_{10}$)aryl(R$^7$)$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]$_t$OR$^7$, and wherein R$^1$ is selected from the group consisting of halo, —(CH$_2$)$_t$CF$_3$, —(CH$_2$)$_t$C≡N, —(CH$_2$)$_t$N[(CH$_2$)$_t$R$^9$]$_2$, —(CH$_2$)$_t$R$^9$, and —(CH$_2$)$_t$O[(CH$_2$)$_t$R$^9$].

In one embodiment the invention relates to a compound of Formula I or a pharmaceutically acceptable salt thereof wherein R$^5$ is selected from the group consisting of

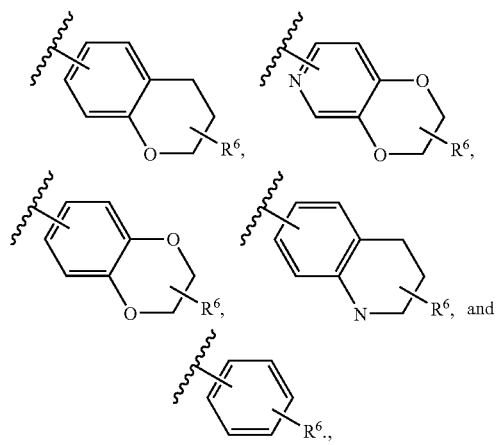

wherein one or two carbon atoms of said aryl are optionally substituted with an oxo group, wherein each said (CH$_2$) moiety may optionally be substituted by one to two substituents independently selected substituents selected from R$^6$, wherein each said aryl is independently optionally substituted by 1 to 3 substituents selected from R$^6$, wherein each R$^6$ is independently selected from the group consisting of azide, halo, —OR$^7$, —CF$_3$, —OCF$_3$, —(CH$_2$)$_t$C≡N, —(C$_1$-C$_6$) alkyl, —(CH$_2$)$_t$(C$_6$-C$_{10}$)aryl(R$^7$), —(CH$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]$_t$OR$^7$, and wherein R$^2$ is hydrogen.

In one embodiment the invention relates to a compound of Formula I or a pharmaceutically acceptable salt thereof wherein R$^5$ is selected from the group consisting of

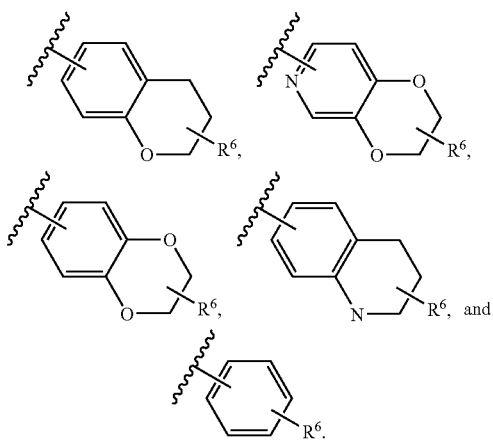

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, wherein each $R^6$ is independently selected from the group consisting of azide, halo, —$OR^7$, —$CF_3$, —$OCF_3$, —$(CH_2)_tC\equiv N$, —$(C_1-C_6)$alkyl, —$(CH_2)_t(C_6-C_{10})$aryl$(R^7)$, —$(CH_2)_t$(4 to 14 membered heterocyclyl)$(R^7)$, —$(C=O)R^7$, —$[C(R^7)_2]_tN(R^7)_2$, —$(CH_2)_tSR^7$, and —$[C(R^7)_2]_tOR^7$, and wherein $R^{3A}$ is hydrogen.

In one embodiment the invention relates to a compound of Formula I or a pharmaceutically acceptable salt thereof wherein $R^5$ is selected from the group consisting of

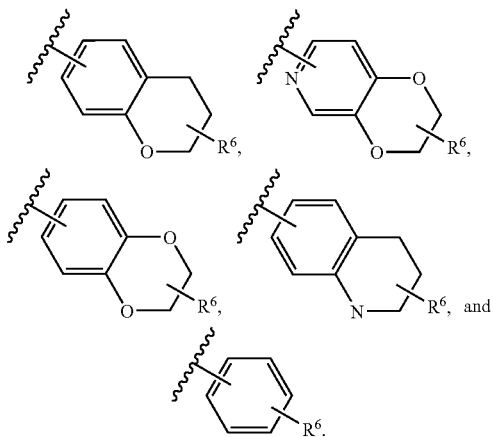

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, wherein each $R^6$ is independently selected from the group consisting of azide, halo, —$OR^7$, —$CF_3$, —$OCF_3$, —$(CH_2)_tC\equiv N$, —$(C_1-C_6)$alkyl, —$(CH_2)_t(C_6-C_{10})$aryl$(R^7)$, —$(CH_2)_t$(4 to 14 membered heterocyclyl)$(R^7)$, —$(C=O)R^7$, —$[C(R^7)_2]_tN(R^7)_2$, —$(CH_2)_tSR^7$, and —$[C(R^7)_2]_tOR^7$ and wherein each $R^{3B}$ is independently selected from the group consisting of hydrogen, —$(C_1-C_6)$alkyl, —$(C=O)O(C_1-C_6)$alkyl, —$(CH_2)_t(C_3-C_{12})$carbocyclyl, —$(CH_2)_t(C_6-C_{10}$ aryl) wherein said alkyl, carbocyclyl, or aryl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2$ $(C_1-C_6)$alkyl, —$(C=O)O(C_1-C_6)$alkyl, —$(C=O)(C_1-C_6)$alkyl, and —$(C_3-C_{12})$carbocyclyl.

In one embodiment the invention relates to a compound of Formula I or a pharmaceutically acceptable salt thereof wherein $R^5$ is selected from the group consisting of

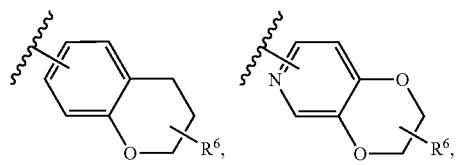

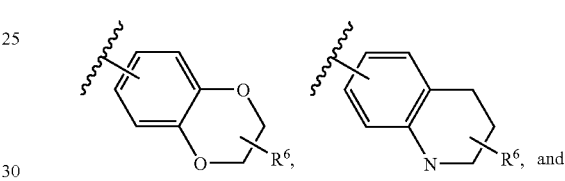

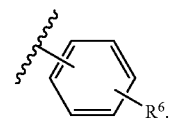

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, and wherein each $R^6$ is independently selected from the group consisting of azide, halo, —$OR^7$, —$CF_3$, —$OCF_3$, —$(CH_2)_tC\equiv N$, —$(C_1-C_6)$alkyl, —$(CH_2)_t(C_6-C_{10})$aryl$(R^7)$, —$(CH_2)_t$(4 to 14 membered heterocyclyl)$(R^7)$, —$(C=O)R^7$, —$[C(R^7)_2]_tN(R^7)_2$, —$(CH_2)_tSR^7$, and —$[C(R^7)_2]tOR^7$, and wherein $R^4$ is hydrogen.

In one embodiment the invention relates to a compound of Formula I or a pharmaceutically acceptable salt thereof wherein each $R^6$ is independently selected from the group consisting of azide, halo, —$OR^7$, —$CF_3$, —$OCF_3$, —$(CH_2)_t$ $C\equiv N$, —$(C_1-C_6)$alkyl, —$(CH_2)_t(C_6-C_{10})$aryl$(R^7)$, —$(CH_2)_t$ (4 to 14 membered heterocyclyl)$(R^7)$, —$(C=O)R^7$, —$[C(R^7)_2]_tN(R^7)_2$, —$(CH_2)_tSR^7$, and —$[C(R^7)_2]_tOR^7$, and wherein each $R^7$ is independently selected from the group consisting of H, —$CF_3$, and —$(C_1-C_6)$alkyl, wherein said alkyl may optionally be substituted by one to three substituents independently selected from the group consisting of halo, hydroxy, —CN, —$(C_1-C_6)$alkyl, —$(C_1-C_6)$alkoxy, —$CF_3$, —$OCF_3$, —$N[(CH_2)_tR^9]_2$, —$NO_2$, —$S(C_1-C_6)$alkyl, —$(S=O)(C_1-C_6)$alkyl, —$S(=O)_2(C_1-C_6)$alkyl, —$C(=O)$ $(C_1-C_6)$alkyl, and —$(C_3-C_{12})$carbocyclyl.

In one embodiment the invention relates to a compound of Formula I or a pharmaceutically acceptable salt thereof wherein $R^5$ is selected from the group consisting of

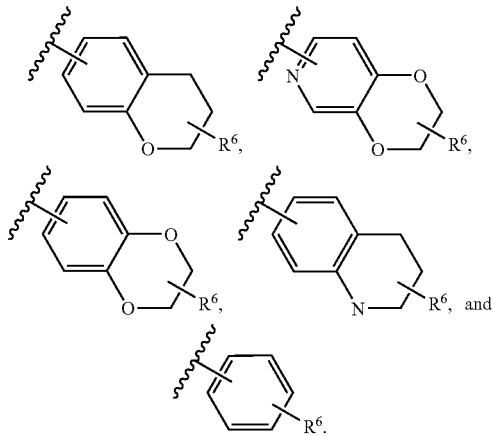

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, and wherein each $R^6$ is independently selected from the group consisting of azide, halo, —$OR^7$, —$CF_3$, —$OCF_3$, —$(CH_2)_tC\equiv N$, —($C_1$-$C_6$)alkyl, —$(CH_2)_t(C_6$-$C_{10})$aryl$(R^7)$, —$(CH_2)_t$(4 to 14 membered heterocyclyl)$(R^7)$, —$(C=O)R^7$, —$[C(R^7)_2]_tN(R^7)_2$, —$(CH_2)_tSR^7$, and —$[C(R^7)_2]tOR^7$, and wherein each $R^7$ is independently selected from the group consisting of H, —$CF_3$, and —($C_1$-$C_6$)alkyl, wherein said alkyl may optionally be substituted by one to three substituents independently selected from the group consisting of halo, hydroxy, —CN, —($C_1$-$C_6$)alkyl, —($C_1$-$C_6$)alkoxy, —$CF_3$, —$OCF_3$, —$N[(CH_2)_tR^9]_2$, —$NO_2$, —$S(C_1$-$C_6)$alkyl, —$(S=O)(C_1$-$C_6)$alkyl, —$S(=O)_2(C_1$-$C_6)$alkyl, —$(C=O)O(C_1$-$C_6)$alkyl, —$C(=O)(C_1$-$C_6)$alkyl, and —($C_3$-$C_{12}$)carbocyclyl.

In one embodiment the invention relates to a compound of Formula I or a pharmaceutically acceptable salt thereof wherein X is O and wherein $R^1$ is selected from the group consisting of halo, —$(CH_2)_tCF_3$, —$(CH_2)_tC\equiv N$, —$(CH_2)_tN[(CH_2)_tR^9]_2$, —$(CH_2)_tR^9$, and —$(CH_2)_tO[(CH_2)_tR^9]$.

In one embodiment the invention relates to a compound of Formula I or a pharmaceutically acceptable salt thereof wherein X is O and wherein $R^2$ is selected from the group consisting of hydrogen and —($C_1$-$C_6$)alkyl.

In one embodiment the invention relates to a compound of Formula I or a pharmaceutically acceptable salt thereof wherein X is O and wherein The compound of Formula I or a pharmaceutically acceptable salt thereof wherein each $R^{3A}$ is independently selected from the group consisting of hydrogen and —($C_1$-$C_6$)alkyl, wherein each said alkyl may optionally be substituted by one to three substituents independently selected from the group consisting of halo, hydroxy, —CN, —($C_1$-$C_6$)alkyl, —($C_1$-$C_6$)alkoxy, —$CF_3$, —$OCF_3$, —$N[(CH_2)_tR^9]_2$, —$NO_2$, —$S(C_1$-$C_6)$alkyl, —$(S=O)(C_1$-$C_6)$alkyl, —$(C=O)O(C_1$-$C_6)$alkyl, —$(C=O)(C_1$-$C_6)$alkyl, and —($C_3$-$C_{12}$)carbocyclyl.

In one embodiment the invention relates to a compound of Formula I or a pharmaceutically acceptable salt thereof wherein X is O and wherein each $R^{3B}$ is independently selected from the group consisting of hydrogen, —($C_1$-$C_6$) alkyl, —$(C=O)O(C_1$-$C_6)$alkyl, —$(CH_2)_t(C_3$-$C_{12})$carbocyclyl, —$(CH_2)_t(C_6$-$C_{10})$aryl), wherein said carbocyclyl, or aryl may optionally be substituted by one to three substituents independently selected from the group consisting of halo, hydroxy, —CN, —($C_1$-$C_6$)alkyl, —($C_6$-$C_{10}$)aryl, —($C_1$-$C_6$) alkoxy, —$CF_3$, —$OCF_3$, —$N[(CH_2)_tR^9]_2$, —$NO_2$, —$S(C_1$-$C_6)$alkyl, —$(S=O)(C_1$-$C_6)$alkyl, —$S(=O)_2(C_1$-$C_6)$alkyl, —$(C=O)O(C_1$-$C_6)$alkyl, —$C=O)(C_1$-$C_6)$alkyl, and —($C_3$-$C_{12}$)carbocyclyl.

In one embodiment the invention relates to a compound of Formula I or a pharmaceutically acceptable salt thereof wherein X is O and wherein $R^4$ is selected from the group consisting of hydrogen and —($C_1$-$C_6$)alkyl.

In one embodiment the invention relates to a compound of Formula I or a pharmaceutically acceptable salt thereof wherein X is O and wherein $R^5$ is selected from the group consisting of —$(CH_2)_t(C_3$-$C_{12})$carbocyclyl, —$(CH_2)_t(C_6$-$C_{10})$aryl, —$(CH_2)_tN[(CH_2)_tR^9](C_6$-$C_{10})$aryl, —$(CH_2)_t$(4 to 14 membered heterocyclyl), and —$(CH_2)_t(N[(CH_2)_tR^9])$(4 to 14 membered heterocyclyl), wherein said heterocyclyl has 1 to 3 ring heteroatoms selected from the group consisting of N, O, and S, and wherein one or two carbon atoms of said aryl or heterocyclyl are optionally substituted with an oxo group, wherein each said ($CH_2$) moiety may optionally be substituted by one to two substituents independently selected substituents selected from $R^6$, and wherein each said carbocyclyl, aryl, and heterocyclyl are independently optionally substituted by 1 to 3 substituents selected from $R^6$.

In one embodiment the invention relates to a compound of Formula I or a pharmaceutically acceptable salt thereof wherein $R^5$ is selected from the group consisting of:

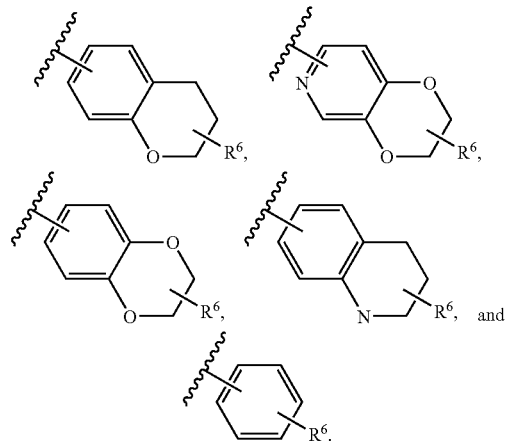

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, wherein each $R^6$ is independently selected from the group consisting of azide, halo, —$OR^7$, —$CF_3$, —$OCF_3$, —$(CH_2)_tC\equiv N$, —($C_1$-$C_6$) alkyl, —$(CH_2)_t(C_6$-$C_{10})$aryl$(R^7)$, —$(CH_2)_t$(4 to 14 membered heterocyclyl)$(R^7)$, —$(C=O)R^7$, —$[C(R^7)_2]_tN(R^7)_2$, —$(CH_2)_tSR^7$, and —$[C(R^7)_2]_tOR^7$, wherein $R^1$ is selected from the group consisting of halo, —$(CH_2)_tCF_3$, —$(CH_2)_tC\equiv N$, —$(CH_2)_tN[(CH_2)_tR^9]_2$, —$(CH_2)_tR^9$, and —$(CH_2)_tO[(CH_2)_tR^9]$, and wherein X is O.

In one embodiment the invention relates to a compound of Formula I or a pharmaceutically acceptable salt thereof wherein $R^5$ is selected from the group consisting of

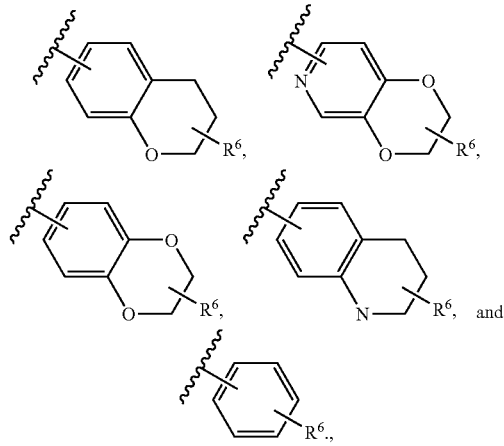

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, wherein each $R^6$ is independently selected from the group consisting of azide, halo, —$OR^7$, —$CF_3$, —$OCF_3$, —$(CH_2)_t C\equiv N$, —$(C_1-C_6)$ alkyl, —$(CH_2)_t(C_6-C_{10})$aryl($R^7$), —$(CH_2)_t$(4 to 14 membered heterocyclyl)($R^7$), —$(C=O)R^7$, —$[C(R^7)_2]_t N(R^7)_2$, —$(CH_2)_t SR^7$, and —$[C(R^7)_2]_t OR^7$, wherein $R^2$ is hydrogen, and wherein X is O.

In one embodiment the invention relates to a compound of Formula I or a pharmaceutically acceptable salt thereof wherein $R^5$ is selected from the group consisting of

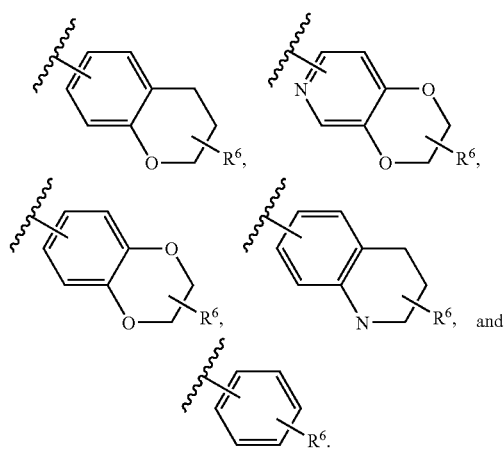

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, wherein each $R^6$ is independently selected from the group consisting of azide, halo, —$OR^7$, —$CF_3$, —$OCF_3$, —$(CH_2)_t C\equiv N$, —$(C_1-C_6)$ alkyl, —$(CH_2)_t(C_6-C_{10})$aryl($R^7$), —$(CH_2)_t$(4 to 14 membered heterocyclyl)($R^7$), —$(C=O)R^7$, —$[C(R^7)_2]_t N(R^7)_2$, —$(CH_2)_t SR^7$, and —$[C(R^7)_2]_t OR^7$, wherein $R^{3A}$ is hydrogen, and wherein X is O.

In one embodiment the invention relates to a compound of Formula I or a pharmaceutically acceptable salt thereof wherein $R^5$ is selected from the group consisting of

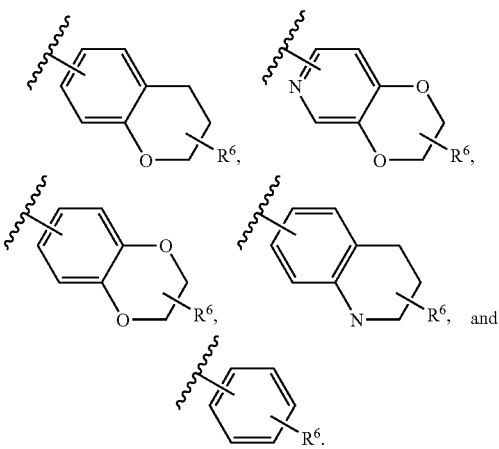

wherein one or two carbon atoms of said aryl are optionally substituted with an oxo group, wherein each said ($CH_2$) moiety may optionally be substituted by one to two substituents independently selected substituents selected from $R^6$, wherein each said aryl is independently optionally substituted by 1 to 3 substituents selected from $R^6$, wherein each $R^6$ is independently selected from the group consisting of azide, halo, —$OR^7$, —$CF_3$, —$OCF_3$, —$(CH_2)_t C\equiv N$, —$(C_1-C_6)$ alkyl, —$(CH_2)_t(C_6-C_{10})$aryl($R^7$), —$(CH_2)_t$(4 to 14 membered heterocyclyl)($R^7$), —$(C=O)R^7$, —$[C(R^7)_2]_t N(R^7)_2$, —$(CH_2)_t SR^7$, and —$[C(R^7)_2]_t OR^7$, wherein each $R^{3B}$ is independently selected from the group consisting of hydrogen, —$(C_1-C_6)$alkyl, —$(C=O)O(C_1-C_6)$alkyl, —$(CH_2)_t(C_3-C_{12})$ carbocyclyl, —$(CH_2)_t(C_6-C_{10}$ aryl), wherein said alkyl, carbocyclyl, or aryl may optionally be substituted by one to three substituents independently selected from the group consisting of halo, hydroxy, —CN, —$(C_1-C_6)$alkyl, —$(C_6-C_{10})$aryl, —$(C_1-C_6)$alkoxy, —$CF_3$, —$OCF_3$, —$N[(CH_2)_t R^9]_2$, —$NO_2$, —$S(C_1-C_6)$alkyl, —$(S=O)(C_1-C_6)$alkyl, —$S(=O)_2(C_1-C_6)$ alkyl, —$(C=O)O(C_1-C_6)$alkyl, —$(C=O)(C_1-C_6)$alkyl, and —$(C_3-C_{12})$carbocyclyl, and wherein X is O.

In one embodiment the invention relates to a compound of Formula I or a pharmaceutically acceptable salt thereof wherein $R^5$ is selected from the group consisting of

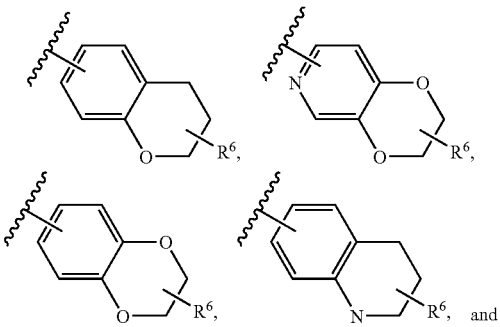

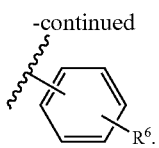

wherein one or two carbon atoms of said aryl are optionally substituted with an oxo group, wherein each said (CH$_2$) moiety may optionally be substituted by one to two substituents independently selected substituents selected from R$^6$, wherein each said aryl is independently optionally substituted by 1 to 3 substituents selected from R$^6$, and wherein each R$^6$ is independently selected from the group consisting of azide, halo, —OR$^7$, —CF$_3$, —OCF$_3$, —(CH$_2$)$_t$C≡N, —(C$_1$-C$_6$) alkyl, —(CH$_2$)$_t$(C$_6$-C$_{10}$)aryl(R$^7$), —(CH$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]tOR$^7$, wherein R$^4$ is hydrogen, and wherein X is O.

In one embodiment the invention relates to a compound of Formula I or a pharmaceutically acceptable salt thereof wherein each R$^6$ is independently selected from the group consisting of azide, halo, —OR$^7$, —CF$_3$, —OCF$_3$, —(CH$_2$)$_t$C≡N, —(C$_1$-C$_6$)alkyl, —(CH$_2$)$_t$(C$_6$-C$_{10}$)aryl(R$^7$), —(CH$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]$_t$OR$^7$, wherein each R$^7$ is independently selected from the group consisting of H, —CF$_3$, and —(C$_1$-C$_6$)alkyl, wherein said alkyl may optionally be substituted by one to three substituents independently selected from the group consisting of halo, hydroxy, —CN, —(C$_1$-C$_6$)alkyl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —C(=O)(C$_1$-C$_6$)alkyl, and —(C$_3$-C$_{12}$)carbocyclyl, and wherein X is O.

In one embodiment the invention relates to a compound of Formula I or a pharmaceutically acceptable salt thereof wherein R$^5$ is selected from the group consisting of

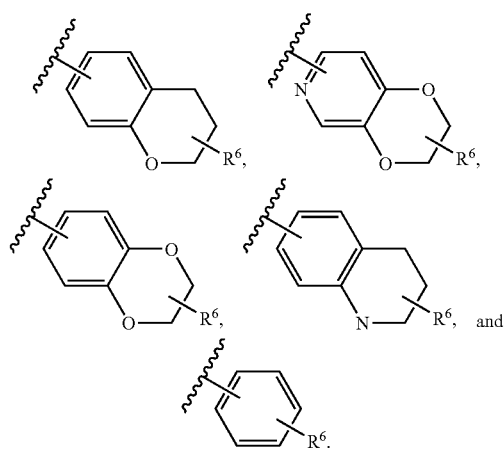

wherein one or two carbon atoms of said aryl are optionally substituted with an oxo group, wherein each said (CH$_2$) moiety may optionally be substituted by one to two substituents independently selected substituents selected from R$^6$, wherein each said aryl is independently optionally substituted by 1 to 3 substituents selected from R$^6$, and wherein each R$^6$ is independently selected from the group consisting of azide, halo, —OR$^7$, —CF$_3$, —OCF$_3$, —(CH$_2$)$_t$C≡N, —(C$_1$-C$_6$) alkyl, —(CH$_2$)$_t$(C$_6$-C$_{10}$)aryl(R$^7$), —(CH$_2$)$_t$(4 to 14 membered heterocyclyl)(R$^7$), —(C=O)R$^7$, —[C(R$^7$)$_2$]$_t$N(R$^7$)$_2$, —(CH$_2$)$_t$SR$^7$, and —[C(R$^7$)$_2$]tOR$^7$, wherein each R$^7$ is independently selected from the group consisting of H, —CF$_3$, and —(C$_1$-C$_6$)alkyl, wherein said alkyl may optionally be substituted by one to three substituents independently selected from the group consisting of halo, hydroxy, —CN, —(C$_1$-C$_6$)alkyl, —(C$_1$-C$_6$)alkoxy, —CF$_3$, —OCF$_3$, —N[(CH$_2$)$_t$R$^9$]$_2$, —NO$_2$, —S(C$_1$-C$_6$)alkyl, —(S=O)(C$_1$-C$_6$)alkyl, —S(=O)$_2$(C$_1$-C$_6$)alkyl, —(C=O)O(C$_1$-C$_6$)alkyl, —C(=O)(C$_1$-C$_6$)alkyl, and —(C$_3$-C$_{12}$)carbocyclyl, and wherein X is O.

In still another embodiment is provided a compound of Formula II(a), or II(b), or II(c), or II(d), or II(e),

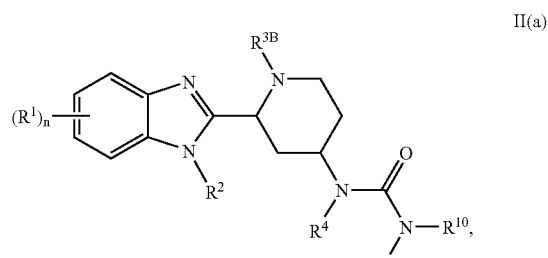

II(a)

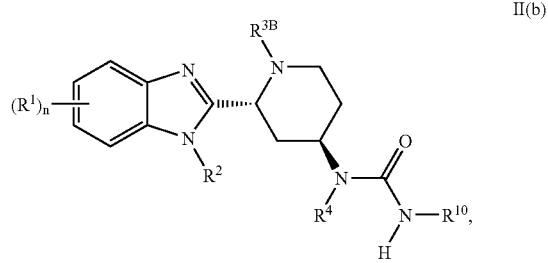

II(b)

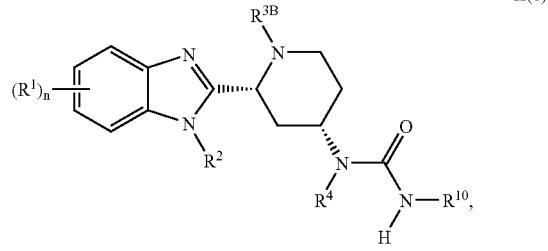

II(c)

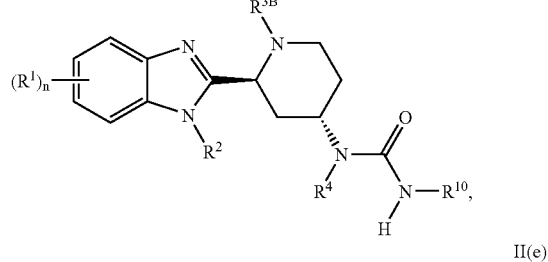

II(d)

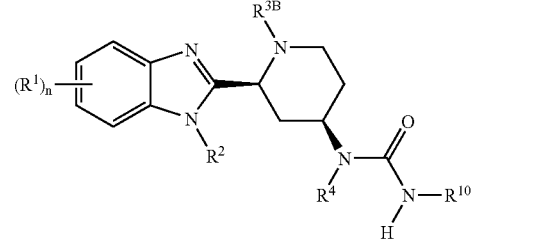

II(e)

wherein:
  each $R^1$ is independently halo, $(C_1-C_6)$alkyl, $(C_1-C_6)$alkoxy, —$CF_3$, —CN, or —$NR^{16}R^{17}$;
  $R^2$ is hydrogen or $(C_1-C_6)$alkyl;
  $R^{3B}$ is hydrogen, $(C_1-C_6)$alkyl, —$(CH_2)_t(C_6-C_{12})$aryl, or —$(CH_2)_t(C_3-C_{12})$carbocyclyl;
  $R^4$ is hydrogen or $(C_1-C_6)$alkyl;
  $R^{10}$ is —$(CH_2)_t(C_6-C_{12})$aryl or —$(CH_2)_t$(4 to 14 membered heterocyclyl), wherein each of said $(C_6-C_{12})$aryl and (4 to 14 membered heterocyclyl) is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —$C(O)C_1-C_6$ alkyl), —$C(O)CF_3$, azido, (4 to 12 membered heterocyclyl), and —$S((C_1-C_6)$alkyl);
  each $R^{16}$ and $R^{17}$ is independently selected from hydrogen and $(C_1-C_6)$alkyl;
  n is 0, 1, 2, 3, or 4; and
  each t is independently 0, 1, or 2; or
  a pharmaceutically acceptable salt thereof.

In another embodiment is provided a compound of Formula II(a), or II(b), or II(c), or II(d), or II(e), wherein:
  each $R^1$ is independently F, Cl, Br, —$CH_3$, —$OCH_3$, —$CF_3$, —CN, or —$NR^{16}R^{17}$;
  $R^2$ is hydrogen;
  $R^{3B}$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$CH_2$(phenyl);
  $R^4$ is hydrogen;
  $R^{10}$ is phenyl, pyridyl, or 2,3-dihydro-1,4-benzodioxinyl, wherein each of said phenyl, pyridyl, and 2,3-dihydro-1,4-benzodioxinyl is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —$C(O)(C_1-C_6$ alkyl), —$C(O)CF_3$, azido, (4 to 12 membered heterocyclyl), and —$S((C_1-C_6)$alkyl);
  each $R^{16}$ and $R^{17}$ is independently selected from hydrogen and $(C_1-C_6)$alkyl;
  n is 0, 1, 2, 3, or 4; and
  each t is independently 0, 1, or 2; or
  a pharmaceutically acceptable salt thereof.

In yet another embodiment is provided a compound of Formula II(a), or II(b), or II(c), or II(d), or II(e), wherein:
  each $R^1$ is independently F, Cl, —$CH_3$, —$OCH_3$, —$CF_3$, —CN, or —$N(CH_3)_2$;
  $R^2$ is hydrogen;
  $R^{3B}$ is —$CH_3$;
  $R^4$ is hydrogen;
  $R^{10}$ is phenyl, 2-pyridyl, 3-pyridyl, 4-pyridyl, or 2,3-dihydro-1,4-benzodioxin-6-yl, wherein each of said phenyl, 2-pyridyl, 3-pyridyl, 4-pyridyl, and 2,3-dihydro-1,4-benzodioxin-6-yl is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —$C(O)(C_1-C_6$ alkyl), —$C(O)CF_3$, azido, (4 to 12 membered heterocyclyl), and —$S((C_1-C_6)$alkyl);
  each $R^{16}$ and $R^{17}$ is independently selected from hydrogen and $(C_1-C_6)$alkyl;
  n is 0, 1, 2, 3, or 4; and
  each t is independently 0, 1, or 2; or
  a pharmaceutically acceptable salt thereof.

In another still embodiment is provided a compound of Formula II(a), or II(b), or II(c), or II(d), or II(e), wherein:
  each $R^1$ is independently F, Cl, —$CH_3$, —$OCH_3$, —$CF_3$, —CN, —$N(CH_3)_2$;
  $R^2$ is hydrogen;
  $R^{3B}$ is —$CH_3$;
  $R^4$ is hydrogen;
  $R^{10}$ is phenyl, 3-pyridyl, or 2,3-dihydro-1,4-benzodioxin-6-yl, wherein each of said phenyl, 3-pyridyl, and 2,3-dihydro-1,4-benzodioxin-6-yl is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —$C(O)(C_1-C_6$ alkyl), —$C(O)CF_3$, azido, (4 to 12 membered heterocyclyl), and —$S((C_1-C_6)$alkyl);
  each $R^{16}$ and $R^{17}$ is independently selected from hydrogen and $(C_1-C_6)$alkyl;
  n is 0, 1, 2, 3, or 4; and
  each t is independently 0, 1, or 2; or
  a pharmaceutically acceptable salt thereof.

A further embodiment provides a compound of Formula II(a), or II(b), or II(c), or II(d), or II(e), wherein:
  each $R^1$ is independently F, Cl, —$CH_3$, —$OCH_3$, —$CF_3$, —CN, or —$N(CH_3)_2$;
  $R^2$ is hydrogen;
  $R^{3B}$ is —$CH_3$;
  $R^4$ is hydrogen;
  $R^{10}$ is phenyl optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —$C(O)(C_1-C_6$ alkyl), —$C(O)CF_3$, azido, (4 to 12 membered heterocyclyl), and —$S((C_1-C_6)$alkyl);
  each $R^{16}$ and $R^{17}$ is independently selected from hydrogen and $(C_1-C_6)$alkyl;
  n is 0, 1, 2, 3, or 4; and
  each t is independently 0, 1, or 2; or
  a pharmaceutically acceptable salt thereof.

Further provided herein is a compound of Formula II(a), or II(b), or II(c), or II(d), or II(e),
wherein:
  each $R^1$ is independently F, Cl, —$CH_3$, —$OCH_3$, —$CF_3$, —CN, or —$N(CH_3)_2$;
  $R^2$ is hydrogen;
  $R^{3B}$ is —$CH_3$;
  $R^4$ is hydrogen;
  $R^{10}$ is phenyl optionally substituted with from 1 to 5 substituents each of which is independently selected from —$CH_3$, —CN, —F, —Cl, —Br, —$CF_3$, —$OCF_3$, —$NR^{16}R^{17}$, —$OCH_3$, and —$NO_2$;
  each $R^{16}$ and $R^{17}$ is independently selected from hydrogen and $(C_1-C_6)$alkyl; and
  n is 0, 1, 2, 3, or 4; or
  a pharmaceutically acceptable salt thereof.

In another embodiment is provided a compound of Formula II(a), or II(b), or II(c), or II(d), or II(e), wherein:
  each $R^1$ is independently F, Cl, —$CH_3$, —$OCH_3$, —$CF_3$, —CN, or —$N(CH_3)_2$;
  $R^2$ is hydrogen;
  $R^{3B}$ is —$CH_3$;
  $R^4$ is hydrogen;
  $R^{10}$ is 3-pyridyl optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —$C(O)(C_1-C_6$ alkyl), —$C(O)CF_3$, azido, (4 to 12 membered heterocyclyl), and —$S((C_1-C_6)$alkyl);
  each $R^{16}$ and $R^{17}$ is independently selected from hydrogen and $(C_1-C_6)$alkyl;
  n is 0, 1, 2, 3, or 4; and
  each t is independently 0, 1, or 2; or
  a pharmaceutically acceptable salt thereof.

In another embodiment is provided a compound of Formula II(a), or II(b), or II(c), or II(d), or II(e), wherein:

each $R^1$ is independently F, Cl, —$CH_3$, —$OCH_3$, —$CF_3$, —CN, or —$N(CH_3)_2$;
$R^2$ is hydrogen;
$R^{3B}$ is —$CH_3$;
$R^4$ is hydrogen;
$R^{10}$ is 3-pyridyl optionally substituted with from 1 to 5 substituents each of which is independently selected from —$CH_3$, —CN, —F, —Cl, —Br, —$CF_3$, —$OCF_3$, —$NR^{16}R^{17}$, —$OCH_3$, and —$NO_2$;
each $R^{16}$ and $R^{17}$ is independently selected from hydrogen and ($C_1$-$C_6$)alkyl; and
n is 0, 1, 2, 3, or 4; or
a pharmaceutically acceptable salt thereof.

In another embodiment is provided a compound of Formula II(a), or II(b), or II(c), or II(d), or II(e), wherein:

each $R^1$ is independently F, Cl, —$CH_3$, —$OCH_3$, —$CF_3$, —CN, or —$N(CH_3)_2$;
$R^2$ is hydrogen;
$R^{3B}$ is —$CH_3$;
$R^4$ is hydrogen;
$R^{10}$ is 2,3-dihydro-1,4-benzodioxin-6-yl optionally substituted with from 1 to 5 substituents each of which is independently selected from ($C_1$-$C_6$)alkyl, —CN, halo, —$CF_3$, —$OCF_3$, —$NR^{16}R^{17}$, ($C_1$-$C_6$)alkoxy, —$NO_2$, —$(CH_2)_t(C_6$-$C_{12})$aryl, —$C(O)(C_1$-$C_6$ alkyl), —$C(O)CF_3$, azido, (4 to 12 membered heterocyclyl), and —$S((C_1$-$C_6)$alkyl);
each $R^{16}$ and $R^{17}$ is independently selected from hydrogen and ($C_1$-$C_6$)alkyl;
n is 0, 1, 2, 3, or 4; and
each t is independently 0, 1, or 2; or
a pharmaceutically acceptable salt thereof.

In another embodiment is provided a compound of Formula II(a), or II(b), or II(c), or II(d), or II(e), wherein:

each $R^1$ is independently F, Cl, —$CH_3$, —$OCH_3$, —$CF_3$, —CN, or —$N(CH_3)_2$;
$R^2$ is hydrogen;
$R^{3B}$ is —$CH_3$;
$R^4$ is hydrogen;
$R^{10}$ is 2,3-dihydro-1,4-benzodioxin-6-yl optionally substituted with from 1 to 5 substituents each of which is independently selected from —$CH_3$, —CN, —F, —Cl, —Br, —$CF_3$, —$OCF_3$, —$NR^{16}R^{17}$, —$OCH_3$, and —$NO_2$;
each $R^{16}$ and $R^{17}$ is independently selected from hydrogen and ($C_1$-$C_6$)alkyl; and
n is 0, 1, 2, 3, or 4; or
a pharmaceutically acceptable salt thereof.

Further provided is a compound of Formula III(a), or III(b), or III(c), or III(d), or III(e),

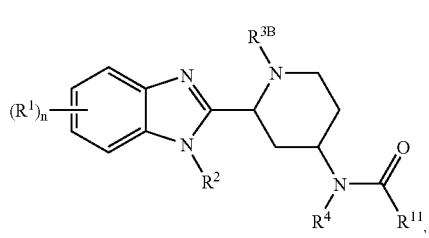

III(a)

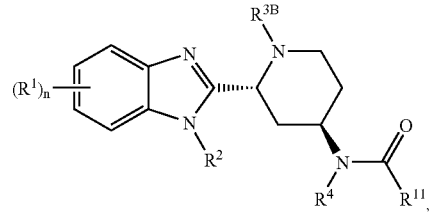

III(b)

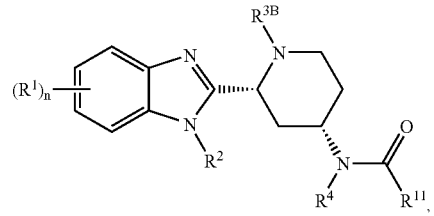

III(c)

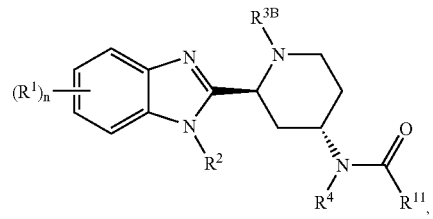

III(d)

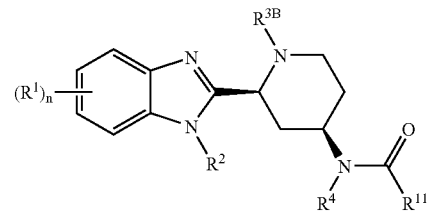

III(e)

wherein:
each $R^1$ is independently halo, ($C_1$-$C_6$)alkyl, ($C_1$-$C_6$)alkoxy, —$CF_3$, —CN, or —$NR^{16}R^{17}$;
$R^2$ is hydrogen or ($C_1$-$C_6$)alkyl;
$R^{3B}$ is hydrogen, ($C_1$-$C_6$)alkyl, —$(CH_2)_t(C_6$-$C_{12})$aryl, or —$(CH_2)_t(C_3$-$C_{12})$carbocyclyl;
$R^4$ is hydrogen or ($C_1$-$C_6$)alkyl;
$R^{11}$ is —$(CH_2)_t(C_6$-$C_{12})$aryl or —$(CH_2)_t$(4 to 14 membered heterocyclyl), wherein each of said ($C_6$-$C_{12}$)aryl and (4 to 14 membered heterocyclyl) is optionally substituted with from 1 to 5 substituents each of which is independently selected from ($C_1$-$C_6$)alkyl, —CN, halo, —$CF_3$, —$OCF_3$, —$NR^{16}R^{17}$, ($C_1$-$C_6$)alkoxy, —$NO_2$, —$(CH_2)_t(C_6$-$C_{12})$aryl, —$C(O)(C_1$-$C_6$ alkyl), —$C(O)CF_3$, azido, (4 to 12 membered heterocyclyl), and —$S((C_1$-$C_6)$alkyl);
each $R^{16}$ and $R^{17}$ is independently selected from hydrogen and ($C_1$-$C_6$)alkyl;
n is 0, 1, 2, 3, or 4; and
each t is independently 0, 1, or 2; or
a pharmaceutically acceptable salt thereof.

Further provided is a compound of Formula III(a), or III(b), or III(c), or III(d), or III(e), wherein:
each $R^1$ is independently F, Cl, Br, —$CH_3$, —$OCH_3$, —$CF_3$, —CN, or —$NR^{16}R^{17}$;
$R^2$ is hydrogen;
$R^{3B}$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$CH_2$(phenyl);

R⁴ is hydrogen;

R¹¹ is phenyl, pyridyl, or 2,3-dihydro-1,4-benzodioxinyl, wherein each of said phenyl, pyridyl, and 2,3-dihydro-1,4-benzodioxinyl is optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);

each R$^{16}$ and R$^{17}$ is independently selected from hydrogen and $(C_1-C_6)$alkyl;

n is 0, 1, 2, 3, or 4; and each t is independently 0, 1, or 2; or a pharmaceutically acceptable salt thereof.

Further provided is a compound of Formula III(a), or III(b), or III(c), or III(d), or III(e), wherein:

each R$^1$ is independently F, Cl, —CH$_3$, —OCH$_3$, —CF$_3$, —CN, or —N(CH$_3$)$_2$;

R$^2$ is hydrogen;

R$^{3B}$ is —CH$_3$;

R$^4$ is hydrogen;

R$^{11}$ is phenyl, 2-pyridyl, 3-pyridyl, 4-pyridyl, or 2,3-dihydro-1,4-benzodioxin-6-yl, wherein each of said phenyl, 2-pyridyl, 3-pyridyl, 4-pyridyl, and 2,3-dihydro-1,4-benzodioxin-6-yl is optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);

each R$^{16}$ and R$^{17}$ is independently selected from hydrogen and $(C_1-C_6)$alkyl;

n is 0, 1, 2, 3, or 4; and each t is independently 0, 1, or 2; or a pharmaceutically acceptable salt thereof.

Further provided is a compound of Formula III(a), or III(b), or III(c), or III(d), or III(e), wherein:

each R$^1$ is independently F, Cl, —CH$_3$, —OCH$_3$, —CF$_3$, —CN, or —N(CH$_3$)$_2$;

R$^2$ is hydrogen;

R$^{3B}$ is —CH$_3$;

R$^4$ is hydrogen;

R$^{11}$ is phenyl, 3-pyridyl, or 2,3-dihydro-1,4-benzodioxin-6-yl, wherein each of said phenyl, 3-pyridyl, and 2,3-dihydro-1,4-benzodioxin-6-yl is optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);

each R$^{16}$ and R$^{17}$ is independently selected from hydrogen and $(C_1-C_6)$alkyl;

n is 0, 1, 2, 3, or 4; and each t is independently 0, 1, or 2; or a pharmaceutically acceptable salt thereof.

Further provided is a compound of Formula III(a), or III(b), or III(c), or III(d), or III(e), wherein:

each R$^1$ is independently F, Cl, —CH$_3$, —OCH$_3$, —CF$_3$, —CN, or —N(CH$_3$)$_2$;

R$^2$ is hydrogen;

R$^{3B}$ is —CH$_3$;

R$^4$ is hydrogen;

R$^{11}$ is phenyl optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);

each R$^{16}$ and R$^{17}$ is independently selected from hydrogen and $(C_1-C_6)$alkyl;

n is 0, 1, 2, 3, or 4; and each t is independently 0, 1, or 2; or a pharmaceutically acceptable salt thereof.

Further provided is a compound of Formula III(a), or III(b), or III(c), or III(d), or III(e), wherein:

each R$^1$ is independently F, Cl, —CH$_3$, —OCH$_3$, —CF$_3$, —CN, or —N(CH$_3$)$_2$;

R$^2$ is hydrogen;

R$^{3B}$ is —CH$_3$;

R$^4$ is hydrogen;

R$^{11}$ is phenyl optionally substituted with from 1 to 5 substituents each of which is independently selected from —CH$_3$, —CN, —F, —Cl, —Br, —CF$_3$, —OCF$_3$, —NR$^{16}$R$^{17}$, —OCH$_3$, and —NO$_2$;

each R$^{16}$ and R$^{17}$ is independently selected from hydrogen and $(C_1-C_6)$alkyl; and n is 0, 1, 2, 3, or 4; or a pharmaceutically acceptable salt thereof.

Further provided is a compound of Formula III(a), or III(b), or III(c), or III(d), or III(e), wherein:

each R$^1$ is independently F, Cl, —CH$_3$, —OCH$_3$, —CF$_3$, —CN, or —N(CH$_3$)$_2$;

R$^2$ is hydrogen;

R$^{3B}$ is —CH$_3$;

R$^4$ is hydrogen;

R$^{11}$ is 3-pyridyl optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);

each R$^{16}$ and R$^{17}$ is independently selected from hydrogen and $(C_1-C_6)$alkyl;

n is 0, 1, 2, 3, or 4; and each t is independently 0, 1, or 2; or a pharmaceutically acceptable salt thereof.

Further provided is a compound of Formula III(a), or III(b), or III(c), or III(d), or III(e), wherein:

each R$^1$ is independently F, Cl, —CH$_3$, —OCH$_3$, —CF$_3$, —CN, or —N(CH$_3$)$_2$;

R$^2$ is hydrogen;

R$^{3B}$ is —CH$_3$;

R$^4$ is hydrogen;

R$^{11}$ is 3-pyridyl optionally substituted with from 1 to 5 substituents each of which is independently selected from —CH$_3$, —CN, —F, —Cl, —Br, —CF$_3$, —OCF$_3$, —NR$^{16}$R$^{17}$, —OCH$_3$, and —NO$_2$;

each R$^{16}$ and R$^{17}$ is independently selected from hydrogen and $(C_1-C_6)$alkyl; and n is 0, 1, 2, 3, or 4; or a pharmaceutically acceptable salt thereof.

Further provided is a compound of Formula III(a), or III(b), or III(c), or III(d), or III(e), wherein:

each R$^1$ is independently F, Cl, —CH$_3$, —OCH$_3$, —CF$_3$, —CN, or —N(CH$_3$)$_2$;

R$^2$ is hydrogen;

R$^{3B}$ is —CH$_3$;

R$^4$ is hydrogen;

R$^{11}$ is 2,3-dihydro-1,4-benzodioxin-6-yl optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-

$C_{12}$)aryl, —C(O)($C_1$-$C_6$ alkyl), —C(O)CF$_3$, azido, (4 to 12 membered heterocyclyl), and —S(($C_1$-$C_6$)alkyl);

each $R^{16}$ and $R^{17}$ is independently selected from hydrogen and ($C_1$-$C_6$)alkyl;

n is 0, 1, 2, 3, or 4; and each t is independently 0, 1, or 2; or a pharmaceutically acceptable salt thereof.

Further provided is a compound of Formula III(a), or III(b), or III(c), or III(d), or III(e), wherein:

each $R^1$ is independently F, Cl, —CH$_3$, —OCH$_3$, —CF$_3$, —CN, or —N(CH$_3$)$_2$;

$R^2$ is hydrogen;

$R^{3B}$ is —CH$_3$;

$R^4$ is hydrogen;

$R^{11}$ is 2,3-dihydro-1,4-benzodioxin-6-yl optionally substituted with from 1 to 5 substituents each of which is independently selected from —CH$_3$, —CN, —F, —Cl, —Br, —CF$_3$, —OCF$_3$, —NR$^{16}$R$^{17}$, —OCH$_3$, and —NO$_2$;

each $R^{16}$ and $R^{17}$ is independently selected from hydrogen and ($C_1$-$C_6$)alkyl; and n is 0, 1, 2, 3, or 4; or a pharmaceutically acceptable salt thereof.

Also provided herein is a compound of Formula IV(a), or IV(b), or IV(c), or IV(d), or IV(e), IV(a)

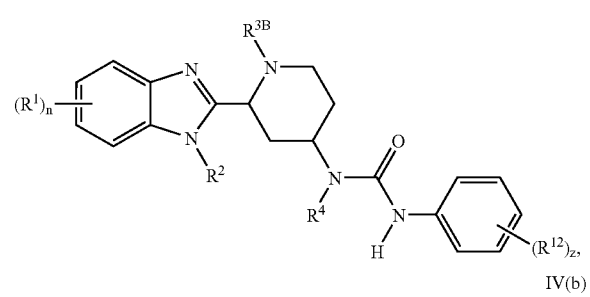

IV(b)

IV(c)

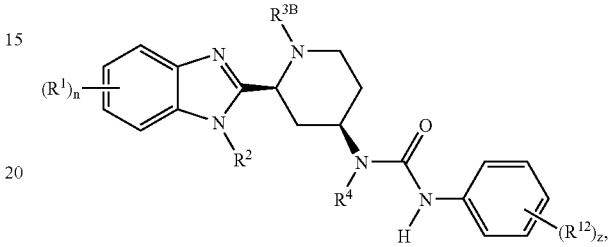

IV(d)

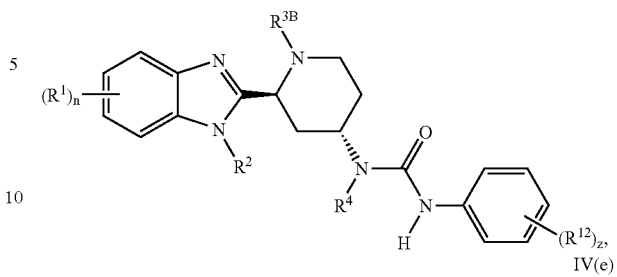

IV(e)

wherein:

each $R^1$ is independently halo, ($C_1$-$C_6$)alkyl, ($C_1$-$C_6$)alkoxy, —CF$_3$, —CN, or —NR$^{16}$R$^{17}$;

$R^2$ is hydrogen or ($C_1$-$C_6$)alkyl;

$R^{3B}$ is hydrogen, ($C_1$-$C_6$)alkyl, —(CH$_2$)$_t$($C_6$-$C_{12}$)aryl, or —(CH$_2$)$_t$($C_3$-$C_{12}$)carbocyclyl;

$R^4$ is hydrogen or ($C_1$-$C_6$)alkyl;

each $R^{12}$ is independently selected from —(CH$_2$)$_t$($C_6$-$C_{12}$)aryl, —(CH$_2$)$_t$(4 to 14 membered heterocyclyl), ($C_1$-$C_6$)alkyl, —CN, halo, —CF$_3$, —OCF$_3$, —NR$^{16}$R$^{17}$, ($C_1$-$C_6$)alkoxy, —NO$_2$, —(CH$_2$)$_t$($C_6$-$C_{12}$)aryl, —C(O)(C$_1$-C$_6$ alkyl), —C(O)CF$_3$, azido, (4 to 12 membered heterocyclyl), and —S(($C_1$-$C_6$)alkyl);

each $R^{16}$ and $R^{17}$ is independently selected from hydrogen and ($C_1$-$C_6$)alkyl;

n is 0, 1, 2, 3, or 4;

each t is independently 0, 1, or 2; and z is 0, 1, 2, 3, 4, or 5; or a pharmaceutically acceptable salt thereof.

In another embodiment is provided a compound of Formula IV(a), or IV(b), or IV(c), or IV(d), or IV(e), wherein:

each $R^1$ is independently halo, ($C_1$-$C_6$)alkyl, ($C_1$-$C_6$)alkoxy, —CF$_3$, —CN, or —NR$^{16}$R$^{17}$;

$R^2$ is hydrogen;

$R^{3B}$ is —CH$_3$;

$R^4$ is hydrogen;

each $R^{12}$ is independently selected from —CN, —F, —Cl, —Br, —CF$_3$, —OCF$_3$, —NR$^{16}$R$^{17}$, —OCH$_3$, and —NO$_2$;

each $R^{16}$ and $R^{17}$ is independently selected from hydrogen and ($C_1$-$C_6$)alkyl;

n is 0, 1, 2, 3, or 4; and z is 0, 1, 2, 3, 4, or 5; or a pharmaceutically acceptable salt thereof.

Further provided is a compound of Formula IV(a), or IV(b), or IV(c), or IV(d), or IV(e), wherein:

each $R^1$ is independently halo, —CH$_3$, —OCH$_3$, —CF$_3$, —CN, or —N(CH$_3$)$_2$;

$R^2$ is hydrogen;

$R^{3B}$ is —CH$_3$;

$R^4$ is hydrogen;

$R^{12}$ is —CN, —F, —Cl, —Br, —CF$_3$, —OCF$_3$, —OCH$_3$, or —NO$_2$;

n is 0, 1, 2, 3, or 4; and z is 1; or a pharmaceutically acceptable salt thereof.

Further provided is a compound of Formula IV(a), or IV(b), or IV(c), or IV(d), or IV(e), wherein:

$R^2$ is hydrogen;

$R^{3B}$ is —$CH_3$;

$R^4$ is hydrogen;

$R^{12}$ is —CN, —F, —Cl, —Br, or —$CF_3$;

n is 0; and z is 1; or a pharmaceutically acceptable salt thereof.

Further provided is a compound of Formula IV(a), or IV(b), or IV(c), or IV(d), or IV(e), wherein:

$R^2$ is hydrogen;

$R^{3B}$ is —$CH_3$;

$R^4$ is hydrogen;

$R^{12}$ is —CN;

n is 0; and z is 1; or a pharmaceutically acceptable salt thereof.

Further provided herein is a compound of Formula V(a), or V(b), or V(c), or V(d), or V(e), V(a)
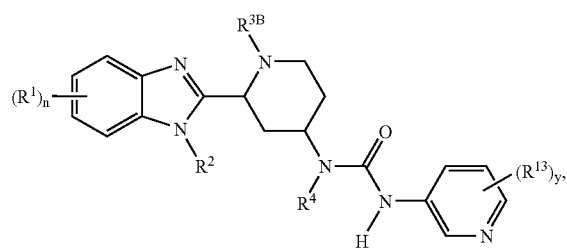

V(b)
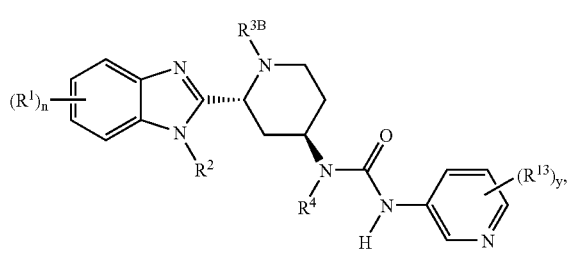

V(c)
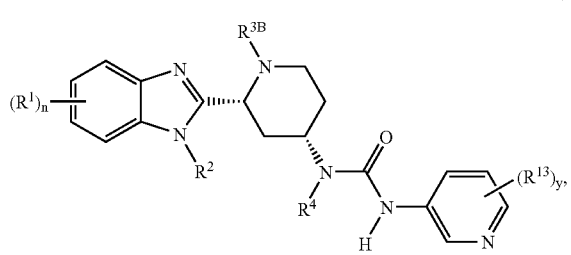

V(d)
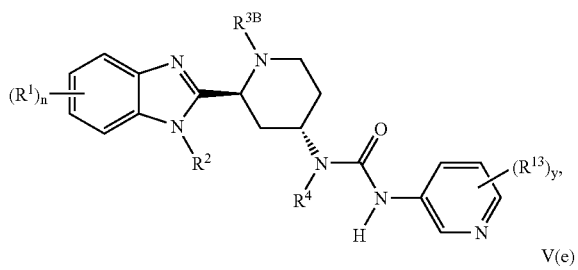

V(e)
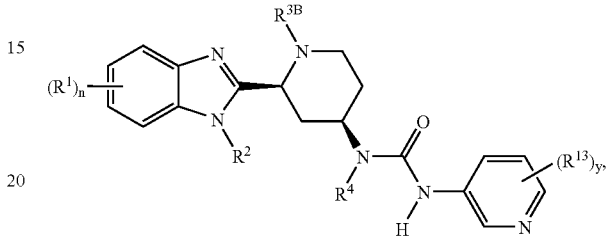

wherein:

each $R^1$ is independently halo, $(C_1-C_6)$alkyl, $(C_1-C_6)$alkoxy, —$CF_3$, —CN, or —$NR^{16}R^{17}$;

$R^2$ is hydrogen or $(C_1-C_6)$alkyl;

$R^{3B}$ is hydrogen, $(C_1-C_6)$alkyl, —$(CH_2)_t(C_6-C_{12})$aryl, or —$(CH_2)_t(C_3-C_{12})$carbocyclyl;

$R^4$ is hydrogen or $(C_1-C_6)$alkyl;

each $R^{13}$ is independently selected from —$(CH_2)_t(C_6-C_{12})$aryl, —$(CH_2)_t$(4 to 14 membered heterocyclyl), $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —$C(O)(C_1-C_6$ alkyl), —$C(O)CF_3$, azido, (4 to 12 membered heterocyclyl), and —$S((C_1-C_6)$alkyl);

each $R^{16}$ and $R^{17}$ is independently selected from hydrogen and $(C_1-C_6)$alkyl;

n is 0, 1, 2, 3, or 4;

each t is independently 0, 1, or 2; and y is 0, 1, 2, 3, or 4; or a pharmaceutically acceptable salt thereof.

In another embodiment is provided a compound of Formula VI(a), or VI(b), or VI(c), or VI(d), or VI(e), VI(a)
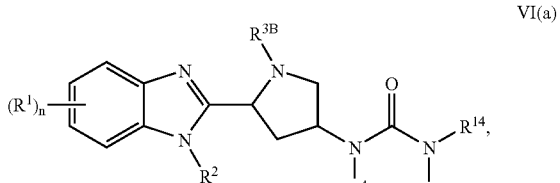

VI(b)
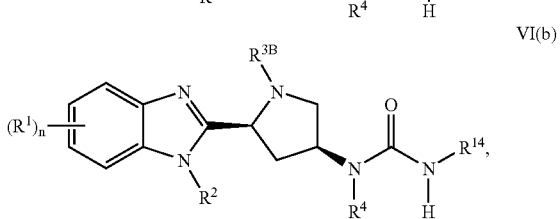

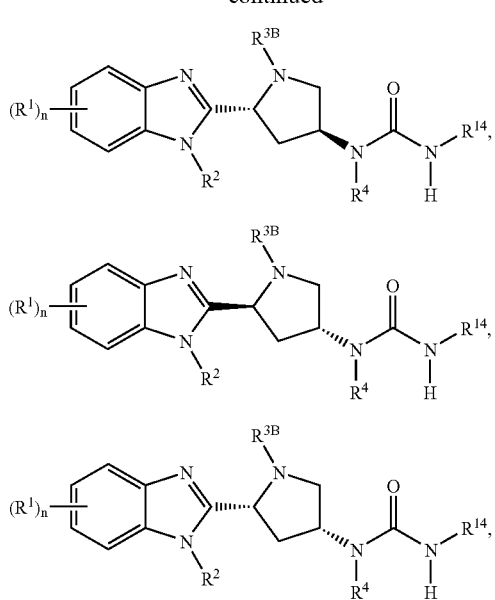

wherein:

each $R^1$ is independently halo, $(C_1$-$C_6)$alkyl, $(C_1$-$C_6)$alkoxy, —$CF_3$, —CN, or —$NR^{16}R^{17}$;

$R^2$ is hydrogen or $(C_1$-$C_6)$alkyl;

$R^{3B}$ is hydrogen, $(C_1$-$C_6)$alkyl, —$(CH_2)_t(C_6$-$C_{12})$aryl, —$(CH_2)_t(C_3$-$C_{12})$carbocyclyl; —$C(O)O(C_1$-$C_6$ alkyl) or —$C(O)O(C_6$-$C_{12})$aryl;

$R^4$ is hydrogen or $(C_1$-$C_6)$alkyl;

$R^{14}$ is —$(CH_2)_t(C_6$-$C_{12})$aryl or —$(CH_2)_t$(4 to 14 membered heterocyclyl), wherein each of said $(C_6$-$C_{12})$aryl and (4 to 14 membered heterocyclyl) is optionally substituted with from 1 to 5 substituents each of which is independently selected from $(C_1$-$C_6)$alkyl, —CN, halo, —$CF_3$, —$OCF_3$, —$NR^{16}R^{17}$, $(C_1$-$C_6)$alkoxy, —$NO_2$, —$(CH_2)_t(C_6$-$C_{12})$aryl, —$C(O)(C_1$-$C_6$ alkyl), —$C(O)CF_3$, azido, (4 to 12 membered heterocyclyl), and —$S((C_1$-$C_6)$alkyl);

each $R^{16}$ and $R^{17}$ is independently selected from hydrogen and $(C_1$-$C_6)$alkyl;

n is 0, 1, 2, 3, or 4; and each t is independently 0, 1, or 2; or a pharmaceutically acceptable salt thereof.

In another embodiment is provided a compound of Formula VI(a), or VI(b), or VI(c), or VI(d), or VI(e), wherein:

each $R^1$ is independently F, Cl, Br, —$CH_3$, —$OCH_3$, —$CF_3$, —CN, or —$NR^{16}R^{17}$;

$R^2$ is hydrogen;

$R^{3B}$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$CH_2$(phenyl);

$R^4$ is hydrogen;

$R^{14}$ is phenyl, pyridyl, or 2,3-dihydro-1,4-benzodioxinyl, wherein each of said phenyl, pyridyl, and 2,3-dihydro-1,4-benzodioxinyl is optionally substituted with from 1 to 5 substituents each of which is independently selected from $(C_1$-$C_6)$alkyl, —CN, halo, —$CF_3$, —$OCF_3$, —$NR^{16}R^{17}$, $(C_1$-$C_6)$alkoxy, —$NO_2$, —$(CH_2)_t(C_6$-$C_{12})$aryl, —$C(O)(C_1$-$C_6$ alkyl), —$C(O)CF_3$, azido, (4 to 12 membered heterocyclyl), and —$S((C_1$-$C_6)$alkyl);

each $R^{16}$ and $R^{17}$ is independently selected from hydrogen and $(C_1$-$C_6)$alkyl;

n is 0, 1, 2, 3, or 4; and each t is independently 0, 1, or 2; or a pharmaceutically acceptable salt thereof.

In another embodiment is provided a compound of Formula VI(a), or VI(b), or VI(c), or VI(d), or VI(e), wherein:

each $R^1$ is independently F, Cl, —$CH_3$, —$OCH_3$, —$CF_3$, —CN, or —$N(CH_3)_2$;

$R^2$ is hydrogen;

$R^{3B}$ is —$CH_3$;

$R^4$ is hydrogen;

$R^{14}$ is phenyl, 2-pyridyl, 3-pyridyl, 4-pyridyl, or 2,3-dihydro-1,4-benzodioxin-6-yl, wherein each of said phenyl, 2-pyridyl, 3-pyridyl, 4-pyridyl, and 2,3-dihydro-1,4-benzodioxin-6-yl is optionally substituted with from 1 to 5 substituents each of which is independently selected from $(C_1$-$C_6)$alkyl, —CN, halo, —$CF_3$, —$OCF_3$, —$NR^{16}R^{17}$, $(C_1$-$C_6)$alkoxy, —$NO_2$, —$(CH_2)_t(C_6$-$C_{12})$aryl, —$C(O)(C_1$-$C_6$ alkyl), —$C(O)CF_3$, azido, (4 to 12 membered heterocyclyl), and —$S((C_1$-$C_6)$alkyl);

each $R^{16}$ and $R^{17}$ is independently selected from hydrogen and $(C_1$-$C_6)$alkyl;

n is 0, 1, 2, 3, or 4; and each t is independently 0, 1, or 2; or a pharmaceutically acceptable salt thereof.

In another embodiment is provided a compound of Formula VI(a), or VI(b), or VI(c), or VI(d), or VI(e), wherein:

each $R^1$ is independently F, Cl, —$CH_3$, —$OCH_3$, —$CF_3$, —CN, or —$N(CH_3)_2$;

$R^2$ is hydrogen;

$R^{3B}$ is —$CH_3$;

$R^4$ is hydrogen;

$R^{14}$ is phenyl, 3-pyridyl, or 2,3-dihydro-1,4-benzodioxin-6-yl, wherein each of said phenyl, 3-pyridyl, and 2,3-dihydro-1,4-benzodioxin-6-yl is optionally substituted with from 1 to 5 substituents each of which is independently selected from $(C_1$-$C_6)$alkyl, —CN, halo, —$CF_3$, —$OCF_3$, —$NR^{16}R^{17}$, $(C_1$-$C_6)$alkoxy, —$NO_2$, —$(CH_2)_t(C_6$-$C_{12})$aryl, —$C(O)(C_1$-$C_6$ alkyl), —$C(O)CF_3$, azido, (4 to 12 membered heterocyclyl), and —$S((C_1$-$C_6)$alkyl);

each $R^{16}$ and $R^{17}$ is independently selected from hydrogen and $(C_1$-$C_6)$alkyl;

n is 0, 1, 2, 3, or 4; and each t is independently 0, 1, or 2; or a pharmaceutically acceptable salt thereof.

In another embodiment is provided a compound of Formula VI(a), or VI(b), or VI(c), or VI(d), or VI(e), wherein:

each $R^1$ is independently F, Cl, —$CH_3$, —$OCH_3$, —$CF_3$, —CN, or —$N(CH_3)_2$;

$R^2$ is hydrogen;

$R^{3B}$ is —$CH_3$;

$R^4$ is hydrogen;

$R^{14}$ is phenyl optionally substituted with from 1 to 5 substituents each of which is independently selected from $(C_1$-$C_6)$alkyl, —CN, halo, —$CF_3$, —$OCF_3$, —$NR^{16}R^{17}$, $(C_1$-$C_6)$alkoxy, —$NO_2$, —$(CH_2)_t(C_6$-$C_{12})$aryl, —$C(O)(C_1$-$C_6$ alkyl), —$C(O)CF_3$, azido, (4 to 12 membered heterocyclyl), and —$S((C_1$-$C_6)$alkyl);

each $R^{16}$ and $R^{17}$ is independently selected from hydrogen and $(C_1$-$C_6)$alkyl;

n is 0, 1, 2, 3, or 4; and each t is independently 0, 1, or 2; or a pharmaceutically acceptable salt thereof.

In another embodiment is provided a compound of Formula VI(a), or VI(b), or VI(c), or VI(d), or VI(e), wherein:

each $R^1$ is independently F, Cl, —$CH_3$, —$OCH_3$, —$CF_3$, —CN, or —$N(CH_3)_2$;

$R^2$ is hydrogen;

$R^{3B}$ is —$CH_3$;

$R^4$ is hydrogen;

R[14] is phenyl optionally substituted with from 1 to 5 substituents each of which is independently selected from —CH$_3$, —CN, —F, —Cl, —Br, —CF$_3$, —OCF$_3$, —NR[16]R[17], —OCH$_3$, and —NO$_2$;
each R[16] and R[17] is independently selected from hydrogen and (C$_1$-C$_6$)alkyl; and
n is 0, 1, 2, 3, or 4; or
a pharmaceutically acceptable salt thereof.

In another embodiment is provided a compound of Formula VI(a), or VI(b), or VI(c), or VI(d), or VI(e), wherein:
each R[1] is independently F, Cl, —CH$_3$, —OCH$_3$, —CF$_3$, —CN, or —N(CH$_3$)$_2$;
R[2] is hydrogen;
R[3B] is —CH$_3$;
R[4] is hydrogen;
R[14] is 3-pyridyl optionally substituted with from 1 to 5 substituents each of which is independently selected from (C$_1$-C$_6$)alkyl, —CN, halo, —CF$_3$, —OCF$_3$, —NR[16]R[17], (C$_1$-C$_6$)alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);
each R[16] and R[17] is independently selected from hydrogen and (C$_1$-C$_6$)alkyl;
n is 0, 1, 2, 3, or 4; and
each t is independently 0, 1, or 2; or
a pharmaceutically acceptable salt thereof.

In another embodiment is provided a compound of Formula VI(a), or VI(b), or VI(c), or VI(d), or VI(e), wherein:
each R[1] is independently F, Cl, —CH$_3$, —OCH$_3$, —CF$_3$, —CN, or —N(CH$_3$)$_2$;
R[2] is hydrogen;
R[3B] is —CH$_3$;
R[4] is hydrogen;
R[14] is 3-pyridyl optionally substituted with from 1 to 5 substituents each of which is independently selected from —CH$_3$, —CN, —F, —Cl, —Br, —CF$_3$, —OCF$_3$, —NR[16]R[17], —OCH$_3$, and —NO$_2$;
each R[16] and R[17] is independently selected from hydrogen and (C$_1$-C$_6$)alkyl; and
n is 0, 1, 2, 3, or 4; or
a pharmaceutically acceptable salt thereof.

In another embodiment is provided a compound of Formula VI(a), or VI(b), or VI(c), or VI(d), or VI(e), wherein:
each R[1] is independently F, Cl, —CH$_3$, —OCH$_3$, —CF$_3$, —CN, or —N(CH$_3$)$_2$;
R[2] is hydrogen;
R[3B] is —CH$_3$;
R[4] is hydrogen;
R[14] is 2,3-dihydro-1,4-benzodioxin-6-yl optionally substituted with from 1 to 5 substituents each of which is independently selected from (C$_1$-C$_6$)alkyl, —CN, halo, —CF$_3$, —OCF$_3$, —NR[16]R[17], (C$_1$-C$_6$)alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);
each R[16] and R[17] is independently selected from hydrogen and (C$_1$-C$_6$)alkyl;
n is 0, 1, 2, 3, or 4; and
each t is independently 0, 1, or 2; or
a pharmaceutically acceptable salt thereof.

In another embodiment is provided a compound of Formula VI(a), or VI(b), or VI(c), or VI(d), or VI(e), wherein:
each R[1] is independently F, Cl, —CH$_3$, —OCH$_3$, —CF$_3$, —CN, or —N(CH$_3$)$_2$;
R[2] is hydrogen;
R[3B] is —CH$_3$;
R[4] is hydrogen;
R[14] is 2,3-dihydro-1,4-benzodioxin-6-yl optionally substituted with from 1 to 5 substituents each of which is independently selected from —CH$_3$, —CN, —F, —Cl, —Br, —CF$_3$, —OCF$_3$, —NR[16]R[17], —OCH$_3$, and —NO$_2$;
each R[16] and R[17] is independently selected from hydrogen and (C$_1$-C$_6$)alkyl; and
n is 0, 1, 2, 3, or 4; or
a pharmaceutically acceptable salt thereof.

In another embodiment is provided a compound of Formula VII(a), or VII(b), or VII(c), or VII(d), or VII(e), VII(a)

VII(b)

VII(c)

VII(d)

VII(e)

wherein:
each R[1] is independently halo, (C$_1$-C$_6$)alkyl, (C$_1$-C$_6$)alkoxy, —CF$_3$, —CN, or —NR[16]R[17];
R[2] is hydrogen or (C$_1$-C$_6$)alkyl;
R[3B] is hydrogen, (C$_1$-C$_6$)alkyl, —(CH$_2$)$_t$(C$_6$-C$_{12}$)aryl, —(CH$_2$)$_t$(C$_3$-C$_{12}$)carbocyclyl, —C(O)O(C$_1$-C$_6$)alkyl, or —C(O)O(C$_6$-C$_{12}$)aryl;
R[4] is hydrogen or (C$_1$-C$_6$)alkyl;
R[15] is —(CH$_2$)$_t$(C$_6$-C$_{12}$)aryl or —(CH$_2$)$_t$(4 to 14 membered heterocyclyl), wherein each of said (C$_6$-C$_{12}$)aryl and (4 to 14 membered heterocyclyl) is optionally substituted with from 1 to 5 substituents each of which is independently selected from (C$_1$-C$_6$)alkyl, —CN, halo, —CF$_3$, —OCF$_3$, —NR[16]R[17], (C$_1$-C$_6$)alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);

each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

In another embodiment is provided a compound of Formula VII(a), or VII(b), or VII(c), or VII(d), or VII(e), wherein:
each $R^1$ is independently F, Cl, Br, —CH$_3$, —OCH$_3$, —CF$_3$, —CN, or —NR$^{16}$R$^{17}$;
$R^2$ is hydrogen;
$R^{3B}$ is hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —CH$_2$(phenyl);
$R^4$ is hydrogen;
$R^{15}$ is phenyl, pyridyl, or 2,3-dihydro-1,4-benzodioxinyl, wherein each of said phenyl, pyridyl, and 2,3-dihydro-1,4-benzodioxinyl is optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);
each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

In another embodiment is provided a compound of Formula VII(a), or VII(b), or VII(c), or VII(d), or VII(e), wherein:
each $R^1$ is independently F, Cl, —CH$_3$, —OCH$_3$, —CF$_3$, —CN, or —N(CH$_3$)$_2$;
$R^2$ is hydrogen;
$R^{3B}$ is —CH$_3$;
$R^4$ is hydrogen;
$R^{15}$ is phenyl, 2-pyridyl, 3-pyridyl, 4-pyridyl, or 2,3-dihydro-1,4-benzodioxin-6-yl, wherein each of said phenyl, 2-pyridyl, 3-pyridyl, 4-pyridyl, and 2,3-dihydro-1,4-benzodioxin-6-yl is optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);
each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

In another embodiment is provided a compound of Formula VII(a), or VII(b), or VII(c), or VII(d), or VII(e), wherein:
each $R^1$ is independently F, Cl, —CH$_3$, —OCH$_3$, —CF$_3$, —CN, or —N(CH$_3$)$_2$;
$R^2$ is hydrogen;
$R^{3B}$ is —CH$_3$;
$R^4$ is hydrogen;
$R^{15}$ is phenyl, 3-pyridyl, or 2,3-dihydro-1,4-benzodioxin-6-yl, wherein each of said phenyl, 3-pyridyl, and 2,3-dihydro-1,4-benzodioxin-6-yl is optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);
each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

In another embodiment is provided a compound of Formula VII(a), or VII(b), or VII(c), or VII(d), or VII(e), wherein:
each $R^1$ is independently F, Cl, —CH$_3$, —OCH$_3$, —CF$_3$, —CN, or —N(CH$_3$)$_2$;
$R^2$ is hydrogen;
$R^{3B}$ is —CH$_3$;
$R^4$ is hydrogen;
$R^{15}$ is phenyl optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);
each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

In another embodiment is provided a compound of Formula VII(a), or VII(b), or VII(c), or VII(d), or VII(e), wherein:
each $R^1$ is independently F, Cl, —CH$_3$, —OCH$_3$, —CF$_3$, —CN, or —N(CH$_3$)$_2$;
$R^2$ is hydrogen;
$R^{3B}$ is —CH$_3$;
$R^4$ is hydrogen;
$R^{15}$ is phenyl optionally substituted with from 1 to 5 substituents each of which is independently selected from —CH$_3$, —CN, —F, —Cl, —Br, —CF$_3$, —OCF$_3$, —NR$^{16}$R$^{17}$, —OCH$_3$, and —NO$_2$;
each $R^{16}$ and $R^{17}$ is independently selected from hydrogen and $(C_1-C_6)$alkyl; and
n is 0, 1, 2, 3, or 4; or
a pharmaceutically acceptable salt thereof.

In another embodiment is provided a compound of Formula VII(a), or VII(b), or VII(c), or VII(d), or VII(e), wherein:
each $R^1$ is independently F, Cl, —CH$_3$, —OCH$_3$, —CF$_3$, —CN, or —N(CH$_3$)$_2$;
$R^2$ is hydrogen;
$R^{3B}$ is —CH$_3$;
$R^4$ is hydrogen;
$R^{15}$ is 3-pyridyl optionally substituted with from 1 to 5 substituents each of which is independently selected from $(C_1-C_6)$alkyl, —CN, halo, —CF$_3$, —OCF$_3$, —NR$^{16}$R$^{17}$, $(C_1-C_6)$alkoxy, —NO$_2$, —(CH$_2$)$_t$(C$_6$-C$_{12}$)aryl, —C(O)(C$_1$-C$_6$ alkyl), —C(O)CF$_3$, azido, (4 to 12 membered heterocyclyl), and —S((C$_1$-C$_6$)alkyl);
each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

In another embodiment is provided a compound of Formula VII(a), or VII(b), or VII(c), or VII(d), or VII(e), wherein:
each $R^1$ is independently F, Cl, —CH$_3$, —OCH$_3$, —CF$_3$, —CN, or —N(CH$_3$)$_2$;
$R^2$ is hydrogen;
$R^{3B}$ is —CH$_3$;
$R^4$ is hydrogen;
$R^{15}$ is 3-pyridyl optionally substituted with from 1 to 5 substituents each of which is independently selected from —CH$_3$, —CN, —F, —Cl, —Br, —CF$_3$, —OCF$_3$, —NR$^{16}$R$^{17}$, —OCH$_3$, and —NO$_2$;
each $R^{16}$ and $R^{17}$ is independently selected from hydrogen and $(C_1-C_6)$alkyl; and
n is 0, 1, 2, 3, or 4; or
a pharmaceutically acceptable salt thereof.

In another embodiment is provided a compound of Formula VII(a), or VII(b), or VII(c), or VII(d), or VII(e), wherein:

each $R^1$ is independently F, Cl, —$CH_3$, —$OCH_3$, —$CF_3$, —CN, or —$N(CH_3)_2$;

$R^2$ is hydrogen;

$R^{3B}$ is —$CH_3$;

$R^4$ is hydrogen;

$R^{15}$ is 2,3-dihydro-1,4-benzodioxin-6-yl optionally substituted with from 1 to 5 substituents each of which is independently selected from ($C_1$-$C_6$)alkyl, —CN, halo, —$CF_3$, —$OCF_3$, —$NR^{16}R^{17}$, ($C_1$-$C_6$)alkoxy, —$NO_2$, —$(CH_2)_t(C_6$-$C_{12})$aryl, —C(O)($C_1$-$C_6$ alkyl), —C(O)$CF_3$, azido, (4 to 12 membered heterocyclyl), and —S(($C_1$-$C_6$)alkyl);

each $R^{16}$ and $R^{17}$ is independently selected from hydrogen and ($C_1$-$C_6$)alkyl;

n is 0, 1, 2, 3, or 4; and each t is independently 0, 1, or 2; or a pharmaceutically acceptable salt thereof.

In another embodiment is provided a compound of Formula VII(a), or VII(b), or VII(c), or VII(d), or VII(e), wherein:

each $R^1$ is independently F, Cl, —$CH_3$, —$OCH_3$, —$CF_3$, —CN, or —$N(CH_3)_2$;

$R^2$ is hydrogen;

$R^{3B}$ is —$CH_3$;

$R^4$ is hydrogen;

$R^{15}$ is 2,3-dihydro-1,4-benzodioxin-6-yl optionally substituted with from 1 to 5 substituents each of which is independently selected from —$CH_3$, —CN, —F, —Cl, —Br, —$CF_3$, —$OCF_3$, —$NR^{16}R^{17}$, —$OCH_3$, and —$NO_2$;

each $R^{16}$ and $R^{17}$ is independently selected from hydrogen and ($C_1$-$C_6$)alkyl; and n is 0, 1, 2, 3, or 4; or a pharmaceutically acceptable salt thereof.

It is specifically contemplated herein that each of Formulae I, II(a), II(b), II(c), II(d), II(e), III(a), III(b), III(c), III(d), II(e), IV(a), IV(b), IV(c), IV(d), IV(e), V(a), V(b), V(c), V(d), V(e), VI(a), VI(b), VI(c), VI(d), VI(e), VII(a), VII(b), VII(c), VII(d), and VII(e) are intended to represent separate embodiments.

In one embodiment the invention relates to a compound of Formula I, wherein said compound is selected from the group consisting of:

5-chloro-N-[(2R,4R)-2-(5-chloro-1H-benzimidazol-2-yl)-1-methylpiperidin-4-yl]-2,3-dihydro-1,4-benzodioxine-6-carboxamide;

N-[(2R,4R)-2-(1H-benzimidazol-2-yl)-1-cyclopropylpiperidin-4-yl]-2,3-dihydro-1,4-benzodioxine-6-carboxamide;

1-[(2R,4R)-1-cyclobutyl-2-(5-methyl-1H-benzimidazol-2-yl)piperidin-4-yl]-3-(6-methylpyridin-3-yl)urea;

1-[(2R,4R)-2-(5,6-dimethyl-1H-benzimidazol-2-yl)-1-methylpiperidin-4-yl]-3-(6-methylpyridin-3-yl)urea;

1-(6-methyl pyridin-3-yl)-3-{(2R,4R)-1-methyl-2-[5-(trifluoromethyl)-1H-benzimidazol-2-yl]piperidin-4-yl}urea;

1-[(2R,4R)-2-(5,6-dimethyl-1H-benzimidazol-2-yl)-1-methylpiperidin-4-yl]-3-(6-methoxypyridin-3-yl)urea;

1-[(2R,4R)-1-cyclobutyl-2-(5,6-dimethyl-1H-benzimidazol-2-yl)piperidin-4-yl]-3-(6-methylpyridin-3-yl)urea;

1-[(2R,4R)-2-(1H-benzimidazol-2-yl)-1-cyclobutylpiperidin-4-yl]-3-(6-methylpyridin-3-yl)urea;

1-(6-methoxypyridin-3-yl)-3-{(2R,4R)-1-methyl-2-[5-(trifluoromethyl)-1H-benzimidazol-2-yl]piperidin-4-yl}urea;

1-[(2R,4R)-1-methyl-2-(5-methyl-1H-benzimidazol-2-yl)piperidin-4-yl]-3-(6-methylpyridin-3-yl)urea;

1-[(2R,4R)-2-(6-chloro-1H-benzimidazol-2-yl)-1-methylpiperidin-4-yl]-3-(6-methylpyridin-3-yl)urea;

N-[(2R,4R)-2-(5-chloro-1H-benzimidazol-2-yl)-1-methylpiperidin-4-yl]-5-fluoro-2,3-dihydro-1,4-benzodioxine-6-carboxamide;

N-[(2R,4R)-2-(1H-benzimidazol-2-yl)-1-methylpiperidin-4-yl]-2,3-dihydro-1,4-benzodioxine-6-carbothioamide;

1-[(2R,4R)-2-(5-methoxy-1H-benzimidazol-2-yl)-1-methylpiperidin-4-yl]-3-(6-methoxypyridin-3-yl)urea;

1-(6-methoxypyridin-3-yl)-3-[(2R,4R)-1-methyl-2-(5-methyl-1H-benzimidazol-2-yl)piperidin-4-yl]urea;

N-[(2R,4R)-2-(1H-benzimidazol-2-yl)-1-methylpiperidin-4-yl]-5-chloro-2,3-dihydro-1,4-benzodioxine-6-carboxamide;

1-[(2R,4R)-2-(6-chloro-1H-benzimidazol-2-yl)-1-methylpiperidin-4-yl]-3-(6-methoxypyridin-3-yl)urea;

1-[(2R,4R)-2-(5-cyano-1H-benzimidazol-2-yl)-1-methylpiperidin-4-yl]-3-(6-methoxypyridin-3-yl)urea;

1-[(2R,4R)-2-(5-methoxy-1H-benzimidazol-2-yl)-1-methylpiperidin-4-yl]-3-(6-methylpyridin-3-yl)urea;

1-[(2R,4R)-2-(5-cyano-1H-benzimidazol-2-yl)-1-methylpiperidin-4-yl]-3-(6-methylpyridin-3-yl)urea;

5-chloro-N-[(2R,4R)-2-(5-methoxy-1H-benzimidazol-2-yl)-1-methylpiperidin-4-yl]-2,3-dihydro-1,4-benzodioxine-6-carboxamide;

1-[(2R,4R)-1-cyclobutyl-2-(5-methoxy-1H-benzimidazol-2-yl)piperidin-4-yl]-3-(6-methylpyridin-3-yl)urea;

1-[(2R,4R)-2-(6-fluoro-1H-benzimidazol-2-yl)-1-methylpiperidin-4-yl]-3-(6-methylpyridin-3-yl)urea;

5-fluoro-N-[(2R,4R)-2-(5-methoxy-1H-benzimidazol-2-yl)-1-methylpiperidin-4-yl]-2,3-dihydro-1,4-benzodioxine-6-carboxamide;

1-[(2R,4R)-2-(6-fluoro-1H-benzimidazol-2-yl)-1-methylpiperidin-4-yl]-3-(6-methoxypyridin-3-yl)urea;

N-[(2R,4R)-2-(1H-benzimidazol-2-yl)-1-methylpiperidin-4-yl]-7-chloro-2,3-dihydro-1,4-benzodioxine-6-carboxamide;

N-[(2R,4R)-2-(1H-benzimidazol-2-yl)-1-methylpiperidin-4-yl]-5-fluoro-2,3-dihydro-1,4-benzodioxine-6-carboxamide;

7-chloro-N-[(2R,4R)-2-(5-chloro-1H-benzimidazol-2-yl)-1-methylpiperidin-4-yl]-2,3-dihydro-1,4-benzodioxine-6-carboxamide;

7-chloro-N-[(2R,4R)-2-(5-methoxy-1H-benzimidazol-2-yl)-1-methylpiperidin-4-yl]-2,3-dihydro-1,4-benzodioxine-6-carboxamide;

1-(4-cyanophenyl)-3-[(2R,4R)-2-(5,6-dimethyl-1H-benzimidazol-2-yl)-1-methylpiperidin-4-yl]urea;

1-[(2R,4R)-2-(1H-benzimidazol-2-yl)-1-cyclobutylpiperidin-4-yl]-3-(4-cyanophenyl)urea;

1-(4-cyanophenyl)-3-[(2R,4R)-1-methyl-2-(5-methyl-1H-benzimidazol-2-yl)piperidin-4-yl]urea;

1-(4-cyanophenyl)-3-[(2R,4R)-2-(5-methoxy-1H-benzimidazol-2-yl)-1-methylpiperidin-4-yl]urea;

1-[(2R,4R)-2-(5,6-dimethyl-1H-benzimidazol-2-yl)-1-methylpiperidin-4-yl]-3-[6-(trifluoromethyl)pyridin-3-yl]urea;

1-[(2R,4R)-2-(6-chloro-1H-benzimidazol-2-yl)-1-methylpiperidin-4-yl]-3-[6-(trifluoromethyl)pyridin-3-yl]urea;

1-[(2R,4R)-2-(1H-benzimidazol-2-yl)-1-methylpiperidin-4-yl]-3-(4-cyanophenyl)urea;

1-[(2R,4R)-2-(1H-benzimidazol-2-yl)-1-methylpiperidin-4-yl]-3-[4-(trifluoromethyl)phenyl]urea;

1-(4-cyanophenyl)-3-[(2R,4R)-2-(5-fluoro-1H-benzimidazol-2-yl)-1-methylpiperidin-4-yl]urea;

1-[(2R,4R)-2-(1H-benzimidazol-2-yl)-1-propylpiperidin-4-yl]-3-(4-cyanophenyl)urea;

5-chloro-N-[(2R,4R)-2-(5-chloro-1H-benzimidazol-2-yl)-1-methylpiperidin-4-yl]-2,3-dihydro-1,4-benzodioxine-6-carboxamide;

1-[(2R,4R)-1-methyl-2-(5-methyl-1H-benzimidazol-2-yl)piperidin-4-yl]-3-[6-(trifluoromethyl)pyridin-3-yl]urea;

1-{(2R,4R)-1-methyl-2-[5-(trifluoromethyl)-1H-benzimidazol-2-yl]piperidin-4}-3-[6-(trifluoromethyl)pyridin-3-yl]urea;

N-[(2R,4R)-2-(1H-benzimidazol-2-yl)-1-cyclopropylpiperidin-4-yl]-2,3-dihydro-1,4-benzodioxine-6-carboxamide;

1-[(2R,4R)-2-(5-methoxy-1H-benzimidazol-2-yl)-1-methylpiperidin-4-yl]-3-[6-(trifluoromethyl)pyridin-3-yl]urea;

1-[(2R,4R)-2-(1H-benzimidazol-2-yl)-1-methylpiperidin-4-yl]-3-(4-chlorophenyl)urea;

1-[(2R,4R)-1-cyclobutyl-2-(5-methyl-1H-benzimidazol-2-yl)piperidin-4-yl]-3-(6-methylpyridin-3-yl)urea;

1-[(2R,4R)-2-(5,6-dimethyl-1H-benzimidazol-2-yl)-1-methylpiperidin-4-yl]-3-(6-methylpyridin-3-yl)urea;

1-[(2R,4R)-2-(1H-benzimidazol-2-yl)-1-methylpiperidin-4-yl]-3-[4-chloro-3-(trifluoromethyl)phenyl]urea;

1-[(2R,4R)-2-(5-cyano-1H-benzimidazol-2-yl)-1-methylpiperidin-4-yl]-3-(4-cyanophenyl)urea;

1-[(2R,4R)-2-(1H-benzimidazol-2-yl)-1-methylpiperidin-4-yl]-3-(3,5-dichlorophenyl)urea;

1-(6-methyl pyridin-3-yl)-3-{(2R,4R)-1-methyl-2-[5-(trifluoromethyl)-1H-benzimidazol-2-yl]piperidin-4-yl}urea;

1-[(2R,4R)-2-(1H-benzimidazol-2-yl)-1-ethylpiperidin-4-yl]-3-(4-cyanophenyl)urea;

1-[(2R,4R)-2-(1H-benzimidazol-2-yl)-1-methylpiperidin-4-yl]-3-[6-(trifluoromethyl)pyridin-3-yl]urea;

1-[(2R,4R)-2-(1H-benzimidazol-2-yl)-1-methylpiperidin-4-yl]-3-(6-fluoropyridin-3-yl)urea;

1-(4-cyanophenyl)-3-{(2R,4R)-1-methyl-2-[5-(trifluoromethyl)-1H-benzimidazol-2-yl]piperidin-4-yl}urea;

N-[(2R,4R)-1-methyl-2-(6-methyl-1H-benzimidazol-2-yl)piperidin-4-yl]-2,3-dihydro-1,4-benzodioxine-6-carboxamide;

1-[(2R,4R)-2-(1H-benzimidazol-2-yl)-1-methylpiperidin-4-yl]-3-(4-isopropylphenyl)urea;

1-[(2R,4R)-2-(1H-benzimidazol-2-yl)-1-methylpiperidin-4-yl]-3-(6-methylpyridin-3-yl)urea;

1-[(2R,4R)-2-(5-cyano-1H-benzimidazol-2-yl)-1-methylpiperidin-4-yl]-3-[6-(trifluoromethyl)pyridin-3-yl]urea;

1-[(2R,4R)-2-(5,6-dimethyl-1H-benzimidazol-2-yl)-1-methylpiperidin-4-yl]-3-(6-methoxypyridin-3-yl)urea;

1-[(2R,4R)-2-(1H-benzimidazol-2-yl)-1-methylpiperidin-4-yl]-3-[4-(trifluoromethoxy)phenyl]urea;

1-[(2R,4R)-2-(6-fluoro-1H-benzimidazol-2-yl)-1-methylpiperidin-4-yl]-3-[6-(trifluoromethyl)pyridin-3-yl]urea;

1-[(2R,4R)-1-cyclobutyl-2-(5,6-dimethyl-1H-benzimidazol-2-yl)piperidin-4-yl]-3-(6-methylpyridin-3-yl)urea;

1-[(2R,4R)-2-(1H-benzimidazol-2-yl)-1-cyclobutylpiperidin-4-yl]-3-(6-methylpyridin-3-yl)urea;

1-(6-methoxypyridin-3-yl)-3-{(2R,4R)-1-methyl-2-[5-(trifluoromethyl)-1H-benzimidazol-2-yl]piperidin-4-yl}urea;

1-[(2R,4R)-2-(1H-benzimidazol-2-yl)-1-methylpiperidin-4-yl]-3-(6-fluoro-4H-1,3-benzodioxin-8-yl)urea;

1-[(2R,4R)-2-(1H-benzimidazol-2-yl)-1-methylpiperidin-4-yl]-3-(4-methoxyphenyl)urea;

1-[(2R,4R)-1-methyl-2-(5-methyl-1H-benzimidazol-2-yl)piperidin-4-yl]-3-(6-methylpyridin-3-yl)urea;

N-[(2R,4R)-2-(6-chloro-1H-benzimidazol-2-yl)-1-methylpiperidin-4-yl]-2,3-dihydro-1,4-benzodioxine-6-carboxamide;

N-[(2R,4R)-2-(6-cyano-1H-benzimidazol-2-yl)-1-methylpiperidin-4-yl]-2,3-dihydro-1,4-benzodioxine-6-carboxamide;

N-[(2R,4R)-2-(5,6-dimethyl-1H-benzimidazol-2-yl)-1-methylpiperidin-4-yl]-2,3-dihydro-1,4-benzodioxine-6-carboxamide;

1-[(2R,4R)-2-(1H-benzimidazol-2-yl)-1-methylpiperidin-4-yl]-3-(2,3-dihydro-1,4-benzodioxin-6-yl)urea;

1-[(2R,4R)-2-(6-chloro-1H-benzimidazol-2-yl)-1-methylpiperidin-4-yl]-3-(6-methylpyridin-3-yl)urea;

N-[(2R,4R)-2-(5-chloro-1H-benzimidazol-2-yl)-1-methylpiperidin-4-yl]-5-fluoro-2,3-dihydro-1,4-benzodioxine-6-carboxamide;

N-{(2R,4R)-1-methyl-2-[6-(trifluoromethyl)-1H-benzimidazol-2-yl]piperidin-4-yl}-2,3-dihydro-1,4-benzodioxine-6-carboxamide;

N-[(2R,4R)-2-(1H-benzimidazol-2-yl)-1-methylpiperidin-4-yl]-2,3-dihydro-1,4-benzodioxine-6-carbothioamide;

1-[(2R,4R)-2-(5-methoxy-1H-benzimidazol-2-yl)-1-methylpiperidin-4-yl]-3-(6-methoxypyridin-3-yl)urea;

1-(6-methoxypyridin-3-yl)-3-[(2R,4R)-1-methyl-2-(5-methyl-1H-benzimidazol-2-yl)piperidin-4-yl]urea;

N-[(2R,4R)-2-(1H-benzimidazol-2-yl)-1-methylpiperidin-4-yl]chromane-6-carboxamide;

1-[(2R,4R)-2-(1H-benzimidazol-2-yl)-1-isobutylpiperidin-4-yl]-3-(4-cyanophenyl)urea;

N-[(2R,4R)-2-(1H-benzimidazol-2-yl)-1-methylpiperidin-4-yl]-5-chloro-2,3-dihydro-1,4-benzodioxine-6-carboxamide;

1-[(2R,4R)-2-(6-chloro-1H-benzimidazol-2-yl)-1-methylpiperidin-4-yl]-3-(6-methoxypyridin-3-yl)urea;

1-[(2R,4R)-2-(1H-benzimidazol-2-yl)-1-methylpiperidin-4-yl]-3-(3-cyanophenyl)urea;

1-[(2R,4R)-2-(5-cyano-1H-benzimidazol-2-yl)-1-methylpiperidin-4-yl]-3-(6-methoxypyridin-3-yl)urea;

1-[(2R,4R)-2-(1H-benzimidazol-2-yl)-1-methylpiperidin-4-yl]-3-(6-methoxypyridin-3-yl)urea;

1-[4-chloro-3-(trifluoromethyl)phenyl]-3-[(3S,5S)-5-(6-methoxy-1H-benzimidazol-2-yl)-1-methylpyrrolidin-3-yl]urea;

N-[(2R,4R)-2-(1H-benzimidazol-2-yl)-1-ethylpiperidin-4-yl]-2,3-dihydro-1,4-benzodioxine-6-carboxamide;

1-[(2R,4R)-2-(5-methoxy-1H-benzimidazol-2-yl)-1-methylpiperidin-4-yl]-3-(6-methylpyridin-3-yl)urea;

N-[(2R,4R)-2-(6-methoxy-1H-benzimidazol-2-yl)-1-methylpiperidin-4-yl]-2,3-dihydro-1,4-benzodioxine-6-carboxamide;

1-[(2R,4R)-2-(1H-benzimidazol-2-yl)-1-methylpiperidin-4-yl]-3-[4-(dimethylamino)phenyl]urea;

1-[(2R,4R)-2-(1H-benzimidazol-2-yl)-1-methylpiperidin-4-yl]-3-phenylurea;

1-[(2R,4R)-2-(1H-benzimidazol-2-yl)-1-methylpiperidin-4-yl]-3-(5,6-dimethylpyridin-3-yl)urea;

1-[(2R,4R)-2-(5-cyano-1H-benzimidazol-2-yl)-1-methylpiperidin-4-yl]-3-(6-methylpyridin-3-yl)urea;

5-chloro-N-[(2R,4R)-2-(5-methoxy-1H-benzimidazol-2-yl)-1-methylpiperidin-4-yl]-2,3-dihydro-1,4-benzodioxine-6-carboxamide;

N-[(2R,4R)-2-(6-fluoro-1H-benzimidazol-2-yl)-1-methylpiperidin-4-yl]-2,3-dihydro-1,4-benzodioxine-6-carboxamide;

1-[(2R,4R)-1-cyclobutyl-2-(5-methoxy-1H-benzimidazol-2-yl)piperidin-4-yl]-3-(6-methylpyridin-3-yl)urea;

1-[(2R,4R)-2-(6-fluoro-1H-benzimidazol-2-yl)-1-methylpiperidin-4-yl]-3-(6-methylpyridin-3-yl)urea;

1-[4-chloro-3-(trifluoromethyl)phenyl]-3-[(3S,5S)-1-methyl-5-(6-methyl-1H-benzimidazol-2-yl)pyrrolidin-3-yl]urea; and 5-fluoro-N-[(2R,4R)-2-(5-methoxy-1H-benzimidazol-2-yl)-1-methylpiperidin-4-yl]-2,3-dihydro-1,4-benzodioxine-6-carboxamide; or a pharmaceutically acceptable salt thereof.

In one embodiment the invention relates to a compound of Formula I wherein said compound is N-[(2R,4R)-2-(1H-benzimidazol-2-yl)-1-cyclopropylpiperidin-4-yl]-2,3-dihydro-1,4-benzodioxine-6-carboxamide, or a pharmaceutically acceptable salt thereof.

In one embodiment the invention relates to a compound of Formula I wherein said compound is 1-[(2R,4R)-1-cyclobutyl-2-(5,6-dimethyl-1H-benzimidazol-2-yl)piperidin-4-yl]-3-(6-methylpyridin-3-yl)urea, or a pharmaceutically acceptable salt thereof.

In one embodiment the invention relates to a compound of Formula I wherein said compound is N-[(2R,4R)-2-(5-chloro-1H-benzimidazol-2-yl)-1-methylpiperidin-4-yl]-5-fluoro-2,3-dihydro-1,4-benzodioxine-6-carboxamide, or a pharmaceutically acceptable salt thereof.

In one embodiment the invention relates to a compound of Formula I wherein said compound is 1-[(2R,4R)-2-(5-cyano-1H-benzimidazol-2-yl)-1-methylpiperidin-4-yl]-3-(6-methylpyridin-3-yl)urea, or a pharmaceutically acceptable salt thereof.

In one embodiment the invention relates to a compound of Formula I wherein said compound is 1-(4-cyanophenyl)-3-[(2R,4R)-2-(5,6-dimethyl-1H-benzimidazol-2-yl)-1-methylpiperidin-4-yl]urea, or a pharmaceutically acceptable salt thereof.

In one embodiment the invention relates to a compound of Formula I wherein said compound is 1-[(2R,4R)-2-(1H-benzimidazol-2-yl)-1-methylpiperidin-4-yl]-3-(4-cyanophenyl)urea, or a pharmaceutically acceptable salt thereof.

In one embodiment the invention relates to a compound of Formula I wherein said compound is 1-[(2R,4R)-1-methyl-2-(5-methyl-1H-benzimidazol-2-yl)piperidin-4-yl]-3-[6-(trifluoromethyl)pyridin-3-yl]urea, or a pharmaceutically acceptable salt thereof.

In one embodiment the invention relates to a compound of Formula I wherein said compound is N-[(2R,4R)-1-methyl-2-(6-methyl-1H-benzimidazol-2-yl)piperidin-4-yl]-2,3-dihydro-1,4-benzodioxine-6-carboxamide, or a pharmaceutically acceptable salt thereof.

In one embodiment the invention relates to a compound of Formula I wherein said compound is 5-fluoro-N-[(2R,4R)-2-(5-methoxy-1H-benzimidazol-2-yl)-1-methylpiperidin-4-yl]-2,3-dihydro-1,4-benzodioxine-6-carboxamide, or a pharmaceutically acceptable salt thereof.

In one embodiment the invention relates to a compound of Formula I wherein said compound is 7-chloro-N-[(2R,4R)-2-(5-methoxy-1H-benzimidazol-2-yl)-1-methylpiperidin-4-yl]-2,3-dihydro-1,4-benzodioxine-6-carboxamide, or a pharmaceutically acceptable salt thereof.

In one embodiment the invention relates to a compound of Formula I wherein said compound is 1-(4-cyanophenyl)-3-[(2R,4R)-2-(5-fluoro-1H-benzimidazol-2-yl)-1-methylpiperidin-4-yl]urea, or a pharmaceutically acceptable salt thereof.

In one embodiment the invention relates to a compound of Formula I wherein said compound is 1-[(2R,4R)-2-(5,6-dimethyl-1H-benzimidazol-2-yl)-1-methylpiperidin-4-yl]-3-(6-methylpyridin-3-yl)urea, or a pharmaceutically acceptable salt thereof.

The present invention also relates to a method for the treatment of abnormal cell growth in a mammal comprising administering to said mammal an amount of a compound of Formula I or a pharmaceutically acceptable salt thereof that is effective in treating abnormal cell growth.

As used herein, the terms "crystalline and non-crystalline forms," "forms," or any reference to a compound of Formula I per se (unless otherwise specified), is meant to include any acceptable crystalline and non-crystalline freebase, solvate, hydrate, isomorph, polymorph, salt or prodrug thereof.

In one embodiment the abnormal cell growth is cancer.

In one embodiment, the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In one embodiment, the present invention relates to a method for the treatment of cancer solid tumor in a mammal comprising administering to said mammal an amount of a compound of Formula I or a pharmaceutically acceptable salt thereof that is effective in treating said cancer solid tumor.

In one embodiment, the cancer is a solid tumor selected from the group consisting of basal cell cancer, medulloblastoma cancer, liver cancer, rhabdomyosarcoma, lung cancer, bone cancer, and pancreatic cancer.

The present invention also relates to a method for the treatment of abnormal cell growth in a mammal which comprises administering to said mammal an amount of a compound of Formula I or a pharmaceutically acceptable salt thereof that is effective in treating abnormal cell growth in combination with an anti-tumor agent selected from the group consisting of mitotic inhibitors, alkylating agents, antimetabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

The present invention also provides for a pharmaceutical composition comprising an effective amount of a compound of Formula I or a pharmaceutically acceptable salt thereof, and a pharmaceutically acceptable carrier.

The present invention provides a method for making a compound of Formula I comprising reacting a compound of formula D:

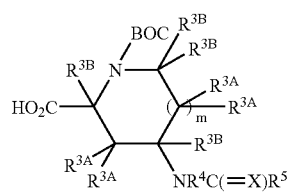

D with a substituted benzene-1,2-diamine in the presence of a coupling reagent resulting in the formation of a benzene-1,2-diamine mono amide which is then heated to about 100° C. in the presence of an acid such as acetic acid to form a compound of formula F:

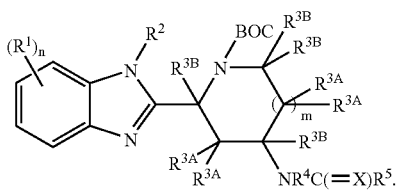

The present invention provides methods of preparing compounds of Formula I, comprising:

(a) treating a compound of Formula D,

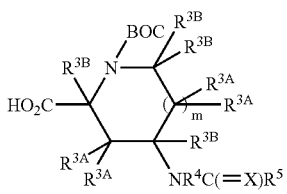

(b) with a 1,2-diamine to afford a compound of formula of formula F, and

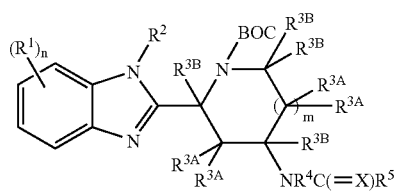

(c) deprotecting the compound of Formula F.

The present invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labelled compounds of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

The present invention also relates to the pharmaceutically acceptable acid addition salts of the compounds of the invention. The acids which are used to prepare the pharmaceutically acceptable acid addition salts of the aforementioned base compounds of this invention are those which form non toxic acid addition salts, i.e., salts containing pharmacologically acceptable anions, such as, but not limited to, the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of the compounds of the invention. The chemical bases that may be used as reagents to prepare pharmaceutically acceptable base salts of those compounds of the compounds of the invention that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

As used herein, the terms "compound of the invention" and "compounds of the invention" are meant to encompass pharmaceutically acceptable salts of said compounds.

As used herein, the phrases "compound of Formula I" and "compound of Formula I or a pharmaceutically acceptable salt thereof" includes solvates or hydrates thereof.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

This invention also encompasses pharmaceutical compositions containing prodrugs of compounds of the invention. Compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters that are covalently bonded to the above substituents of the compounds of the invention through the carbonyl carbon prodrug sidechain.

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The compounds of this invention include all stereoisomers (e.g., cis and trans isomers) and all optical isomers of compounds of the invention (e.g., R and S enantiomers), as well as racemic, diastereomeric and other mixtures of such isomers. While all stereoisomers are encompassed within the scope of our claims, one skilled in the art will recognize that particular stereoisomers may be preferred. For example, in the case where A is a piperidine ring and $R^{3A}$ and $R^{3B}$ are H, preferred compounds contain the R configuration at the 4 position wherein the —N($R^4$)C(=X)$R^5$ moiety is attached as shown below in the structure (i) (note that in ring A, the N atom is labeled as position 1, and the rest of the positions are numbered in a counterclockwise manner relative to position 1). The most preferred compounds when A is a piperdine ring have the R configuration at the point of attachment to the —N($R^4$)C(=X)$R^5$ moiety and the R configuration at point of attachment to the benzimidazole moiety as shown below in the structure (ii).

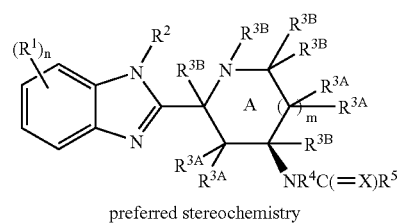

preferred stereochemistry (i)

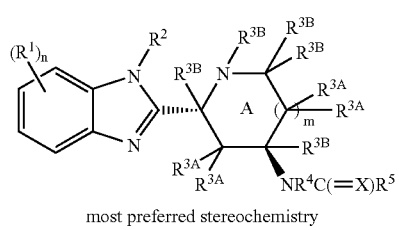

most preferred stereochemistry (ii)

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of the invention that can be separated into rotationally restricted isomers.

The term "2-amino-N-[(3R,5S)-5-[5-(phenylmethyl)-1H-benzimidazol-2-yl]-3-pyrrolidinyl]-acetamide" means a compound of the formula:

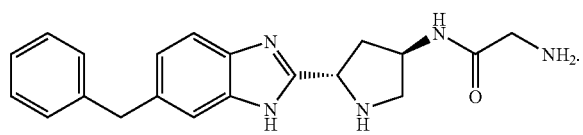

The term "($C_1$-$C_6$)alkyl", as used herein means saturated monovalent hydrocarbon radicals containing from one to six carbon atoms, having straight or branched moieties.

The terms "carbocycle", "carbocyclyl", "carbocyclo", "carbocyclic," or "($C_3$-$C_{12}$)carbocyclyl" as used herein means an aliphatic ring system having three to twelve members. The terms "carbocycle", "carbocyclyl", "carbocyclo", or "carbocyclic" whether saturated or partially unsaturated, also refers to rings that are optionally substituted. The terms also include aliphatic rings that are fused to one or more aromatic or non-aromatic rings, such as in a decahydronaphthyl or tetrahydronaphthyl, where the radical or point of attachment is on the aliphatic ring.

As used herein, the term "cycloalkyl" refers to a mono, fused or bridged bicyclic or tricyclic carbocyclic rings, (e.g., cyclopropyl, cyclobutyl, cyclopentyl, cyclohexyl, cycloheptyl, cyclopentenyl, cyclohexenyl, bicyclo[2.2.1]heptanyl, bicyclo[3.2.1]octanyl and bicyclo[5.2.0]nonanyl, norbornyl, adamantanyl, etc.); said rings may optionally containing 1 or 2 double bonds. The term "cycloalkyl" also includes spiro cycloalkyl groups, including, without limitation multi-ring systems joined by a single atom.

The term "alkoxy", as used herein means 0-alkyl groups wherein alkyl is as defined above.

The terms "hydroxyalkyl", "alkoxyalkyl", and alkoxycarbonyl", used alone or as part of a larger moiety includes both straight and branched chains containing one to six carbon atoms.

The term "alkenyl" used alone or as part of a larger moiety shall include both straight and branched chains containing two to ten carbon atoms having at least one carbon-carbon double bond. The terms "alkynyl" used alone or as part of a larger moiety shall include both straight and branched chains containing two to ten carbon atoms having at least one carbon-carbon triple bond.

The terms "haloalkyl", "haloalkenyl" and haloalkoxy" means alkyl, alkenyl or alkoxy, as the case may be, substituted with one or more halogen atoms. The term "halo" is used herein interchangeably with the term "halogen" means F, Cl, Br, or I. Preferred halo groups are F, Cl, and Br.

The term "heteroatom", means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 1 to 3 heteroatoms selected from oxygen, sulfur or nitrogen, the nitrogen may be N (as in 3,4-dihydro-2H-pyrrolyl), NH (as in pyrrolidinyl) or NOR (as in N-substituted pyrrolidinyl).

"Aryl" and "($C_6$-$C_{12}$)aryl" means aromatic radicals such as phenyl, naphthyl, tetrahydronaphthyl, indanyl and the like. The term also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl" as it is used herein, is a group in which an aromatic ring is fused to one or more non-aromatic rings, such as in an indanyl, phenanthridinyl, or tetrahydronaphthyl, where the radical or point of attachment is on the aromatic ring. The term "aryl" also refers to rings that are optionally substituted. The term "aryl" may be used interchangeably with the term "aryl ring."

The term "heterocycle", "heterocyclyl", or "heterocyclic" as used herein includes aromatic and non-aromatic ring systems having four to fourteen members, preferably five to ten, in which one or more ring carbons, preferably one to four, are each replaced by a heteroatom such as N, O, or S. Non-aromatic heterocyclic groups include groups having only 4 atoms in their ring system, but aromatic heterocyclic groups must have at least 5 atoms in their ring system. The heterocyclic groups include benzo-fused ring systems. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzo[1,3]dioxine, benzo[1,4]dioxine, benzopyrrolidinyl, benzopiperidinyl, benzoxolanyl, benzothiolanyl, 4,5,6,7-tetrahydropyrazol[1,5-alpha]pyridine and benzothianyl.

Also included within the scope of the term "heterocyclyl", or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring.

The term "heterocycle", "heterocyclyl", or "heterocyclic" whether saturated or partially unsaturated, also refers to rings that are optionally substituted.

An example of a 4 membered heterocyclic group is azetidinyl (derived from azetidine). An example of a 5 membered heterocyclic group is thiazolyl and an example of a 10 membered heterocyclic group is quinolinyl.

Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

An example of a heterocyclic group wherein 1 or 2 ring carbon atoms are substituted with oxo (=O) moieties is 1,1-dioxo-thiomorpholinyl, thienopyridinone, or pyrimidine-2,4-dione. An example of a heterocyclic group wherein 1 ring sulfur atom is substituted with 2 oxo (=O) moieties is tetrahydrothiophenedioxide.

Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2 5 pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl.

The term "heteroaryl" also refers to rings that are optionally substituted. The term "heteroaryl" may be used interchangeably with the term "heteroaryl ring" or the term "heteroaromatic." An aryl (including aralkyl, aralkoxy, aryloxyalkyl and the like) or heteroaryl (including heteroaralkyl and heteroarylalkoxy and the like) group may contain one or more $R^5$ substituents.

When preparing compounds of the invention in accordance with the invention, it is open to a person skilled in the art to routinely select the form of the intermediate compound which provides the best combination of features for this purpose. Such features include the melting point, solubility, processability and yield of the intermediate form and the resulting ease with which the product may be purified on isolation.

The invention also relates to methods for making intermediate compounds that are useful for making the compounds of the invention.

As noted above, invention also relates to the pharmaceutically acceptable salts of the compounds of the invention. Pharmaceutically acceptable salts of the compounds of the invention include the acid addition and base salts thereof. Suitable acid addition salts are formed from acids which form non-toxic salts. Non-limiting examples of suitable acid addition salts include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Non-limiting examples of suitable base salts include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art.

The compounds of the invention may also exist in unsolvated and solvated forms. Accordingly, the invention also relates to the hydrates and solvates of the compounds of the invention.

The term 'solvate' is used herein to describe a molecular complex comprising the compound of the invention and one or more pharmaceutically acceptable solvent molecules, for example, ethanol.

The term 'hydrate' is employed when said solvent is water. One embodiment of a hydrate is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985).

Some non-limiting examples of prodrugs in accordance with the invention include (i) where the compound of the invention contains a carboxylic acid functionality (—COOH), an ester thereof, for example, a compound wherein the hydrogen of the carboxylic acid functionality of the compound of Formula I is replaced by $(C_1-C_6)$alkyl;

(ii) where the compound of the invention contains an alcohol functionality (—OH), an ether thereof, for example, a compound wherein the hydrogen of the alcohol functionality of the compound of the invention is replaced by $(C_1-C_6)$ alkanoyloxymethyl; and (iii) where the compound of the invention contains a primary or secondary amino functionality (—$NH_2$ or —NHR where R≠H), an amide thereof, for example, a compound wherein, as the case may be, one or both hydrogens of the amino functionality of the compound of the invention is/are replaced by $(C_1-C_6)$alkanoyl.

Further examples of replacement groups in accordance with the foregoing examples and examples of other prodrug types may be found in the aforementioned references.

Moreover, certain compounds of the invention may themselves act as prodrugs of other compounds of the invention.

Also included within the scope of the invention are metabolites of compounds of the invention, that is, compounds formed in vivo upon administration of the drug. Some examples of metabolites in accordance with the invention include:

(i) where the compound of the invention contains a methyl group, an hydroxymethyl derivative thereof (e.g., —$CH_3$→—$CH_2OH$):

(ii) where the compound of the invention contains an alkoxy group, an hydroxy derivative thereof (e.g., —OH);

(iii) where the compound of the invention contains a tertiary amino group, a secondary amino derivative thereof;

(iv) where the compound of the invention contains a secondary amino group, a primary derivative thereof (e.g., —$NH_2$);

(v) where the compound of the invention contains a phenyl moiety, a phenol derivative thereof (e.g., -Ph→-PhOH); and (vi) where the compound of the invention contains an amide group, a carboxylic acid derivative thereof (e.g., —$CONH_2$→—COOH).

Compounds of the invention containing one or more asymmetric carbon atoms can exist as two or more stereoisomers. Where a compound of the invention contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

The compounds of the present invention may have asymmetric carbon atoms. The carbon-carbon bonds of the compounds of the present invention may be depicted herein using a solid line (-), a solid wedge (◢), or a dotted wedge (·▪▪▪▪). The use of a solid line to depict bonds from asymmetric carbon atoms is meant to indicate that all possible stereoisomers at that carbon atom are included. The use of either a solid or dotted wedge to depict bonds from asymmetric carbon atoms is meant to indicate that only the stereoisomer shown is meant to be included. It is possible that compounds of the invention may contain more than one asymmetric carbon atom. In those compounds, the use of a solid line to depict bonds from asymmetric carbon atoms is meant to indicate that all possible stereoisomers are meant to be included. The use of a solid line to depict bonds from one or more asymmetric carbon atoms in a compound of the invention and the use of a solid or dotted wedge to depict bonds from other asymmetric carbon atoms in the same compound is meant to indicate that a mixture of diastereomers is present.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer (s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of an alcoholic solvent such as isopropanol, typically from 2% to 20%, and from 0 to 5% by volume of an alkylamine, typically 0.1% diethylamine. Concentration of the eluate affords the enriched mixture.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The invention also relates to methods for the treatment of abnormal cell growth in a mammal. In one embodiment the invention relates to a method for the treatment of abnormal cell growth in a mammal comprising administering to said mammal an amount of a compound of the invention that is effective in treating abnormal cell growth.

In another embodiment the abnormal cell growth is cancer.

In another embodiment the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

The invention also relates to methods for the treatment of cancer solid tumors in a mammal. In one embodiment the invention relates to the treatment of cancer solid tumor in a mammal comprising administering to said mammal an amount of a compound of the invention that is effective in treating said cancer solid tumor.

In another embodiment the cancer solid tumor is breast, lung, colon, brain, prostate, stomach, pancreatic, ovarian, skin (melanoma), endocrine, uterine, testicular, or bladder.

In another embodiment the invention relates to a method for the treatment of abnormal cell growth in a mammal which comprises administering to said mammal an amount of a compound of the invention that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In one embodiment is provided a method of treating ectodermally-, mesodermally-, or endodermally-derived cancers.

In still another embodiment the invention relates to a pharmaceutical composition for the treatment of abnormal cell growth in a mammal comprising an amount of a compound of the invention that is effective in treating abnormal cell growth, and a pharmaceutically acceptable carrier.

DETAILED DESCRIPTION OF THE INVENTION

The compounds of the invention can be prepared by the following general methods and by methods described in detail in the Experimental Section.

Scheme 1

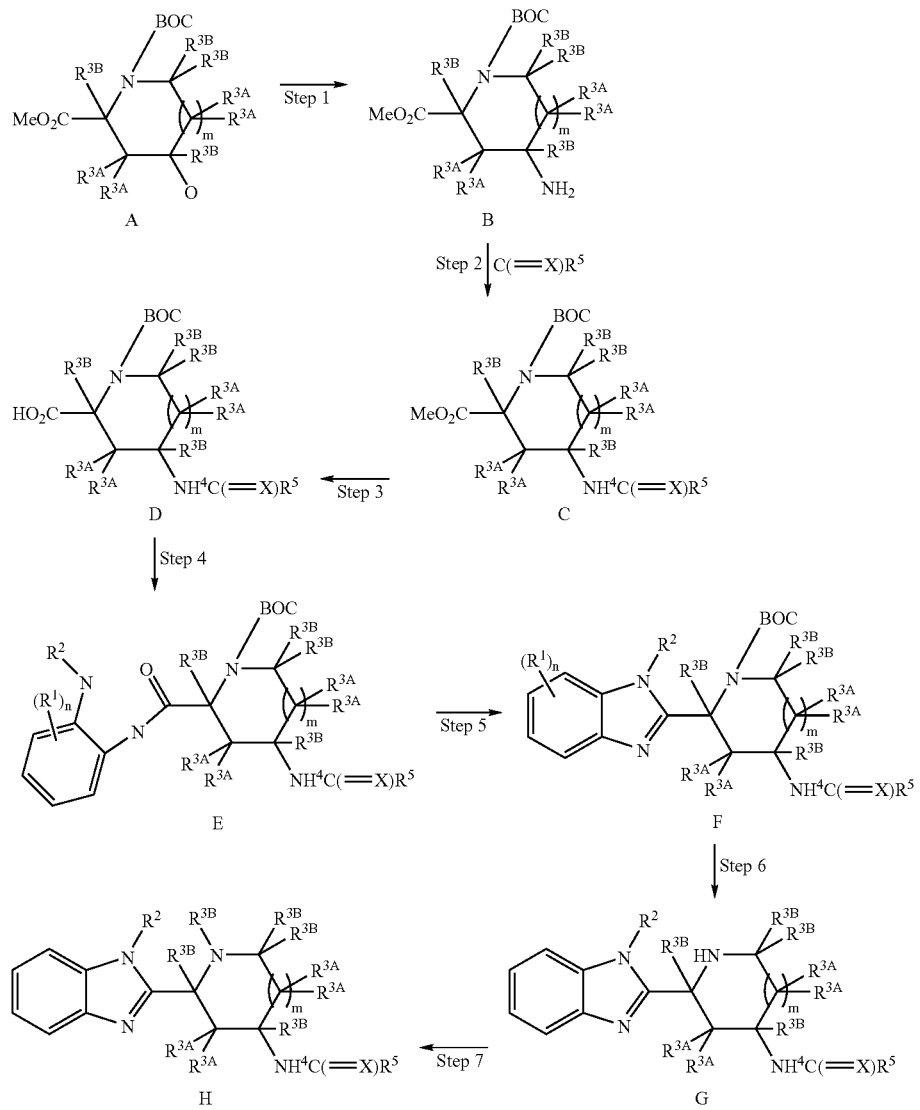

Compounds claimed herein can be prepared as described in Scheme 1. In Step 1, Compound A, substituted with a carboxylic acid ester and a protected amine, is reacted with mesylchloride to form the corresponding mesylate of the alcohol which is then displaced with sodium azide and subsequently reduced under hydrogenation or similar reductive conditions well known to one skilled in the art. One skilled in the art will recognize this transformation could alternatively be accomplished in several different routes such as oxidation of the alcohol to the ketone and subsequent reductive amination with a protected amine that is then deprotected. In Step 2 the amino group attached to Compound B can be reacted with, for example, an activated carboxylic acid, isocyanate or carbamoyl chloride to produce the compounds of compound C. The carboxylic acid may be activated as a carboxylic acid chloride, as a mixed anhydride, formed from, for example pivaloyl chloride or isopropylchloroformate, or as an active intermediate such as is formed by treatment of a carboxylic acid with coupling reagents such as N-(3-dimethylaminopropyl)-N'-ethylcarbodiimide hydrochloride, propylphosphonic acid anhydride, or other amide forming reagents well known to those skilled in the art. Step 2 is best performed in an aprotic solvent such as tetrahydrofuran, 1,4-dioxane or dimethylformamide and at a range of temperatures but generally from room temperature to about 80° C. In Step 3 the carboxylic ester can be deprotected by means known to one skilled in the art. For example, an ethyl ester could be saponified with lithium hydroxide, sodium hydroxide or potassium hydroxide in, for example, an alcoholic solvent such as ethanol or in a mixture of an organic solvent such as ethanol, methanol or tetrahydrofuran with water. The saponification could be performed at a range of temperatures but generally at from room temperature to about 80° C. In Step 4 the carboxylic acid of Compound D is reacted with a substituted benzene-1,2-diamine in the presence of a coupling reagent such as N-(3-dimethylaminopropyl)-N'-ethylcarbodiimide hydrochloride, propylphosphonic acid anhydride, or other amide forming reagents well known to those skilled in the art. Starting materials are commercially available, unless otherwise noted in the Examples. The reaction is best performed in an aprotic solvent such as tetrahydrofuran, 1,4-dioxane, dimethylformamide, or acetonitrile. The reaction can be performed at a range of temperatures but generally from room temperature to about 80° C. In Step 5 the resulting benzene-1,2-diamine mono amide can then be cyclized to form the benzimidazole ring by heating to about 100° C. in the presence of an acid such as acetic acid, or by treatment with additional portions of a coupling agent as described above. Subsequently in Step 6 the t-butoxycarbonyl protecting group is removed with hydrogen chloride in an appropriate solvent such as 1,4-dioxane, ethyl acetate or methylene chloride or with trifluoroacetic acid, neat or in an appropriate solvent such as methylene chloride. Step 6 can be performed at a range of temperatures but generally from about 0° C. to room temperature. One skilled in the art will recognize that although a t-butoxycarbonyl protecting group is shown in Scheme 1, the amine could be protected in alternate ways, such as with a benzyloxycarbonyl group, which would be removed by methods known to one skilled in the art. In Step 7 the amine of Compound G can be substituted by reacting with an aldehyde and reducing the resulting imine with a reducing agent such as sodium cyanoborohydride in a solvent such as methanol at temperatures ranging from about 0° C. to about 80° C. Alternative reducing agents such as sodium triacetoxyborohydride can be used as well as others know to one skilled in the art. Step 7 could also be accomplished by reacting Compound G with an alkylating agent such as methyl iodide with appropriate protection of reactive functionality in Compound G as would be known by one skilled in the art.

As an example, the synthesis of the free base of Example 31 is shown in Scheme 2 and is described is more detail below. Protected ester compound J, which is commercially available, is allowed to react with a mixture of methanesulfonyl chloride and 4-N,N-dimethylaminopyridine (DMAP) in pyridine to provide compound K. Compound K is then allowed to react with sodium azide in N,N-dimethylformamide (DMF) to provide azido compound L, which is then reduced using hydrogen and palladium on carbon to afford amino compound M. Reaction of compound M with 4-isocyanatobenzonitrile in tetrahydrofuran (THF) and in the presence of triethylamine affords urea derivative compound N. The ester in compound N was then saponified using lithium hydroxide in a mixture of THF, methanol, and water to afford the corresponding carboxylic acid compound O. Coupling of compound O with 1,2-phenylenediamine using benzotriazole-1-yl-oxy-tris-(dimethylamino)-phosphonium hexafluorophosphate (BOP) as a coupling agent and diisopropylethylamine (DIEA) was performed in DMF to provide amide compound P. Reaction of compound P first with acetic acid afforded a BOC-protected indole intermediate that was then allowed to react with trifluoroacetic acid to remove the BOC group. This further intermediate compound was then allowed to react with formaldehyde in the presence of sodium cyanoborohydride to afford final compound Q. Compound Q can be obtained in free base form or salt form according to methods known to those of ordinary skill in the art. Precursor compounds such as J, and corresponding stereoisomers, are commercially available or can be prepared according to methods known to those of skill in the art.

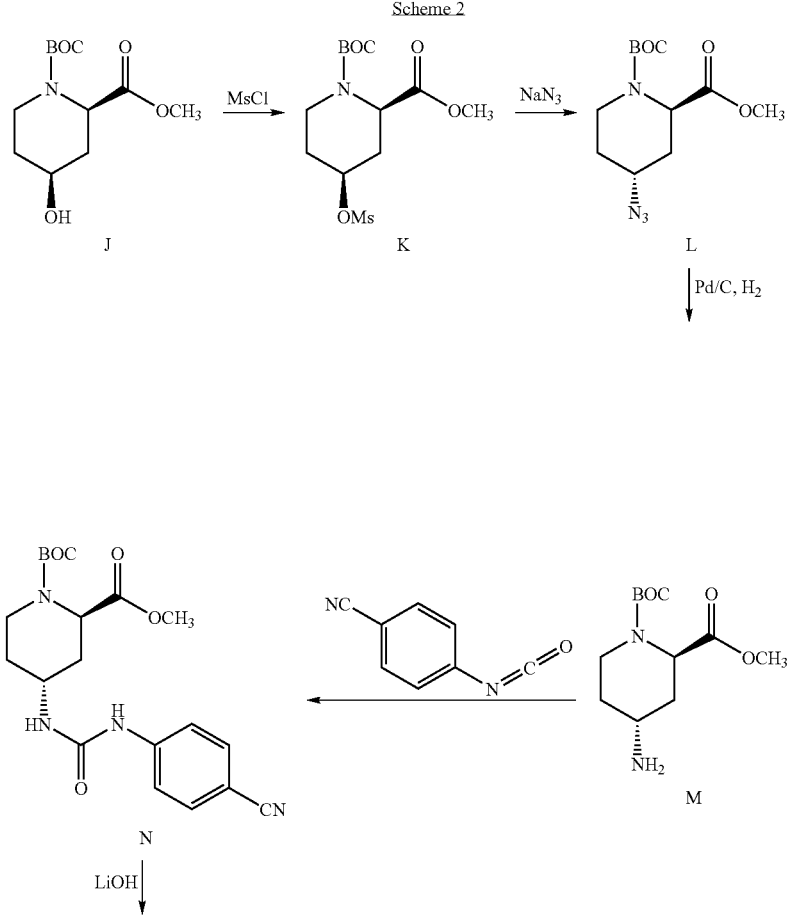

-continued

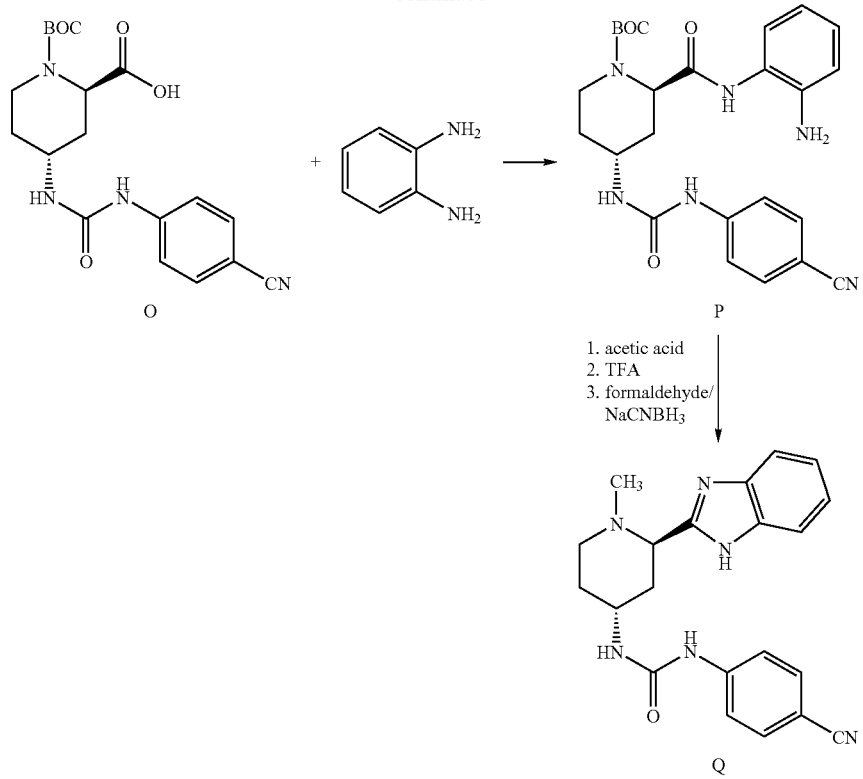

As noted above, the compounds of the invention are useful as inhibitors of SMO.

Methods for determining the in vitro activity of these compounds are described below:

Smoothened (SMO)/Sonic Hedgehog (SHh) Transient Transcriptional Activation Assay On Day 1, 2×106 C3H10T1/2 cells (ATCC # CCL-226) were split and seeded in 12 mL of growth medium Basal Medium Eagle (BME, Invitrogen #21010-046) supplemented with 2 mM L-glutamine (Invitrogen #25030-081), 0.1 units/mL penicillin and 0.1 μg/mL streptomycin (Invitrogen #15140-122), and 10% Fetal Bovine Serum (FBS, Invitrogen #16140-071) in a T-75 flask (Costar #3376). They were allowed to attach for 4 hours at 37° C., 5% $CO_2$. The cells were then transfected using Fugene 6 (Roch #11 814 443 001) in the following reaction: 48 μL Fugene 6 and 745 μL Opti-MEM (Invitrogen #31985-070) were mixed and allowed to sit at room temperature for 5 minutes. 8 μg of pGL4.14/mGli (CS) DNA (10× murine Gli response elements and minimal CS promoter) and 0.5 μg of pEGFP DNA (Clontech) were added, gently mixed and incubated at room temperature for 20 minutes. This entire transfection mix was then added to the T-75 flask containing the cells. The cells were incubated at 37° C., 5% $CO_2$ for 18-24 hours.

On Day 2, the transfected cells were trypsinized and seeded into white 96 well plates (Costar #3917) in 100 μL/well of growth medium at a concentration of 20,000 cells/well. The cells were allowed to recover for 4 hours before adding serum starvation medium Dulbecco's Modified Eagle Medium (DMEM, Invitrogen #21063-029) supplemented with 2 mM L-glutamine, 0.1 units/mL penicillin and 0.1 μg/mL streptomycin, and 0.5% Calf Serum (CS, Invitrogen #26170-043). The growth media was aspirated off, and the cells were rinsed with 100 μL of starvation media. 95 μL of starvation media was then added to each well. The cells were incubated for 20 hours at 37° C., 5% $CO_2$.

On Day 3, cells were dosed with test compounds at a final concentration ranging from 2 μM to 2 nM. Immediately after dosing cells with compounds, recombinant human sonic hedgehog (SHh, R&D Systems #1845-SH) was add to a final concentration of 250 ng/mL. A 25 μg vial of SHh was reconstituted with 250 μL PBS/0.1% BSA to give a 100 ng/μL working stock. This working stock was then diluted 1:20 in starvation media. The transfected cells were incubated with compounds and SHh for 20 hours at 37° C., 5% $CO_2$.

Luciferase assays were conducted on Day 4 using Dual-Glo Luciferase assay system (Promega #E2940) according to Promega's protocol. Briefly, Dual-Glo luciferase reagent was made up and 100 μL were added to each well of the 96 well plate containing media. Plates were shaken at room temperature for 10 minutes, and then read on TopCount (Perkin-Elmer). The luminescence was recorded.

This invention also relates to a method for the treatment of abnormal cell growth in a mammal, including a human, comprising administering to said mammal an amount of a compound of the invention, as defined above, or a pharmaceutically acceptable salt, solvate, hydrate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, multiple myeloma, cancer of the bladder, cancer of the kidney or urethra, renal cell carcinoma, carcinoma of the renal pelvis, neoplasms of the central nervous system (CNS), primary CNS lymphoma, spinal axis tumors, brain stem glioma, pituitary adenoma, medulloblastoma, or a combination of one or more of the foregoing cancers. In one embodiment the method comprises comprising administering to a mammal an amount of a compound of the invention that is effective in treating said cancer solid tumor. In one embodiment is provided a method of treating solid and liquid tumors in mammal, comprising administering to said mammal a compound or the invention that is effective in treating such tumors. In one embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

In another embodiment is provided a method for treating multiple myeloma in a mammal, comprising administering to said mammal an amount of a compound of the invention that effective in treating multiple myeloma.

This invention also relates to a method for the treatment of abnormal cell growth in a mammal which comprises administering to said mammal an amount of a compound of the invention, or a pharmaceutically acceptable salt, solvate, hydrate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the invention, as defined above, or a pharmaceutically acceptable salt, solvate, hydrate or prodrug thereof, that is effective in treating abnormal cell growth, and a pharmaceutically acceptable carrier. In one embodiment of said composition, said abnormal cell growth is cancer, including, but not limited to, basal cell carcinoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of the invention, or a pharmaceutically acceptable salt, solvate, hydrate or prodrug thereof, that is effective in treating abnormal cell growth in combination with another anti-tumor agent selected from the group consisting of antimetastatic agents, mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. The invention also contemplates a pharmaceutical composition for treating abnormal cell growth wherein the composition includes a compound of the invention, as defined above, or a pharmaceutically acceptable salt, solvate, hydrate or prodrug thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. In one embodiment is provided a method of treating abnormal cell growth in a mammal, comprising administering to said mammal an amount of a compound of the invention in combination with targeted therapies.

The invention also relates to a method of inhibiting stem cell production or stem cell renewal in a mammal, comprising administering a compound of the invention to said mammal in an amount that is effective to inhibit stem cell production or stem cell renewal.

The invention also relates to a method of treating erythroid and myeloid blood disorders in a mammal, comprising administering a compound of the invention to said mammal in an amount that is effective to treat such blood disorders.

This invention also relates to a method for the treatment of a disorder associated with angiogenesis in a mammal, including a human, comprising administering to said mammal an amount of a compound of the invention, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of the invention, or a pharmaceutically acceptable salt, solvate, hydrate or prodrug thereof, in combination with an amount of one or more substances selected from anti-angiogenesis agents, signal transduction inhibitors, and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of the invention in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:
3-[[4-(4-fluoro-phenoxy)-benzenesulfonyl]-(1-hydroxycarbamoyl-cyclopentyl)-amino]-propionic acid;
3-exo-3-[4-(4-fluoro-phenoxy)-benzenesulfonylamino]-8-oxa-bicyclo[3.2.1]octane-3-carboxylic acid hydroxyamide;
(2R,3R) 1-[4-(2-chloro-4-fluoro-benzyloxy)-benzenesulfonyl]-3-hydroxy-3-methyl-piperidine-2-carboxylic acid hydroxyamide;
4-[4-(4-fluoro-phenoxy)-benzenesulfonylamino]-tetrahydro-pyran-4-carboxylic acid hydroxyamide;
3-[[4-(4-fluoro-phenoxy)-benzenesulfonyl]-(1-hydroxycarbamoyl-cyclobutyl)-amino]-propionic acid;
4-[4-(4-chloro-phenoxy)-benzenesulfonylamino]-tetrahydro-pyran-4-carboxylic acid hydroxyamide;
3-[4-(4-chloro-phenoxy)-benzenesulfonylamino]-tetrahydro-pyran-3-carboxylic acid hydroxyamide;
(2R,3R)1-[4-(4-fluoro-2-methyl-benzyloxy)-benzenesulfonyl]-3-hydroxy-3-methyl-piperidine-2-carboxylic acid hydroxyamide;
3-[[4-(4-fluoro-phenoxy)-benzenesulfonyl]-(1-hydroxycarbamoyl-1-methyl-ethyl)-amino]-propionic acid;
3-[[4-(4-fluoro-phenoxy)-benzenesulfonyl]-(4-hydroxycarbamoyl-tetrahydro-pyran-4-yl)-amino]-propionic acid;
3-exo-3-[4-(4-chloro-phenoxy)-benzenesulfonylamino]-8-oxa-bicyclo[3.2.1]octane-3-carboxylic acid hydroxyamide;
3-endo-3-[4-(4-fluoro-phenoxy)-benzenesulfonylamino]-8-oxa-bicyclo[3.2.1]octane-3-carboxylic acid hydroxyamide; and
3-[4-(4-fluoro-phenoxy)-benzenesulfonylamino]-tetrahydro-furan-3-carboxylic acid hydroxyamide;
and pharmaceutically acceptable salts, solvates and prodrugs of said compounds.

VEGF inhibitors, for example, SU-11248, SU-5416 and SU-6668 (Pfizer Inc. of South San Francisco, Calif., USA), can also be combined with a compound of the invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Texas, USA) and 2B-1 (Chiron), may be administered in combination with a compound of the invention. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent applications: Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound of the invention may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

A compound of the invention may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds of the present invention may be used alone or in combination with one or more of a variety of anti-cancer agents or supportive care agents. For example, the compounds of the present invention may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. The invention also contemplates the use of the compounds of the present invention together with hormonal therapy, e.g., exemestane (Aromasin), Lupron, anastrozole (Arimidex), tamoxifen citrate (Nolvadex), Trelstar, and combinations thereof. Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds of the invention may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds of the invention.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin;

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid;

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin;

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof;

Plant derived anti-tumor substances include for example those selected from mitotic inhibitors, for example vinblastine, docetaxel (Taxotere) and paclitaxel;

Cytotoxic topoisomerase inhibiting agents include one or more agents selected from the group consisting of aclarubicin, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof;

Immunologicals include interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, Onco-VAX-CL, sargramostim, tasonermin, tecleukin, thymalasin, tositumomab, Virulizin, Z-100, epratuzumab, mitumomab, oregovomab, pemtumomab, Provenge;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex;

Other anticancer agents include alitretinoin, ampligen, atrasentan bexarotene, bortezomib. Bosentan, calcitriol, exisulind, finasteride, fotemustine, ibandronic acid, miltefosine, mitoxantrone, l-asparaginase, procarbazine, dacarbazine, hydroxycarbamide, pegaspargase, pentostatin, tazarotne, TLK-286, Velcade, Tarceva, or tretinoin;

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin;

Platinum-coordinated compounds include but are not limited to, cisplatin, carboplatin, nedaplatin, or oxaliplatin;

Camptothecin derivatives include but are not limited to camptothecin, 10-hydroxycamptothecin, 9-aminocamptothecin, irinotecan, SN-38, edotecarin, and topotecan;

Tyrosine kinase inhibitors are Iressa or SU5416;

Antibodies include Herceptin, Erbitux, Avastin, or Rituximab;

Interferons include interferon alpha, interferon alpha-2a, interferon, alpha-2b, interferon beta, interferon gamma-1a or interferon gamma-n1;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex; and Other antitumor agents include mitoxantrone, l-asparaginase, procarbazine, dacarbazine, hydroxycarbamide, pentostatin, or tretinoin.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The compounds of the present invention are potent inhibitors of SMO, and thus are all adapted to therapeutic use as antiproliferative agents (e.g., anticancer), antitumor (e.g., effective against solid tumors), antiangiogenesis (e.g., stop or prevent proliferationation of blood vessels) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

In one embodiment of the present invention cancer is selected from lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In another embodiment cancer is selected a solid tumor, such as, but not limited to, breast, lung, colon, brain (e.g., glioblastoma), prostate, stomach, pancreatic, ovarian, skin (melanoma), endocrine, uterine, testicular, and bladder.

The methods of the present invention include the use of small molecules which inhibit Smo, in the regulation of repair and/or functional performance of a wide range of cells, tissues and organs, including normal cells, tissues, and organs, as well as those having the phenotype of ptc loss-of-function, hedgehog gain-of-function, or smoothened gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells that are provided in culture (in vitro), or on cells in a whole animal (in vivo). See, for example, PCT publications WO 95/18856 and WO 96/17924.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The present invention also provides a pharmaceutical composition comprising a compound of Formula I, or a pharmaceutically acceptable salt or solvate thereof, as hereinbefore defined in association with a pharmaceutically acceptable adjuvant, diluent or carrier.

The invention further relates to a pharmaceutical composition of the invention which comprises mixing a compound of Formula I, or a pharmaceutically acceptable salt or solvate thereof, as hereinbefore defined with a pharmaceutically acceptable adjuvant, diluent or carrier.

In another embodiment is provided a method of using a compound of any of Formulae I, II(a), II(b), II(c), II(d), II(e), III(a), III(b), III(c), III(d), III(e), IV(a), IV(b), IV(c), IV(d), IV(e), V(a), V(b), V(c), V(d), V(e), VI(a), VI(b), VI(c), VI(d), VI(e), VII(a), VII(b), VII(c), VII(d), and VII(e), or a pharmaceutically acceptable salt thereof, in the preparation of a medicament for the treatment of cancer.

For the above-mentioned therapeutic uses the dosage administered will, of course, vary with the compound employed, the mode of administration, the treatment desired and the disorder indicated. The daily dosage of the compound of Formula I or a pharmaceutically acceptable salt may be in the range from 1 mg to 1 gram, preferably 1 mg to 250 mg, more preferably 10 mg to 100 mg.

The present invention also encompasses sustained release compositions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The active compound may be applied as a sole therapy or may involve one or more other anti-tumour substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example antiestrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Where HPLC chromatography is referred to in the preparations and examples below, the general conditions used, unless otherwise indicated, are as follows. The column used is a Polaris 5 C18-A column, 20×2.0 mm, with a 3.76 minute gradient elution starting at 95% A/5% B (A: 98% water, 2% acetonitrile, 0.01% formic acid; B: 100% acetonitrile, 0.005% formic acid) ending at 100% B with a 1.0 mL/min flow rate. Compounds were detected by UV absorption and electrospray mass ionization.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Example 1

N-((2R,4R)-1-methyl-2-(6-methyl-1H-benzo[d]imidazol-2-yl)piperidin-4-yl)-2,3-dihydrobenzo[b][1,4]dioxine-6-carboxamide

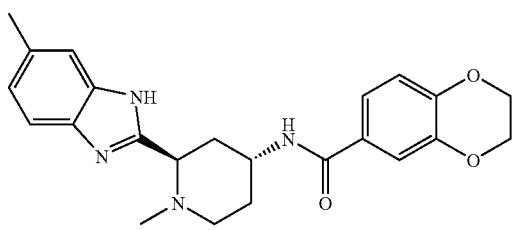

(2R,4S)-1-tert-butyl 2-methyl 4-(methylsulfonyloxy)piperidine-1,2-dicarboxylate (as described in F. Machetti, F. M. Cordero, F. De Sarlo, A. M. Papini, M. C. Alcaro, A. Brandi, Eur. J. Org. Chem. 2004, 2928-2935.)

MsCl (6.61 mL, 85 mmol) was added dropwise at 0° C. to a solution of (2R,4S)-1-tert-butyl 2-methyl 4-hydroxypiperidine-1,2-dicarboxylate (21 g, 81 mmol) and DMAP (100 mg, 0.81 mmol) in pyridine (50 mL). The mixture was stirred at room temperature for 5 hours and then was concentrated under reduced pressure to remove most solvent. Brine (200 mL) was added and extracted with ethyl acetate (2×200 mL). The organic layer was dried over MgSO₄, filtered and concentrated under reduced pressure to give title compound 26.7 g (98%) as colorless oil. LC-MS: 338.1 (t=1.9 min).

(2R,4R)-1-tert-butyl 2-methyl 4-azidopiperidine-1,2-dicarboxylate

NaN₃ (15.8 g, 243 mmol) was added to a solution of (2R,4S)-1-tert-butyl 2-methyl 4-(methylsulfonyloxy)piperidine-1,2-dicarboxylate (26.7 g, 81 mmol) in dry DMF (100 mL). The mixture was heated at 60° C. for 18 hours. Water (300 mL) was added to the reaction mixture and extracted with ethyl acetate/heptane (2:1) (2×200 mL). The combined organic layer was washed by brine and dried over MgSO₄, filtered and concentrated under reduced pressure to give a colorless oil 22.5 g (98%). LC-MS: 285.0 (t=2.5 min).

(2R,4R)-1-tert-butyl 2-methyl 4-aminopiperidine-1,2-dicarboxylate (2R,4R)-1-tert-butyl 2-methyl 4-azidopiperidine-1,2-dicarboxylate (22.5 g, 79 mmol) was dissolved in methanol (400 mL), Pd/C (10%, 6 g) was added, and the apparatus was flushed three times with N₂ and H₂. The reaction mixture was hydrogenated at a pressure of 50 psi at room temperature for 20 hours, filtered through Celite and rinsed with methanol and then concentrated under reduced pressure to give the amine as a colorless oil 20 g (96%). GC-MS: 258 (t=2.8 min).

(2R,4R)-1-tert-butyl 2-methyl 4-(2,3-dihydrobenzo[b][1,4]dioxine-6-carboxamido)piperidine-1,2-dicarboxylate BOP (6.59 g, 14.9 mmol) was added to a solution of 2,3-dihydrobenzo[b][1,4]dioxine-6-carboxylic acid (2.68 g, 14.9 mmol) and DIEA (5.3 mL, 30 mmol) in DMF (50 mL). Then (2R,4R)-1-tert-butyl 2-methyl 4-aminopiperidine-1,2-dicarboxylate (3.5 g, 13.5 mmol) was added to the mixture and the resulting solution was stirred at room temperature for 18 hours. Water (100 mL) was added to quench the reaction, and extracted with ethyl acetate (2×100 mL), organic layers were dried over MgSO₄, and concentrated under reduced pressure. The residue was purified by Companion (ReadySep, 120 g, silica gel packed) with ethyl acetate/heptane from 20-50% to give the amide as off-white solid 5.4 g (95%). LC-MC: 421.2 (t=2.4 min).

(2R,4R)-1-(tert-butoxycarbonyl)-4-(2,3-dihydrobenzo[b][1,4]dioxine-6-carboxamido)piperidine-2-carboxylic Acid LiOH (1.23 g, 51.4 mmol) was added to a solution of (2R,4R)-1-tert-butyl 2-methyl 4-(2,3-dihydrobenzo[b][1,4]dioxine-6-carboxamido)piperidine-1,2-dicarboxylate (5.4 g, 12.8 mmol) in THF/MeOH/water (3:2:1) (60 mL) and the resulting solution was stirred at room temperature for 18 hours. 1M HCl solution was added to reaction solution to adjust pH to about 3, extracted with ethyl acetate (2×100 mL). The organic layers were dried over MgSO₄ and concentrated to give the acid as a white solid 5.0 g (96%). LC-MS: 407.3; 405.3 (t=2.2 min).

(2R,4R)-tert-butyl 2-((2-amino-4-methylphenyl)carbamoyl)-4-(2,3-dihydrobenzo[b][1,4]dioxine-6-carboxamido)piperidine-1-carboxylate 4-Methylbenzene-1,2-diamine (1.65 g, 13.5 mmol) was added to a mixture of (2R,4R)-1-(tert-butoxycarbonyl)-4-(2,3-dihydrobenzo[b][1,4]dioxine-6-carboxamido)piperidine-2-carboxylic acid (5.0 g, 12 mmol), BOP (5.71 g, 12.9 mmol) and DIEA (4.3 mL, 24.6 mmol) in DMF (30 mL), and the resulting solution was stirred at room temperature for 8 hours. Water (100 mL) was added to the reaction mixture and then extracted with ethyl acetate (2×100 mL). The organic layers were dried over MgSO₄ and concentrated to give a red solid. Purification was done by Companion (ReadySep, 120 g, silica gel packed) with methanol/methylenechloride from 1-5% to give the title compound as a brown solid 4.85 g (80%). LC-MS: 511.2 (t=2.4 min).

N-((2R,4R)-1-methyl-2-(6-methyl-1H-benzo[d]imidazol-2-yl)piperidin-4-yl)-2,3-dihydrobenzo[b][1,4]dioxine-6-carboxamide The (2R,4R)-tert-butyl 2-((2-amino-4-methylphenyl)carbamoyl)-4-(2,3-dihydrobenzo[b][1,4]dioxine-6-carboxamido)piperidine-1-carboxylate (4.8 g, 9.4 mmol) was dissolved in acetic acid (10 mL) and stirred at 65° C. for 2 hours. The reaction mixture was concentrated under reduced pressure to remove acetic acid. Then TFA (10 mL) was added to the residue. The resulting solution was stirred at room temperature for 2 hours. The reaction mixture was concentrated to remove TFA and did next reaction without further purification. 37% formaldehyde solution (3.5 mL, 47 mmol) in water was added to a solution of the residue in methanol (50 mL) and the reaction mixture was stirred at room temperature for 1 hour, then 1M sodium cyanoborohydride in THF (29 mL) was added carefully at 0° C. The reaction mixture was stirred at room temperature for 18 hours and then solvent was evaporated in vacuum. Saturated sodium bicarbonate solution (100 mL) and ethyl acetate (200 mL) were added and the mixture was stirred about 30 minutes. The organic layer was separated, dried over MgSO₄, and concentrated. Product was purified by Companion (ReadySep 120 g, silica gel packed) with CH₃OH/CH₂Cl₂ from 2%-6-8% to give the title compound as an off-white solid 3.0 g (78%). LC-MS: 407.3, 405.3 (t=1.2 min).

Example 2

N-((2R,4R)-2-(1H-benzo[d]imidazol-2-yl)-1-cyclopropylpiperidin-4-yl)-2,3-dihydrobenzo[b][1,4]dioxine-6-carboxamide

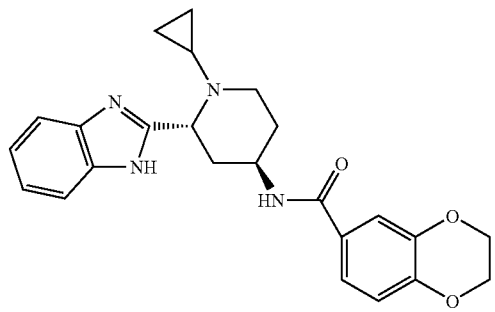

Acetic acid (0.075 mL, 1.3 mmol) was added to a solution of N-((2R,4R)-2-(1H-benzo[d]imidazol-2-yl)piperidin-4-yl)-2,3-dihydrobenzo[b][1,4]dioxine-6-carboxamide (50 mg, 0.13 mmol) in methanol (2 mL) and the then (1-ethoxy-cyclopropoxy)trimethylsilane (138 mg, 1.79 mmol) was added to the reaction solution and reaction mixture was stirred at room temperature for 10 min, then sodium cyanoborohydride (37 mg, 0.59 mmol) was added carefully.

The reaction mixture was stirred at 50° C. 24 hours. Saturated sodium bicarbonate solution (10 mL) and ethyl acetate (30 mL) were added. The organic layer was separated, dried over MgSO₄, and concentrated. Product was purified by Companion (ReadySep, 12 g, silica gel packed) with CH₃OH/CH₂Cl₂ from 1%-5% to give the named compound as a white solid 46 mg (85%). LC-MS: 419.2, 417.3 (t=1.7 min).

Example 3

1-((2R,4R)-2-(1H-benzo[d]imidazol-2-yl)-1-methylpiperidin-4-yl)-3-(6-(trifluoromethyl)pyridin-3-yl)urea

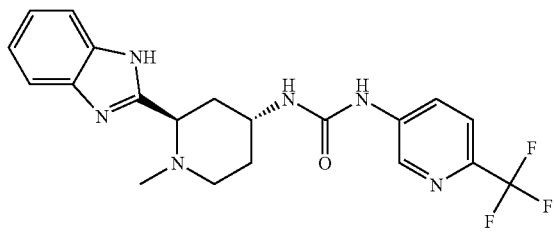

(2R,4R)-1-tert-butyl 2-methyl 4-(3-(6-(trifluoromethyl)pyridin-3-yl)ureido)piperidine-1,2-dicarboxylate

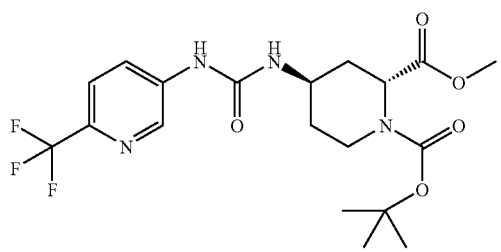

A solution of CDI (345 mg, 2.13 mmol) in THF (10 mL) was added to a solution of (2R,4R)-1-tert-butyl 2-methyl 4-aminopiperidine-1,2-dicarboxylate (500 mg, 1.94 mmol) in THF (15 mL) at room temperature. The reaction mixture was stirred at 70° C. for 3 hours. Then 6-(trifluoromethyl)pyridin-3-amine (345 mg, 2.13 mmol) was added to the mixture and the resulting solution was stirred at 60° C. for 24 hours. Water (50 mL) and ethyl acetate (50 mL) were added to the mixture. The organic layer was separated and dried over MgSO₄ and concentrated under reduced pressure. The purification was done by Companion (ReadySep, 40 g, silica gel packed) with ethyl acetate/heptane from 40-60% to give 10 as a white solid 550 mg (64%). LC-MS: 447.2, 445.3 (t=2.5 min).

(2R,4R)-1-(tert-butoxycarbonyl)-4-(3-(6-(trifluoromethyl)pyridin-3-yl)ureido)piperidine-2-carboxylic Acid LiOH (118 mg, 4.93 mmol) was added to a solution of (2R,4R)-1-tert-butyl 2-methyl 4-(3-(6-(trifluoromethyl)pyridin-3-yl)ureido)piperidine-1,2-dicarboxylate (550 mg, 1.23 mmol) in THF/MeOH/water (3:2:1) (24 mL) and the resulting solution was stirred at room temperature for 18 hours. 1M HCl solution was added to reaction solution to adjust the pH to about 3, extracted with ethyl acetate (2×50 mL). The organic layers were dried over MgSO₄ and concentrated to give the acid as a white solid 500 mg (94%). LC-MS: 433.2, 431.3; (t=2.1 min.)

(2R,4R)-tert-butyl 2-((2-aminophenyl)carbamoyl)-4-(3-(6-(trifluoromethyl)pyridin-3-yl)ureido)piperidine-1-carboxylate Benzene-1,2-diamine (131 mg, 1.21 mmol) was added to a mixture of (2R,4R)-1-(tert-butoxycarbonyl)-4-(3-(6-(trifluoromethyl)pyridin-3-yl)ureido)piperidine-2-carboxylic acid (500 mg, 1.16 mmol), BOP (563 mg, 1.27 mmol) and DIEA (0.403 mL, 2.31 mmol) in DMF (5 mL), and the resulting solution was stirred at room temperature for 8 hours. Water (20 mL) was added to the reaction mixture and then extracted with ethyl acetate (2×30 mL). The organic layers were dried over MgSO₄ and concentrated to give a red solid. Purification was done by Companion (ReadySep, 40 g, silica gel packed) with methanol/methylenechloride from 1-5% to give the title compound as a white solid 550 mg (91%). LC-MS: 523.3, 521.3; (t=2.3 min).

1-((2R,4R)-2-(1H-benzo[d]imidazol-2-yl)-1-methylpiperidin-4-yl)-3-(6-(trifluoromethyl)pyridin-3-yl)urea (2R,4R)-tert-butyl 2-((2-aminophenyl)carbamoyl)-4-(3-(6-(trifluoromethyl)pyridin-3-yl)ureido)piperidine-1-carboxylate (550 mg, 1.05 mmol) was dissolved in acetic acid (5 mL) and stirred at 65° C. for 2 hours. The reaction mixture was concentrated under reduced pressure to remove acetic acid. Then TFA (3 mL) was added to the residue. The resulting solution was stirred at room temperature for 2 hours. The reaction mixture was concentrated to remove TFA and did next reaction without further purification. 37% formaldehyde solution (0.25 mL, 3.2 mmol) in water was added to a solution of the residue in methanol (5 mL) and the reaction mixture was stirred at room temperature for 1 hour, then 1M sodium cyanoborohydride in THF (3.2mL, 3.2 mmol) was added carefully at 0° C. The reaction mixture was stirred at room temperature for 18 hours and then solvent was evaporated in vacuum. Saturated sodium bicarbonate solution (20 mL) and ethyl acetate (40 mL) were added and the mixture was stirred about 30 min. The organic layer was separated and dried over MgSO₄, and concentrated. Product was purified by Companion (ReadySep 40 g, silica gel packed) with CH₃OH/CH₂Cl₂ from 2%-6-8% to give the title compound as an off-white solid 270 mg (52%). LC-MS: 419.2, 417.3 (t=1.7 min).

Example 4

1-(4-cyanophenyl)-3-((2R,4R)-2-(5,6-dimethyl-1H-benzo[d]imidazol-2-yl)-1-methylpiperidin-4-yl)urea

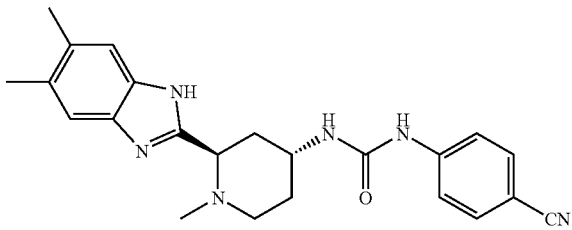

(2R,4R)-1-tert-butyl 2-methyl 4-(3-(4-cyanophenyl)ureido)piperidine-1,2-dicarboxylate

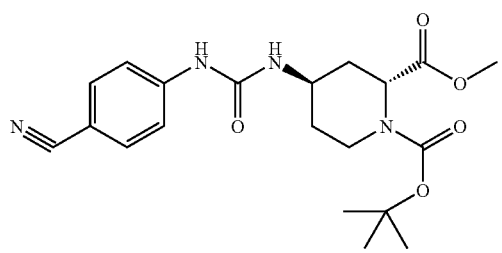

4-isocyanatobenzonitrile (1.17 g, 8.13 mmol) was added to a solution of (2R,4R)-1-tert-butyl 2-methyl 4-aminopiperidine-1,2-dicarboxylate (2.0 g, 7.7 mmol) and NEt₃ (1.3 mL, 9.3 mmol) in THF (30 mL), and the resulting solution was stirred at room temperature for 6 hours. 1M ammonia in methanol (5 mL) was added to reaction mixture to quench excess isocyanine. Water (100 mL) and ethyl acetate (200 mL) were added to the mixture. The organic layer was separated and dried over MgSO₄ and concentrated to give a solid. Purification was done by Companion (ReadySep, 80 g, silica gel packed) with ethyl acetate/heptane from 40-70% to give the urea as a white solid 2.9 g (90%). LC-MS: 403.2, 401.3 (t=2.6 min).

(2R,4R)-1-(tert-butoxycarbonyl)-4-(3-(4-cyanophenyl)ureido)piperidine-2-carboxylic Acid LiOH (143 mg, 5.96 mmol) was added to a solution of (2R,4R)-1-tert-butyl 2-methyl 4-(3-(4-cyanophenyl)ureido)piperidine-1,2-dicarboxylate (1200 mg, 2.98 mmol) in THF/MeOH/water (3:2:1) (24 mL) and the resulting solution was stirred at room temperature for 18 hours. 1M HCl solution was added to reaction solution to adjust pH to about 3, extracted with ethyl acetate (2×50 mL). The organic layers were dried over MgSO₄ and concentrated to give the acid as a white solid 1150 mg (99%). LC-MS: 389.2, 387.3 (t=2.1 min).

(2R,4R)-tert-butyl 2-((2-amino-4,5-dimethylphenyl)carbamoyl)-4-(3-(4-cyanophenyl)ureido)piperidine-1-carboxylate 4,5-dimethylbenzene-1,2-diamine (39 mg, 0.286 mmol) was added to a mixture of (2R,4R)-1-(tert-butoxycarbonyl)-4-(3-(4-cyanophenyl)ureido)piperidine-2-carboxylic acid (100 mg, 0.258 mmol), BOP (120 mg, 0.27 mmol) and DIEA (0.09 mL, 0.52 mmol) in DMF (1 mL), and the resulting solution was stirred at room temperature for 8 hours. Water (10 mL) was added to the reaction mixture and then extracted with ethyl acetate (2×20 mL). The organic layers were dried over MgSO₄ and concentrated to give a red solid. Purification was done by Companion (ReadySep, 12 g, silica gel packed) with ethyl acetate/heptane from 50-80% to give the title compound as a white solid 104 mg (80%). LC-MS: 507.3, 505.4 (t=2.4 min).

1-(4-cyanophenyl)-3-((2R,4R)-2-(5,6-dimethyl-1H-benzo[d]imidazol-2-yl)-1-methylpiperidin-4-yl)urea (2R,4R)-tert-butyl 2-((2-amino-4,5-dimethylphenyl)carbamoyl)-4-(3-(4-cyanophenyl)ureido)piperidine-1-carboxylate (104 mg, 0.205 mmol) was dissolved in acetic acid (1 mL) and stirred at 65° C. for 2 hours. The reaction mixture was concentrated under reduced pressure to remove acetic acid. Then TFA (1 mL) was added to the residue. The resulting solution was stirred at room temperature for 2 hours. The reaction mixture was concentrated to remove TFA and did next reaction without further purification. 37% formaldehyde solution (0.046 mL, 0.616 mmol) in water was added to a solution of the residue in methanol (2 mL) and the reaction mixture was stirred at room temperature for 1 hour, then 1M sodium cyanoborohydride in THF (0.62 mL, 0.62 mmol) was added carefully at 0° C. The reaction mixture was stirred at room temperature for 18 hours and then solvent was evaporated in vacuum. Saturated sodium bicarbonate solution (5 mL) and ethyl acetate (20 mL) were added and the mixture was stirred about 30 min. The organic layer was separated and dried over MgSO₄, and concentrated. Product was purified by Companion (ReadySep 12 g, silica gel packed) with CH₃OH/CH₂Cl₂ from 1-5% to give the title compound as an off-white solid 71 mg (73%). LC-MS: 403.3, 401.4 (t=1.8 min).

Example 5

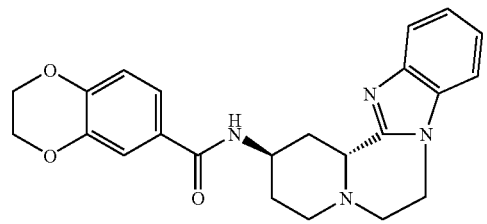

(2R,4R)-tert-butyl 4-(2,3-dihydrobenzo[b][1,4]dioxine-6-carboxamido)-2-(1-(2-(tetrahydro-2H-pyran-2-yloxy)ethyl)-1H-benzo[d]imidazol-2-yl)piperidine-1-carboxylate To a solution of (2R,4R)-tert-butyl 2-(1H-benzo[d]imidazol-2-yl)-4-(2,3-dihydrobenzo[b][1,4]dioxine-6-carboxamido)piperidine-1-carboxyl ate (200 mg, 0.418 mmol) in DMF (2 mL) was added 2-(2-bromoethoxy)-tetrahydro-2H-pyran (114 mg, 0.543 mmol) and K₂CO₃ (116 mg, 0.836 mmol), and the reaction mixture was stirred at 80° C. for over night. Water and ethyl acetate were added to the mixture, organic layer was separated and dried over MgSO4 and concentrated. The residue was purified by HPLC with 0.1% HCOOH in water/0.1% HCOOH in ACN from 45-70% to give the named compound as white solid 90 mg (35%). LC-MS: 607.2 (t=2.9 min).

(2R,4R)-tert-butyl 4-(2,3-dihydrobenzo[b][1,4]dioxine-6-carboxamido)-2-(1-(2-hydroxyethyl)-1H-benzo[d]imidazol-2-yl)piperidine-1-carboxylate (2R,4R)-tert-butyl 4-(2,3-dihydrobenzo[b][1,4]dioxine-6-carboxamido)-2-(1-(2-(tetrahydro-2H-pyran-2-yloxy)ethyl)-1H-benzo[d]imidazol-2-yl)piperidine-1-carboxylate (90 mg, 0.15 mmol) was added to a solution of acetic acid (2 mL), THF (1 mL) and water (0.5 mL) (4:2:1), the resulting solution was stirred at 45° C. for over night. The reaction mixture was concentrated to give a yellow oil as title compound (LC-MS: 523.2, t=2.3 min) for the next reaction without further purification.

(2R,4R)-tert-butyl 4-(2,3-dihydrobenzo[b][1,4]dioxine-6-carboxamido)-2-(1-(2-(methylsulfonyloxy)ethyl)-1H-benzo[d]imidazol-2-yl)piperidine-1-carboxylate Methanesulfonyl chloride (51.3 mg, 0.448 mmol) was added to a solution of (2R,4R)-tert-butyl 4-(2,3-dihydrobenzo[b][1,4]dioxine-6-carboxamido)-2-(1-(2-hydroxyethyl)-1H-benzo[d]imidazol-2-yl)piperidine-1-carboxylate (78 mg, 0.15 mmol) and DMAP (3.5 mg) in pyridine (1 mL) at 0° C. and the resulting mixture was stirred at room temperature for 5 hours. Water and ethyl acetate were added to the reaction mixture. The organic layer was separated and dried over MgSO4 and concentrated to give a yellow solid, which was purified by Companion (ReadSep, 12 g, silica gel packed) with ethyl acetate/heptane from 30-70% to give title compound as a white solid 65 mg (73%). LC-MS: 601.1 (t=2.6 min).

(2R,4R)-tert-butyl 4-(2,3-dihydrobenzo[b][1,4]dioxine-6-carboxamido)-2-(1-(2-(tetrahydro-2H-pyran-2-yloxy)ethyl)-1H-benzo[d]imidazol-2-yl)piperidine-1-carboxylate (2R,4R)-tert-butyl 4-(2,3-dihydrobenzo[b][1,4]dioxine-6-carboxamido)-2-(1-(2-(methylsulfonyloxy)ethyl)-1H-benzo[d]imidazol-2-yl)piperidine-1-carboxylate (65 mg, 0.11 mmol) was dissolved in TFA (1 mL) and stirred at room temperature for 2 hours. The reaction mixture was concentrated to removed TFA, the residue was dissolved in DMF (1 mL) and K2CO3 (30m g, 0.22 mmol) was added to it, the resulting mixture was stirred at 60° C. for over night. Water and ethyl acetate were added to reaction mixture, the organic layer was separated and dried over MgSO4 and concentrated. Purification was done by Companion (ReadSep, 12 g, silica gel packed) with CH3OH/CH2Cl2 from 1-5% to give a white solid 30 mg (60%) as title compound. LC-MS: 405.2 (t=1.4 min).

Free Base of Example 31

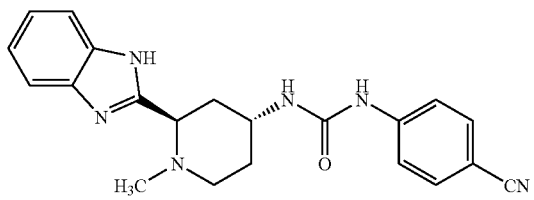

(2R,4R)-1-tert-butyl 2-methyl 4-(3-(4-cyanophenyl)ureido)piperidine-1,2-dicarboxylate

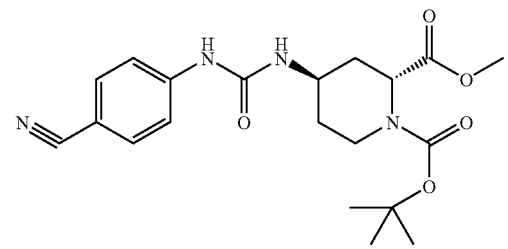

4-isocyanatobenzonitrile (1.17 g, 8.13 mmol) was added to a solution of (2R,4R)-1-tert-butyl 2-methyl 4-aminopiperidine-1,2-dicarboxylate (2.0 g, 7.7 mmol) and NEt3 (1.3 mL, 9.3 mmol) in THF (30 mL), and the resulting solution was stirred at room temperature for 6 hours. 1M ammonia in methanol (5 mL) was then added to the reaction mixture to quench excess isocyanine. Water (100 mL) and ethyl acetate (200 mL) were added to the mixture. The organic layer was separated and dried over MgSO4 and concentrated to give a solid. Purification by Companion (ReadySep, 80 g, silica gel packed) using ethyl acetate/heptane from 40-70% as eluent provided the title compound as a white solid 2.9 g (90%). LC-MS: 403.2, 401.3 (t=2.6 min).

(2R,4R)-1-(tert-butoxycarbonyl)-4-(3-(4-cyanophenyl)ureido)piperidine-2-carboxylic Acid

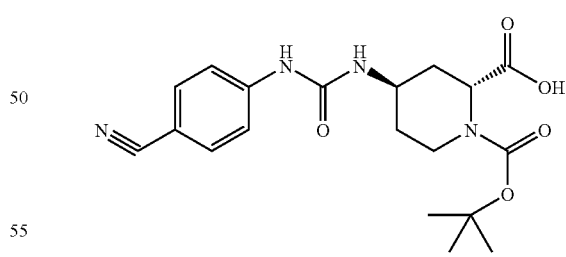

LiOH (143 mg, 5.96 mmol) was added to a solution of (2R,4R)-1-tert-butyl 2-methyl 4-(3-(4-cyanophenyl)ureido)piperidine-1,2-dicarboxylate (1200 mg, 2.98 mmol) in THF/MeOH/water (3:2:1) (24 mL) and the resulting solution was stirred at room temperature for 18 hours. 1M HCl solution was added to reaction solution to adjust the pH to about 3, the mixture was then extracted with ethyl acetate (2×150 mL), and the combined organic layers were dried over MgSO4 and concentrated to give the acid as a white solid 1150 mg (99%). LC-MS: 389.2, 387.3 (t=2.1 min).

89

(2R,4R)-tert-butyl 2-((2-amino-phenyl)carbamoyl)-4-(3-(4-cyanophenyl)ureido)piperidine-1-carboxylate

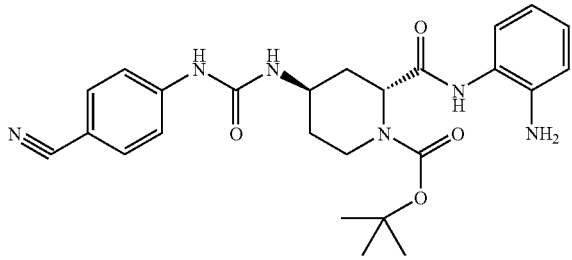

Benzene-1,2-diamine (365 mg, 3.38 mmol) was added to a mixture of (2R,4R)-1-(tert-butoxycarbonyl)-4-(3-(4-cyanophenyl)ureido)piperidine-2-carboxylic acid (1400 mg, 3.60 mmol), BOP (1600 mg, 3.6 mmol) and DIEA (1.2 mL, 6.9 mmol) in DMF (20 mL), and the resulting solution was stirred at room temperature for 8 hours. Water (100 mL) was added to the reaction mixture and it was then extracted with ethyl acetate (2×200 mL). The organic layers were dried over MgSO$_4$ and concentrated to give a red solid. Further purification by Companion (ReadySep, 80 g, silica gel packed) using ethyl acetate/heptane from 50-80% as eluent provided the title compound as a white solid 1600 mg (93%). LC-MS: 479.1, 477.2 (t=2.3 min).

90

1-[(2R,4R)-2-(1H-benzimidazol-2-yl)-1-methylpiperidin-4-yl]-3-(4-cyanophenyl)urea (2R,4R)-tert-butyl 2-((2-amino-phenyl)carbamoyl)-4-(3-(4-cyanophenyl)ureido)piperidine-1-carboxylate (1600 mg, 3.34 mmol) was dissolved in acetic acid (10 mL) and stirred at 65° C. for 2 hours. The reaction mixture was concentrated under reduced pressure to remove acetic acid. Trifluoroacetic acid (10 mL) was added to the residue. The resulting solution was stirred at room temperature for 2 hours. The reaction mixture was concentrated to remove TFA and the resulting product was used in the next step without further purification. 37% formaldehyde solution (1.24 mL, 16.7 mmol) in water was added to a solution of the residue in methanol (20 mL) and the reaction mixture was stirred at room temperature for 1 hour, then 1M sodium cyanoborohydride in THF (10.5 mL, 10.5 mmol) was added at 0° C. The reaction mixture was stirred at room temperature for 18 hours and the solvent was evaporated under vacuum. Saturated sodium bicarbonate solution (50 mL), water (100 mL) and ethyl acetate (200 mL) were added and the mixture was stirred about 30 min. The organic layer was separated, dried over MgSO$_4$, and concentrated. The resulting product was purified by Companion (ReadySep 40 g, silica gel packed) using CH$_3$OH/CH$_2$Cl$_2$ from 1-5% as eluent to provide the title compound as an off-white solid 915 mg (73%). LC-MS: 375.3, 373.3 (t=1.5 min). $^1$H NMR (acetone-D6): δ 1.81 (m, 2H), 1.9-2.05 (m, 2H), 2.10 (m, 1H), 2.17 (s, 3H), 2.52 (m, 1H), 2.94 (m, 1H), 3.86 (m, 1H), 4.2 (m, 1H), 6.4 (d, 1H), 7.16 (m, 2H), 7.52 (m, 2H), 7.60 (m, 2H), 7.62 (m, 2H), 8.46 (s, 1H).

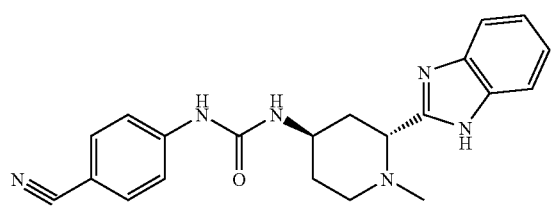

Examples listed in the following table were prepared using procedures analogous to those described above. In the following table, the structures are shown; if a salt is associated it is identified in the "Compound Name" column.

| COMPOUND EX. # NAME | STRUCTURE | SMO CELL % INHIBITION @ 2 μM | ANALYTICAL DATA | EX# PREP |
|---|---|---|---|---|
| 6 2,3-Dihydro-benzo[1,4]dioxine-6-carboxylic acid [1-methyl-2-(6-methyl-1H-benzoimidazol-2-yl)-piperidin-4-yl]-amide hydrochloride | | 105.26 | (acetone-D6) δ 1.97 (m, 2H), 2.16 (m, 5H), 2.40 (s, 3H), 2.62 (m, 1H), 2.92 (m, 1H), 3.90 (m, 1H), 4.24 (m, 4H), 4.41 (m, 1H), 6.8 (m, 1H), 6.97 (m, 1H), 7.16 (s, 1H), 7.40 (m, 3H), 7.52 (d, 1H); HPLC Rt = 1.2 MS: [M + H] = 407.3 | 1 |

| EX. # | COMPOUND NAME | STRUCTURE | SMO CELL % INHIBITION @ 2 μM | ANALYTICAL DATA | EX# PREP |
|---|---|---|---|---|---|
| 7 | 1-(4-cyanophenyl)-3-{(2R,4R)-1-methyl-2-[5-(trifluoromethyl)-1H-benzimidazol-2-yl]piperidin-4-yl}urea hydrochloride | 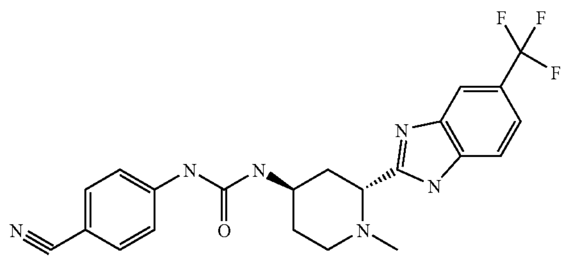 | 109.08 | HPLC Rt = 2.0 MS: [M + H] = 443.2 | 4 |
| 8 | tert-butyl (2S,4S)-2-(1H-benzimidazol-2-yl)-4-[({[4-chloro-3-(trifluoromethyl)phenyl]amino}carbonyl)amino]pyrrolidine-1-carboxylate | 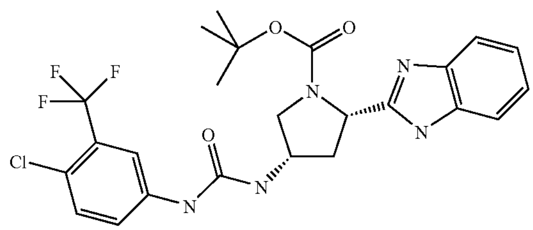 | 57.10 | (CD₃OD) δ 1.42 (s, 9H), 2.54 (m, 1H), 2.88 (m, 1H), 3.58 (m, 1H), 3.64 (m, 1H), 4.58 (m, 1H), 5.25 (m, 1H), 7.21-7.30 (m, 4H), 7.35-7.45 (m, 3H), 7.60 (d, 2H), 7.70 (d, 1H) HPLC Rt = 2.62 MS: [M + H] = 524.4 | 4 |
| 9 | N-[(3S,5S)-5-(1H-benzimidazol-2-yl)pyrrolidin-3-yl]-2,3-dihydro-1,4-benzodioxine-6-carboxamide | 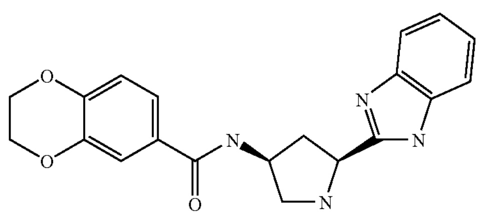 | 65.00 | HPLC Rt = 1.4 MS: [M + H] = 365 | 1 |
| 10 | benzyl (2S,4S)-2-(1H-benzimidazol-2-yl)-4-[(2,3-dihydro-1,4-benzodioxin-6-ylcarbonyl)amino]pyrrolidine-1-carboxylate | 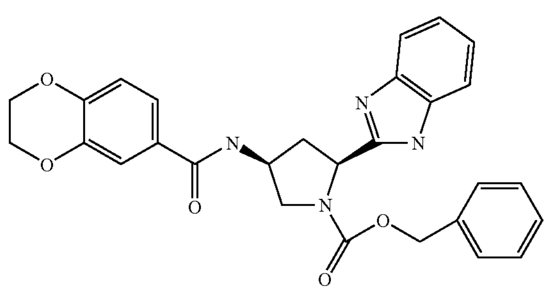 | 106.29 | HPLC Rt = 2.34 MS: [M + H] = 499.3 | 1 |
| 11 | N-[(3S,5S)-5-(1H-benzimidazol-2-yl)pyrrolidin-3-yl]-2,3-dihydro-1,4-benzodioxine-6-carboxamide | 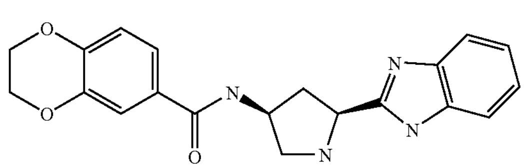 | 110.10 | HPLC Rt = 1.67 MS: [M + H] = 365.2 | 1 |

| EX. # | COMPOUND NAME | STRUCTURE | SMO CELL % INHIBITION @ 2 μM | ANALYTICAL DATA | EX# PREP |
|---|---|---|---|---|---|
| 12 | N-[(2R,13bR)-1,3,4,6,7,13b-hexahydro-2H-pyrido[2',1':3,4]pyrazino[1,2-a]benzimidazol-2-yl]-2,3-dihydro-1,4-benzodioxine-6-carboxamide hydrochloride | 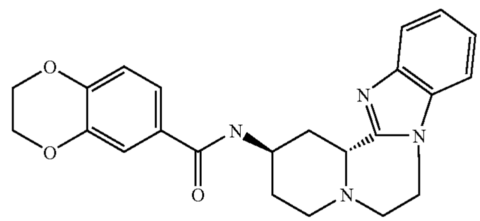 | 64.10 | (CD₃OD) δ 1.97 (m, 1H), 2.11 (m, 2H), 2.8 (m, 1H), 2.85 (d, 1H), 2.92 (m, 1H), 3.20 (dd, 1H), 3.70 (d, 3H), 4.06 (m, 1H), 4.18 (m, 1H), 4.2 (m, 4H), 4.38 (m, 1H), 6.42 (d, 1H), 6.85 (d, 1H), 7.20-7.40 (m, 5H), 7.68 (m, 1H) HPLC Rt = 1.4 MS: [M + H] = 405.2 | 5 |
| 13 | 1-[4-chloro-3-(trifluoromethyl)phenyl]-3-[(3S,5S)-5-(6-fluoro-1H-benzimidazol-2-yl)pyrrolidin-3-yl]urea | 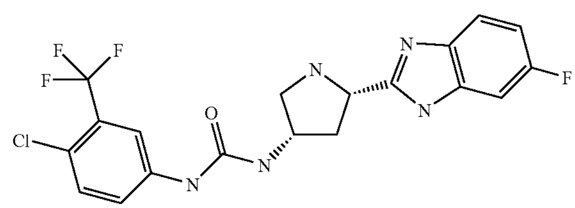 | 84.20 | HPLC Rt = 2.3 MS: [M + H] = 442.2 | 4 |
| 14 | 1-[4-chloro-3-(trifluoromethyl)phenyl]-3-[(3R,5S)-5-(6-fluoro-1H-benzimidazol-2-yl)-1-methylpyrrolidin-3-yl]urea | 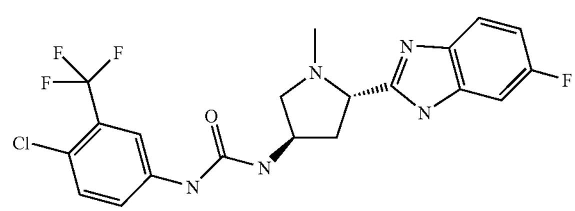 | 81.80 | HPLC Rt = 2.2 MS: [M + H] = 456 | 4 |
| 15 | 1-[(2R,4R)-2-(1H-benzimidazol-2-yl)-1-methylpiperidin-4-yl]-3-[4-(trifluoromethoxy)phenyl]urea hydrochloride | 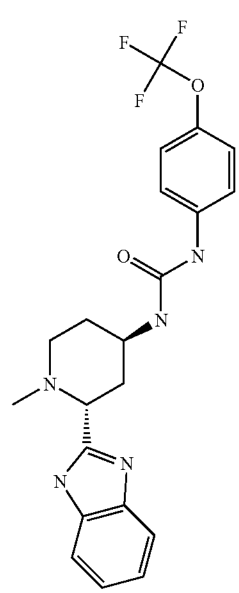 | 111.40 | HPLC Rt = 2 MS: [M + H] = 434.1 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 16 | 1-[(2R,4R)-2-(1H-benzimidazol-2-yl)-1-methylpiperidin-4-yl]-3-pyridin-4-ylurea hydrochloride | 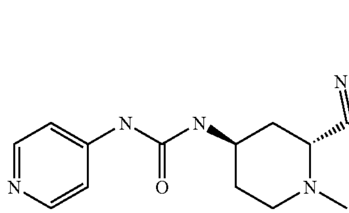 | 110.60 | HPLC Rt = 1.5 MS: [M + H] = 351.2 | 3 |
| 17 | 1-[4-chloro-3-(trifluoromethyl)phenyl]-3-[(3R,5S)-1-methyl-5-(6-methyl-1H-benzimidazol-2-yl)pyrrolidin-3-yl]urea | 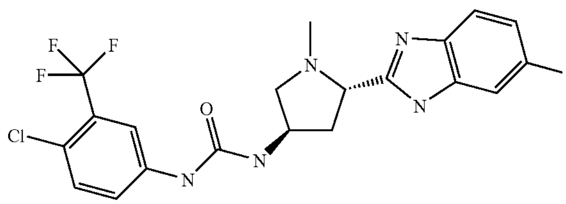 | 63.20 | HPLC Rt = 2.3 MS: [M + H]]= 452 | 4 |
| 18 | 1-[(2R,4R)-2-(1H-benzimidazol-2-yl)-1-methylpiperidin-4-yl]-3-[4-(trifluoromethyl)phenyl]urea hydrochloride | 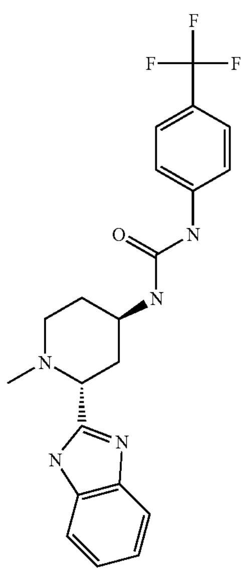 | 109.90 | HPLC Rt = 1.8 MS: [M + H] = 418.1 | 4 |
| 19 | 1-[(2R,4R)-2-(5-cyano-1H-benzimidazol-2-yl)-1-methylpiperidin-4-yl]-3-(4-cyanophenyl)urea hydrochloride | 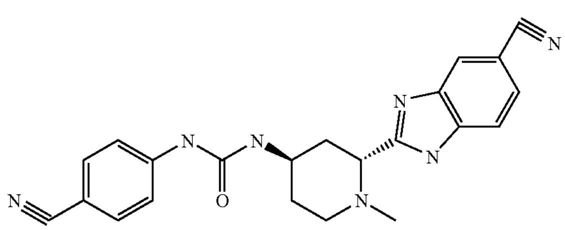 | 109.48 | HPLC Rt = 1.6 MS: [M + H] = 400.2 | 4 |
| 20 | 1-[4-chloro-3-(trifluoromethyl)phenyl]-3-[(3S,5S)-5-(6-methoxy-1H-benzimidazol-2-yl)pyrrolidin-3-yl]urea | 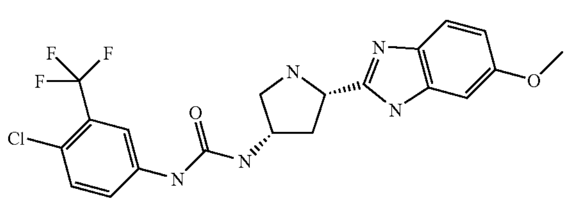 | 63.00 | HPLC Rt = 2.13 MS: [M + H] = 454 | 4 |

| EX. # | COMPOUND NAME | STRUCTURE | SMO CELL % INHIBITION @ 2 μM | ANALYTICAL DATA | EX# PREP |
|---|---|---|---|---|---|
| 21 | N-[(3S,5S)-5-(1H-benzimidazol-2-yl)-1-methylpyrrolidin-3-yl]-2,3-dihydro-1,4-benzodioxine-6-carboxamide | 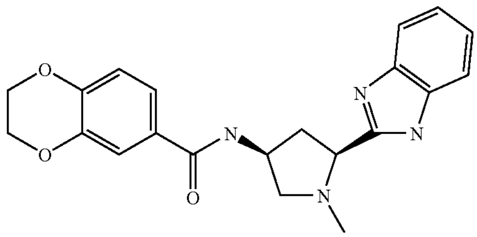 | 61.80 | (CD$_3$OD) δ 2.10 (m, 1H), 2.18 (s, 3H), 2.78 (m, 1H), 2.82 (m, 1H), 3.10 (d, 1H), 3.82 (m, 1H), 4.10 (m, 4H), 4.78 (m, 1H), 6.80 (d, 1H), 7.21 (m, 3H), 7.38 (m, 1H), 7.42 (s, 2H), 7.55 (b, 1H), 8.3 (d, 1H) HPLC Rt = 1.64 MS: [M + H] = 379.2 | 1 |
| 22 | 1-[4-chloro-3-(trifluoromethyl)phenyl]-3-[(3S,5S)-1-methyl-5-(6-methyl-1H-benzimidazol-2-yl)pyrrolidin-3-yl]urea | 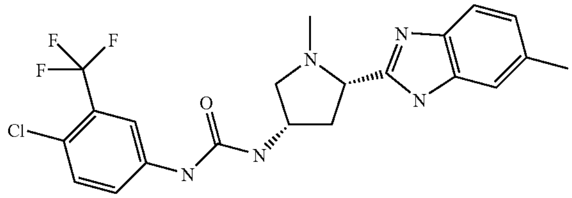 | 101.87 | HPLC Rt = 2.3 MS: [M + H] = 452 | 4 |
| 23 | 1-[4-chloro-3-(trifluoromethyl)phenyl]-3-[(3R,5S)-1-isopropyl-5-(6-methyl-1H-benzimidazol-2-yl)pyrrolidin-3-yl]urea | 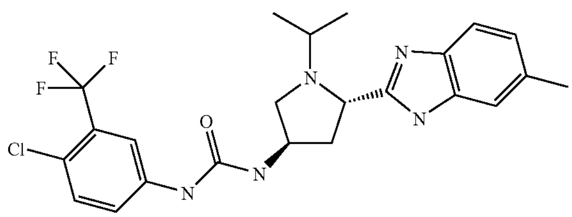 | 100.50 | HPLC Rt = 2.4 MS: [M + H]] = 480 | 4 |
| 24 | tert-butyl (2S,4R)-2-(1H-benzimidazol-2-yl)-4-[({[4-chloro-3-(trifluoromethyl)phenyl]amino}carbonyl)amino]pyrrolidine-1-carboxylate | 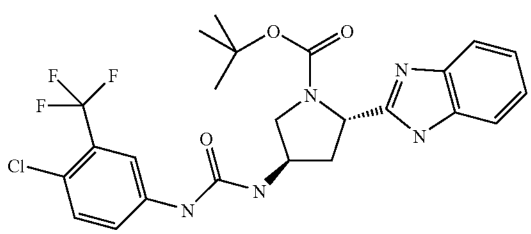 | 63.10 | HPLC Rt = 2.4 MS: [M + H] = 524 | 4 |
| 25 | 1-[4-chloro-3-(trifluoromethyl)phenyl]-3-[(3S,5S)-5-(6-methoxy-1H-benzimidazol-2-yl)-1-methylpyrrolidin-3-yl]urea | 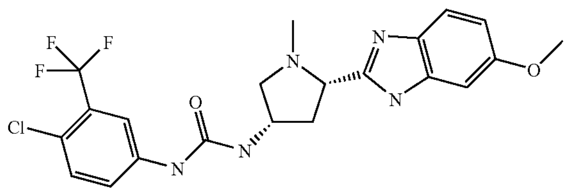 | 105.02 | HPLC Rt = 2.3 MS: [M + H] = 468 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 26 | 1-[(2R,4R)-2-(1H-benzimidazol-2-yl)-1-methylpiperidin-4-yl]-3-[4-chloro-3-(trifluoromethyl)phenyl]urea hydrochloride | 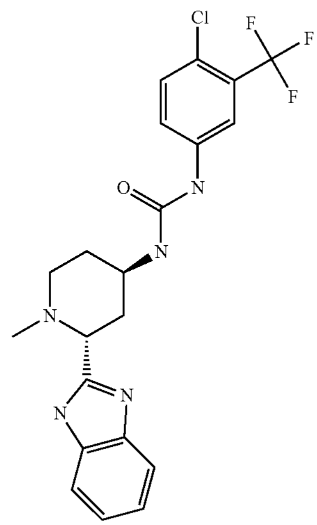 | 108.61 | HPLC Rt = 2.0 MS: [M + H] = 452 | 4 |
| 27 | N-{(2R,4R)-2-[5-(dimethylamino)-1H-benzimidazol-2-yl]-1-methylpiperidin-4-yl}-2,3-dihydro-1,4-benzodioxine-6-carboxamide hydrochloride | 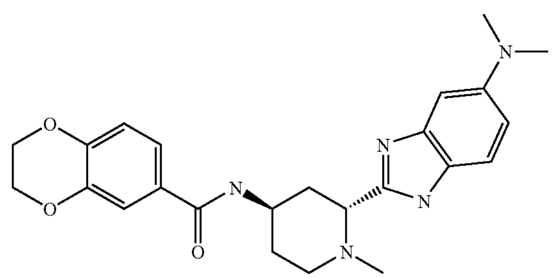 | 108.32 | HPLC Rt = 1.3 MS: [M + H] = 436.1 | 1 |
| 28 | 1-[(2R,4R)-2-(1H-benzimidazol-2-yl)-1-methylpiperidin-4-yl]-3-(3,5-dichlorophenyl)urea hydrochloride | 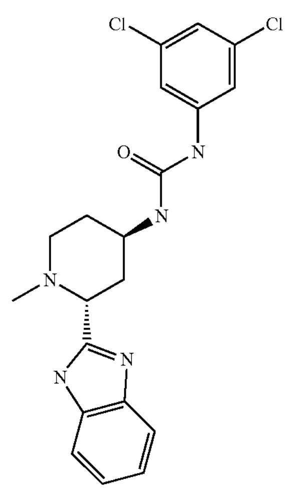 | 108.16 | HPLC Rt = 2.0 MS: [M + H] = 418 | 4 |
| 29 | 1-(4-cyanophenyl)-3-[(2R,4R)-2-(5-methoxy-1H-benzimidazol-2-yl)-1-methylpiperidin-4-yl]urea hydrochloride | 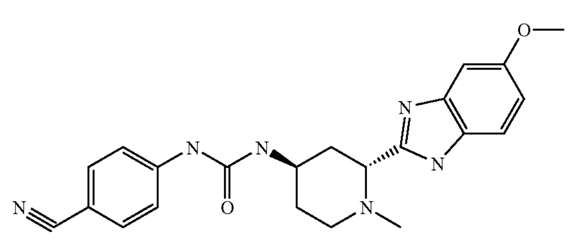 | 108.08 | HPLC Rt = 1.6 MS: [M + H]= 405.3 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 30 | 1-[(2R,4R)-2-(1H-benzimidazol-2-yl)-1-methylpiperidin-4-yl]-3-(4-chlorophenyl)urea hydrochloride | 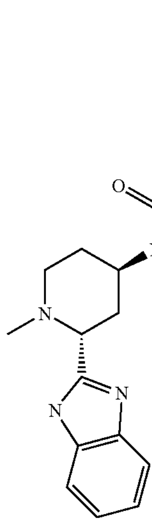 | 107.88 | HPLC Rt = 1.8 MS: [M + H] = 384.1 | 4 |
| 31 | 1-[(2R,4R)-2-(1H-benzimidazol-2-yl)-1-methylpiperidin-4-yl]-3-(4-cyanophenyl)urea hydrochloride | 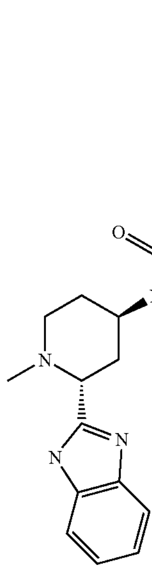 | 107.27 | (acetone-D6) δ 1.81 (m, 2H), 1.9-2.05 (m, 2H), 2.10 (m, 1H), 2.17 (s, 3H), 2.52 (m, 1H), 2.94 (m, 1H), 3.86 (m, 1H), 4.2 (m, 1H), 6.4 (d, 1H), 7.16 (m, 2H), 7.52 (m, 2H), 7.60 (m, 2H), 7.62 (m, 2H), 8.46 (s, 1H) HPLC Rt = 1.3 MS: [M + H] = 375.4 | 4 |
| 32 | 1-[(2R,4R)-2-(1H-benzimidazol-2-yl)-1-methylpiperidin-4-yl]-3-(6-fluoropyridin-3-yl)urea hydrochloride | 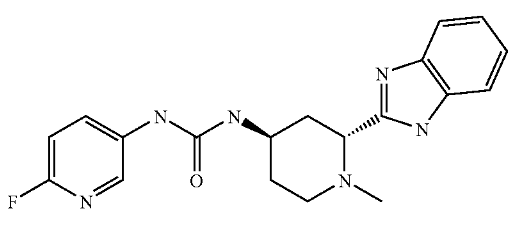 | 107.12 | HPLC Rt = 1.8 MS: [M + H] = 369.2 | 3 |
| 33 | N-[(2R,4R)-2-(1H-benzimidazol-2-yl)-1-methylpiperidin-4-yl]chromane-6-carboxamide hydrochloride | 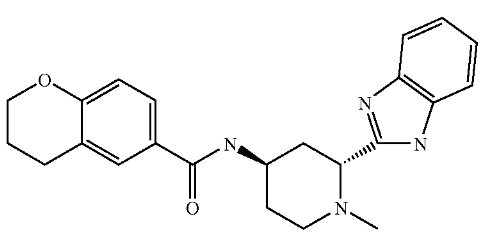 | 114.00 | HPLC Rt = 1.6 MS: [M + H] = 391.3 | 1 |

| EX. # | COMPOUND NAME | STRUCTURE | SMO CELL % INHIBITION @ 2 μM | ANALYTICAL DATA | EX# PREP |
|---|---|---|---|---|---|
| 34 | N-[(2R,4R)-2-(6-chloro-1H-benzimidazol-2-yl)-1-methylpiperidin-4-yl]-2,3-dihydro-1,4-benzodioxine-6-carboxamide hydrochloride | 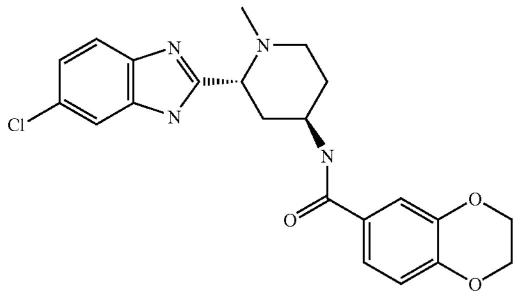 | 107.04 | HPLC Rt = 1.7 MS: [M + H] = 427.2 | 1 |
| 35 | 1-{(2R,4R)-1-methyl-2-[5-(trifluoromethyl)-1H-benzimidazol-2-yl]piperidin-4-yl}-3-[6-(trifluoromethyl)pyridin-3-yl]urea hydrochloride | 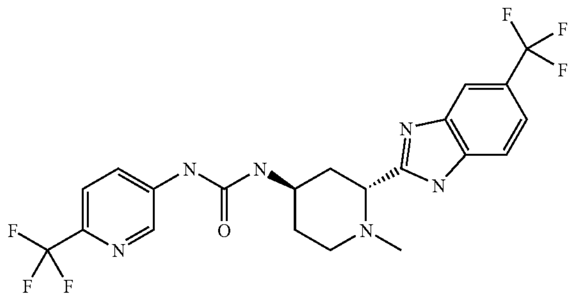 | 106.98 | HPLC Rt = 2.2 MS: [M + H] = 487.2 | 3 |
| 36 | 1-(4-cyanophenyl)-3-[(2R,4R)-1-methyl-2-(5-methyl-1H-benzimidazol-2-yl)piperidin-4-yl]urea hydrochloride | 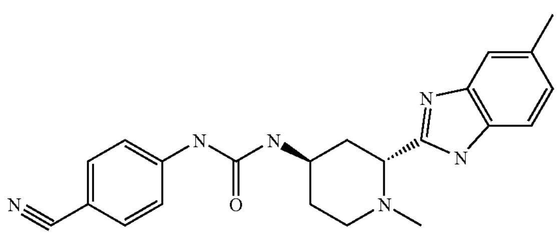 | 106.56 | HPLC Rt = 1.6 MS: [M + H] = 389.3 | 4 |
| 37 | 1-[(2R,4R)-2-(1H-benzimidazol-2-yl)-1-methylpiperidin-4-yl]-3-(4-methoxyphenyl)urea hydrochloride | 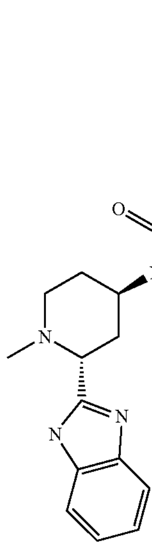 | 106.48 | HPLC Rt = 1.8 MS: [M + H] = 380.1 | 4 |

| EX. # | COMPOUND NAME | STRUCTURE | SMO CELL % INHIBITION @ 2 μM | ANALYTICAL DATA | EX# PREP |
|---|---|---|---|---|---|
| 38 | N-[(2R,4R)-2-(6-methoxy-1H-benzimidazol-2-yl)-1-methylpiperidin-4-yl]-2,3-dihydro-1,4-benzodioxine-6-carboxamide hydrochloride | 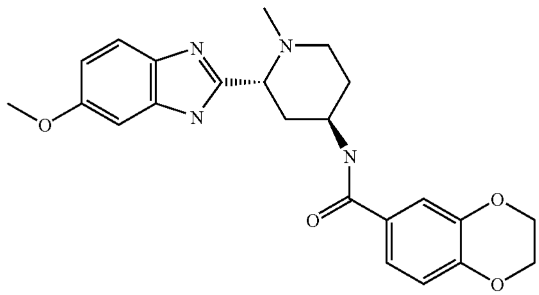 | 106.03 | (CD$_3$OD) δ 1.97 (m, 2H), 2.11 (m, 2H), 2.1 (s, 3H), 2.42 (m, 1H), 2.92 (m, 1H), 3.70 (m, 1H), 3.80 (s, 3H), 4.24 (m, 4H), 4.38 (m, 1H), 6.24 (d, 1H), 6.85 (m, 2H), 7.0 (b, 1H), 7.12 (m, 2H), 7.15 (s, 1H), 7.4 (b, 1H) HPLC Rt = 1.3 MS: [M + H] = 423.3 | 1 |
| 39 | 1-[(2R,4R)-2-(1H-benzimidazol-2-yl)-1-isobutylpiperidin-4-yl]-3-(4-cyanophenyl)urea | 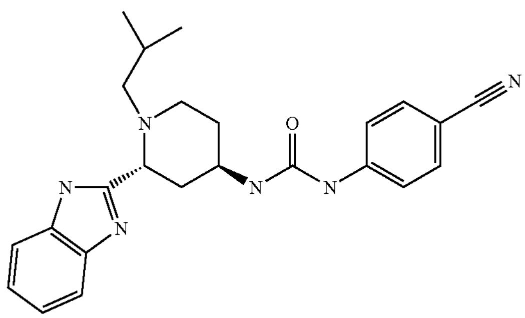 | 105.90 | 1H NMR (CD$_3$OD, 400 MHz) δ 0.73 (d, 3H), 0.82 (d, 3H), 1.75 (m, 1H), 1.82 (m, 1H), 1.92 (m, 1H), 2.00 (m, 1H), 2.04 (m, 1H), 2.10 (m, 1H), 2.20 (m, 1H), 2.38 (m, 1H), 3.10 (m, 1H), 3.79 (m, 1H), 4.08 (m, 1H), 7.21 (dd, 2H), 7.50-7.60 (m, 4H), 7.62 (d, 2H); HPLC Rt = 2.6 MS: [M + H] = 417 | 4 |
| 40 | 1-[(2R,4R)-2-(1H-benzimidazol-2-yl)-1-methylpiperidin-4-yl]-3-(6-fluoro-5-methylpyridin-3-yl)urea hydrochloride | 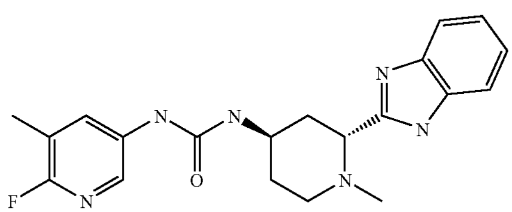 | 105.85 | HPLC Rt = 1.3 MS: [M + H] = 383.3 | 3 |
| 41 | 1-[(2R,4R)-2-(1H-benzimidazol-2-yl)-1-methylpiperidin-4-yl]-3-(6-fluoro-4H-1,3-benzodioxin-8-yl)urea hydrochloride | 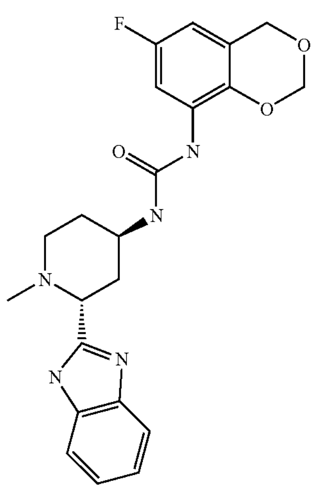 | 105.81 | HPLC Rt = 1.5 MS: [M + H] = 426.3 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 42 | N-[(2S,4R)-2-(1H-benzimidazol-2-yl)-1-methylpiperidin-4-yl]-2,3-dihydro-1,4-benzodioxine-6-carboxamide hydrochloride | 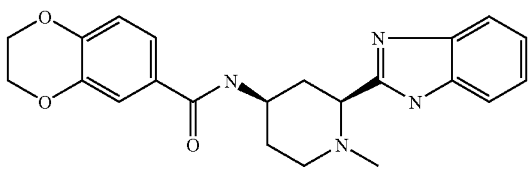 | 105.67 | HPLC Rt = 1.5 MS: [M + H] = 393 | 1 |
| 43 | 1-[(2R,4R)-2-(1H-benzimidazol-2-yl)-1-methylpiperidin-4-yl]-3-(5-cyanopyridin-2-yl)urea hydrochloride | 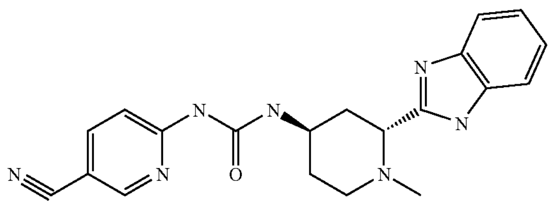 | 105.51 | HPLC Rt = 2.0 MS: [M + H] = 376.2 | 3 |
| 44 | N-[(2R,4R)-2-(1H-benzimidazol-2-yl)-1-ethylpiperidin-4-yl]-2,3-dihydro-1,4-benzodioxine-6-carboxamide hydrochloride | 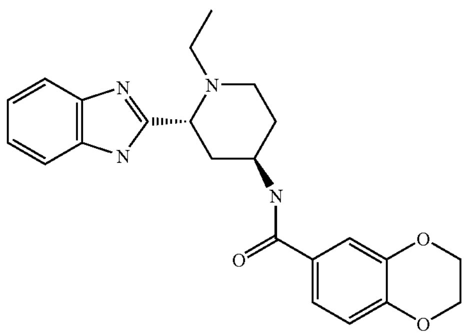 | 105.48 | HPLC Rt = 1.5 MS: [M + H] = 407.2 | 1 |
| 45 | N-[(2R,4R)-2-(6-fluoro-1H-benzimidazol-2-yl)-1-methylpiperidin-4-yl]-2,3-dihydro-1,4-benzodioxine-6-carboxamide hydrochloride | 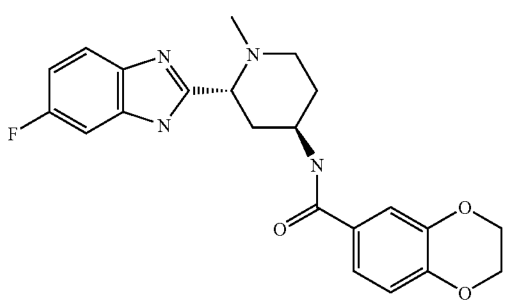 | 105.47 | (CD$_3$OD) δ 1.97 (m, 2H), 2.15 (m, 2H), 2.2 (s, 3H), 2.46 (m, 1H), 2.92 (m, 1H), 3.70 (m, 1H), 4.24 (m, 4H), 4.38 (m, 1H), 6.24 (d, 1H), 6.85 (m, 1H), 7.0 (m, 1H), 7.22 (m, 2H), 7.3 (s, 1H), 7.4 (b, 1H) HPLC Rt = 1.41 MS: [M + H] = 411.3 | 1 |
| 46 | 1-[(2R,4R)-2-(1H-benzimidazol-2-yl)-1-ethylpiperidin-4-yl]-3-(4-cyanophenyl)urea | 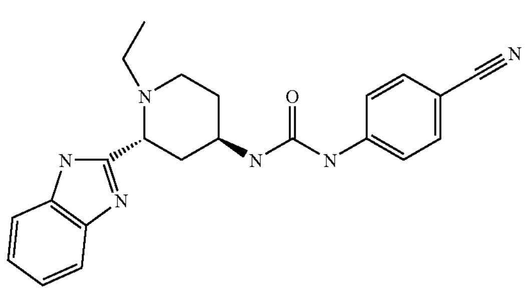 | 105.42 | $^1$H NMR (CD$_3$OD, 400 MHz) δ 1.04 (t, 3H), 1.86 (m, 1H), 2.04 (m, 2H), 2.14 (m, 1H), 2.27 (m, 1H), 2.49 (m, 2H), 3.14 (m, 1H), 3.90 (m, 1H), 4.11 (m, 1H), 7.21 (dd, 2H), 7.49-7.62 (m, 6H); HPLC Rt = 2.5 MS: [M + H] = 389 | 4 |

| EX. # | COMPOUND NAME | STRUCTURE | SMO CELL % INHIBITION @ 2 μM | ANALYTICAL DATA | EX# PREP |
|---|---|---|---|---|---|
| 47 | N-[(2R,4R)-2-(1H-benzimidazol-2-yl)-1-methylpiperidin-4-yl]-2,3-dihydro-1-benzofuran-5-carboxamide hydrochloride | 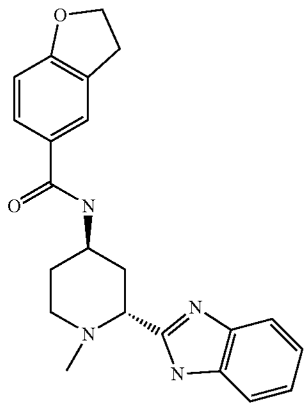 | 105.41 | HPLC Rt = 1.31 MS: [M + H] = 377.3 | 1 |
| 48 | 1-[(2R,4R)-2-(1H-benzimidazol-2-yl)-1-methylpiperidin-4-yl]-3-(2,6-dimethylpyridin-3-yl)urea hydrochloride | 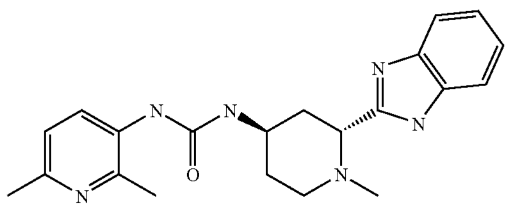 | 105.32 | HPLC Rt = 1.5 MS: [M + H] = 379.3 | 3 |
| 49 | N-[(2R,4R)-2-(5,6-dimethyl-1H-benzimidazol-2-yl)-1-methylpiperidin-4-yl]-2,3-dihydro-1,4-benzodioxine-6-carboxamide hydrochloride | 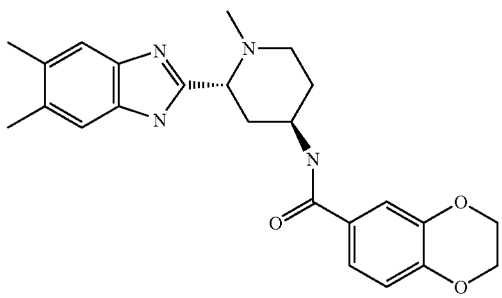 | 105.29 | HPLC Rt = 1.5 MS: [M + H] = 421.3 | 1 |
| 50 | 4-acetyl-N-[(2R,4R)-2-(1H-benzimidazol-2-yl)-1-methylpiperidin-4-yl]-3,5-dimethyl-1H-pyrrole-2-carboxamide hydrochloride | 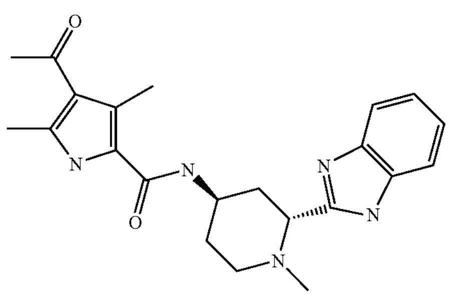 | 105.07 | HPLC Rt = 1.3 MS: [M + H] = 394.3 | 1 |
| 51 | 1-(4-cyanophenyl)-3-[(2R,4R)-2-(5-fluoro-1H-benzimidazol-2-yl)-1-methylpiperidin-4-yl]urea hydrochloride | 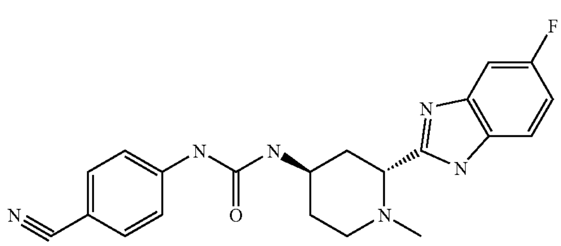 | 105.02 | HPLC Rt = 1.6 MS: [M + H] = 393.2 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 52 | 1-(4-cyanophenyl)-3-[(2R,4R)-2-(5,6-dimethyl-1H-benzimidazol-2-yl)-1-methylpiperidin-4-yl]urea hydrochloride | 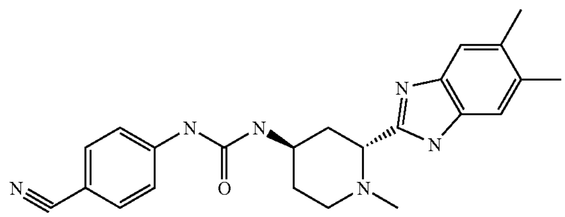 | 104.97 | HPLC Rt = 1.8 MS: [M + H] = 403.3 | 4 |
| 53 | 1-[(2R,4R)-2-(1H-benzimidazol-2-yl)-1-methylpiperidin-4-yl]-3-(4-isopropylphenyl)urea hydrochloride | 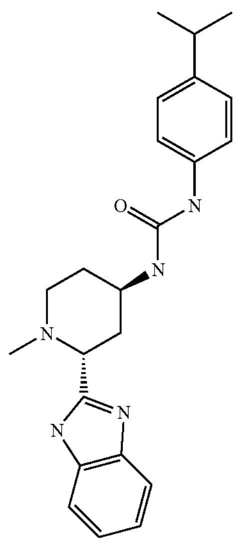 | 104.80 | HPLC Rt = 2.1 MS: [M + H] = 392.4 | 4 |
| 54 | 1-[(2R,4R)-2-(1H-benzimidazol-2-yl)-1-methylpiperidin-4-yl]-3-(6-cyanopyridin-3-yl)urea hydrochloride | 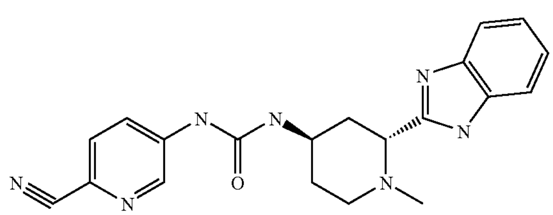 | 104.76 | HPLC Rt = 1.3 MS: [M + H] = 376.2 | 4 |
| 55 | 1-[(2R,4R)-2-(5-cyano-1H-benzimidazol-2-yl)-1-methylpiperidin-4-yl]-3-[6-(trifluoromethyl)pyridin-3-yl]urea hydrochloride | 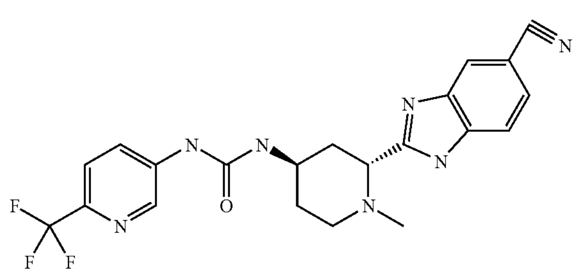 | 104.54 | HPLC Rt = 1.8 MS: [M + H] = 444.2 | 3 |

-continued

| EX. # | COMPOUND NAME | STRUCTURE | SMO CELL % INHIBITION @ 2 μM | ANALYTICAL DATA | EX# PREP |
|---|---|---|---|---|---|
| 56 | 1-[(2R,4R)-2-(1H-benzimidazol-2-yl)-1-methylpiperidin-4-yl]-3-[4-(dimethylamino)phenyl]urea hydrochloride | 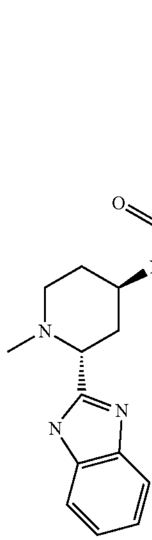 | 104.46 | HPLC Rt = 1.14 MS: [M + H] = 393.4 | 4 |
| 57 | N-[(2R,4R)-2-(5,6-difluoro-1H-benzimidazol-2-yl)-1-methylpiperidin-4-yl]-2,3-dihydro-1,4-benzodioxine-6-carboxamide hydrochloride | 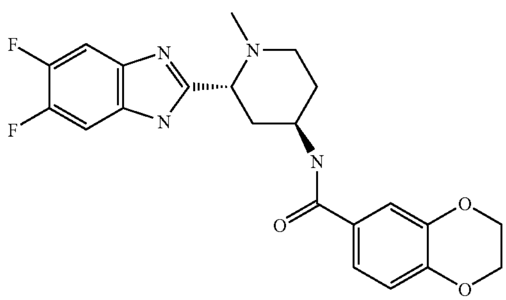 | 104.42 | HPLC Rt = 1.8 MS: [M + H] = 429.4 | 1 |
| 58 | 1-[4-chloro-3-(trifluoromethyl)phenyl]-3-[(3S,5S)-5-(6-fluoro-1H-benzimidazol-2-yl)-1-methylpyrrolidin-3-yl]urea | 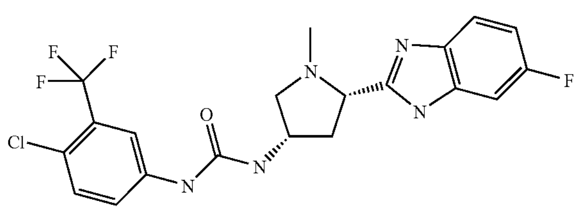 | 104.39 | HPLC Rt = 2.3 MS: [M + H] = 456 | 4 |
| 59 | 1-[(2R,4R)-2-(1H-benzimidazol-2-yl)-1-propylpiperidin-4-yl]-3-(4-cyanophenyl)urea | 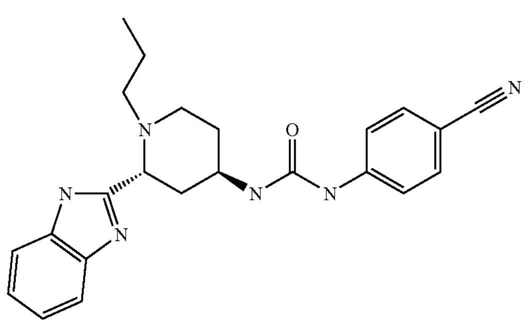 | 104.25 | $^1$H NMR (CD$_3$OD, 400 MHz) δ 0.78 (t, 3H), 1.5 (m, 3H), 1.82 (m, 1H), 2.04 (m, 2H), 2.21 (m, 2H), 2.37 (m, 1H), 2.55 (m, 1H), 3.18 (m, 1H), 3.95 (m, 1H), 7.21 (dd, 2H), 7.49-7.62 (m, 6H); HPLC Rt = 2.5 MS: [M + H] = 403 | 4 |

| EX. # | COMPOUND NAME | STRUCTURE | SMO CELL % INHIBITION @ 2 μM | ANALYTICAL DATA | EX# PREP |
|---|---|---|---|---|---|
| 59 | 1-[(2R,4R)-2-(6-fluoro-1H-benzimidazol-2-yl)-1-methylpiperidin-4-yl]-3-[6-(trifluoromethyl)pyridin-3-yl]urea hydrochloride | 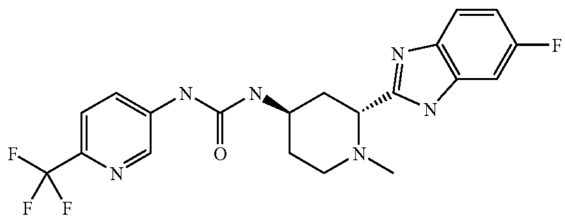 | 104.06 | HPLC Rt = 1.9 MS: [M + H] = 437.2 | 3 |
| 60 | 1-[(2R,4R)-2-(1H-benzimidazol-2-yl)-1-(3-methylbutyl)piperidin-4-yl]-3-(4-cyanophenyl)urea | 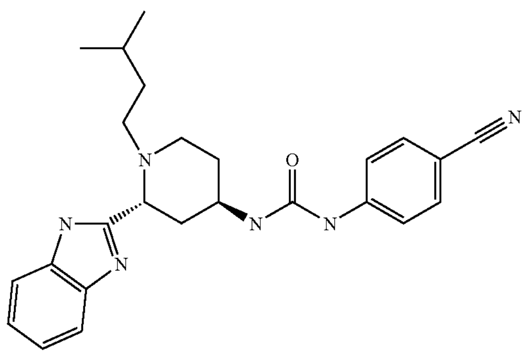 | 104.03 | ¹H NMR (CD₃OD, 400 MHz) δ 0.66 (d, 3H), 0.74 (d, 3H), 1.35 (m, 2H), 1.42 (m, 1H), 1.82 (m, 1H), 2.00 (m, 2H), 2.18 (m, 2H), 2.40 (m, 2H), 3.08 (m, 1H), 3.81 (m, 1H), 4.10 (m, 1H), 7.20 (dd, 2H), 7.50-7.60 (m, 6H), HPLC Rf: 2.6 minutes (method, polar/Elmo); ESI-MS: 431 (M + H), 429 (M − H) HPLC Rt = 2.6 MS: [M + H] = 431 | 4 |
| 61 | 1-[(2R,4R)-2-(1H-benzimidazol-2-yl)-1-benzylpiperidin-4-yl]-3-(4-cyanophenyl)urea | 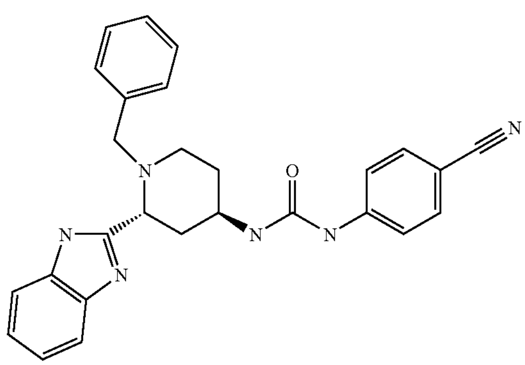 | 99.53 | ¹H NMR (CD₃OD, 400 MHz) δ 1.79 (m, 1H), 1.97 (m, 1H), 2.08 (m, 1H), 2.21 (m, 1H), 2.39 (m, 1H), 2.90 (m, 1H), 3.22 (d, 1H), 3.61 (d, 1H), 3.90 (m, 1H), 4.09 (m, 1H), 4.59 (s, 1H), 7.18-7.29 (m, 5H), 7.32 (dd, 3H), 7.50-7.60 (m, 5H); HPLC Rf: 2.6 minutes method, polar/Elmo); ESI-MS: 451 (M + H), 449 (M − H) HPLC Rt = 2.6 MS: [M + H] = 451 | 4 |
| 62 | 1-[(2R,4R)-2-(5-methoxy-1H-benzimidazol-2-yl)-1-methylpiperidin-4-yl]-3-[6-(trifluoromethyl)pyridin-3-yl]urea hydrochloride | 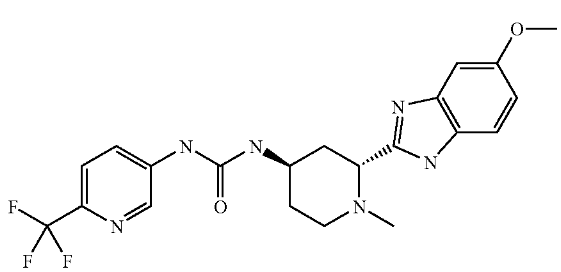 | 103.70 | HPLC Rt = 1.8 MS: [M + H] = 449.2 | 3 |

| EX. # | COMPOUND NAME | STRUCTURE | SMO CELL % INHIBITION @ 2 μM | ANALYTICAL DATA | EX# PREP |
|---|---|---|---|---|---|
| 63 | N-[(2R,4R)-2-(6-cyano-1H-benzimidazol-2-yl)-1-methylpiperidin-4-yl]-2,3-dihydro-1,4-benzodioxine-6-carboxamide hydrochloride | 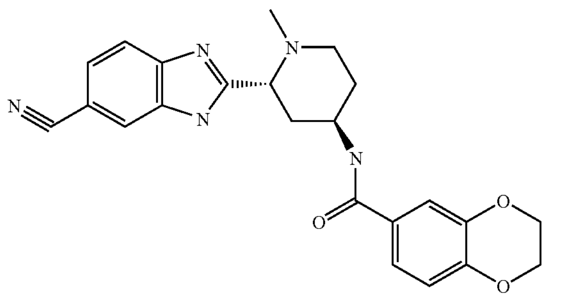 | 103.60 | HPLC Rt = 1.5 MS: [M + H] = 418.4 | 1 |
| 64 | 1-[(2R,4R)-2-(5-chloro-1H-benzimidazol-2-yl)-1-methylpiperidin-4-yl]-3-(4-cyanophenyl)urea hydrochloride | 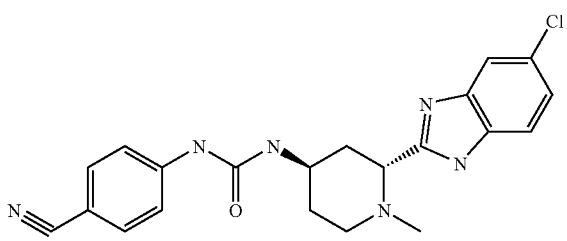 | 102.82 | HPLC Rt = 1.9 MS: [M + H] = 409.2 | 4 |
| 65 | 1-[(2R,4R)-1-methyl-2-(5-methyl-1H-benzimidazol-2-yl)piperidin-4-yl]-3-[6-(trifluoromethyl)pyridin-3-yl]urea hydrochloride | 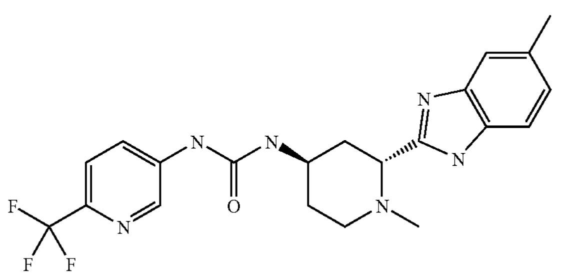 | 102.77 | (CD$_3$COCD$_3$) δ 1.82 (m, 2H), 1.9-2.1 (m, 3H), 2.12 (s, 3H), 2.38 (s, 3H), 2.42 (m, 1H), 2.92 (m, 1H), 3.70 (m, 1H), 4.2 (m, 1H), 6.5 (d, 1H), 7.0 (d, 1H), 7.32 (s, 1H), 7.4 (d, 1H), 7.68 (d, 1H), 8.24 (d, 1H), 8.6 (s, 1H), 8.65 (s, 1H) HPLC Rt = 1.8 MS: [M + H] = 433.2 | 3 |
| 66 | 1-[(2R,4R)-2-(1H-benzimidazol-2-yl)-1-methylpiperidin-4-yl]-3-[6-(trifluoromethyl)pyridin-3-yl]urea hydrochloride | 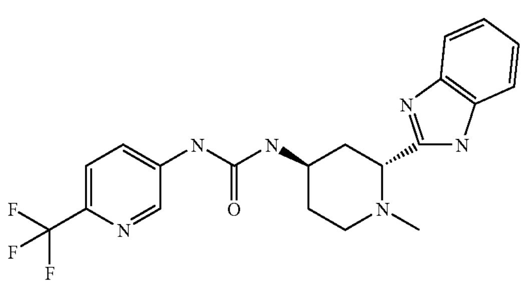 | 102.60 | HPLC Rt = 1.7 MS: [M + H] = 419.2 | 3 |
| 67 | 1-[(2R,4R)-2-(1H-benzimidazol-2-yl)-1-methylpiperidin-4-yl]-3-(2,3-dihydro-1,4-benzodioxin-6-yl)urea hydrochloride | 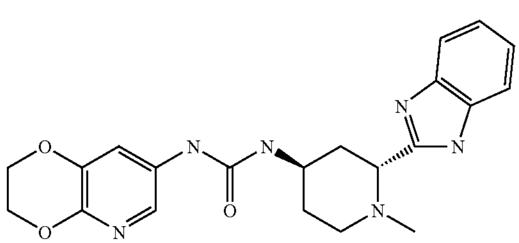 | 102.53 | HPLC Rt = 1.5 MS: [M + H] = 408.2 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 68 | N-[(2R,4R)-2-(1H-benzimidazol-2-yl)-1-methylpiperidin-4-yl]-4-(trifluoroacetyl)benzamide | 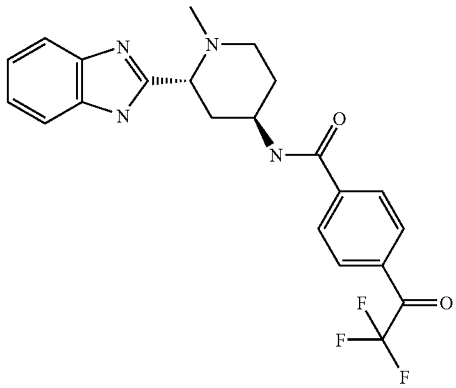 | 102.13 | HPLC Rt = 1.6 MS: [M + H] = 429.3 | 1 |
| 69 | 1-[(2R,4R)-2-(1H-benzimidazol-2-yl)-1-methylpiperidin-4-yl]-3-(5-methylpyridin-3-yl)urea hydrochloride | 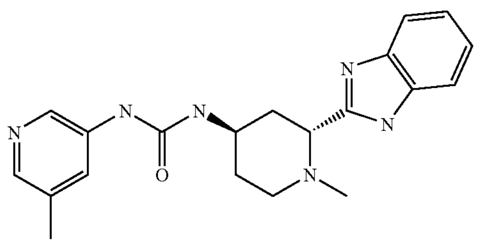 | 101.73 | HPLC Rt = 1.7 MS: [M + H] = 365.3 | 3 |
| 70 | 1-[(2R,4R)-2-(1H-benzimidazol-2-yl)-1-cyclobutylpiperidin-4-yl]-3-(4-cyanophenyl)urea | 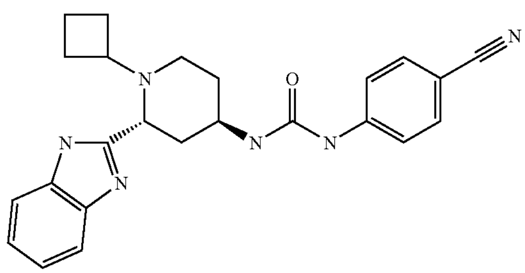 | 101.35 | $^1$H NMR (CD$_3$OD, 400 MHz) δ 1.38 (m, 2H), 1.49 (m, 2H), 1.60 (m, 1H), 1.79 (m, 1H), 1.90 (m, 3H), 2.23 (m, 1H), 2.49 (m, 1H), 3.02 (m, 2H), 3.90 (m, 1H), 4.10 (m, 1H), 7.20 (dd, 2H), 7.50-7.60 (m, 6H); HPLC Rf: 2.7 minutes (method, polar/Elmo); ESI-MS: 415 (M + H), 413 (M − H) HPLC Rt = 2.7 MS: [M + H] = 415 | 4 |
| 71 | 1-[(2R,4R)-2-(1H-benzimidazol-2-yl)-1-methylpiperidin-4-yl]-3-(5,6-dimethylpyridin-3-yl)yrea hydrochloride | 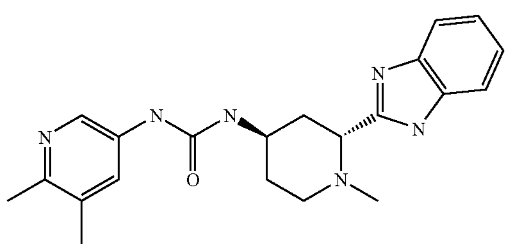 | 101.22 | HPLC Rt = 1.5 MS: [M + H] = 379.3 | 3 |

| EX. # | COMPOUND NAME | STRUCTURE | SMO CELL % INHIBITION @ 2 μM | ANALYTICAL DATA | EX# PREP |
|---|---|---|---|---|---|
| 72 | 4-azido-N-[(2R,4R)-2-(1H-benzimidazol-2-yl)-1-methylpiperidin-4-yl]benzamide | 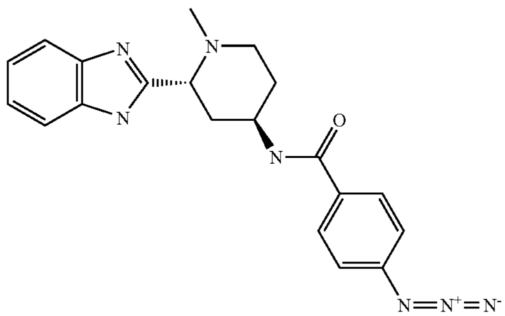 | 101.16 | HPLC Rt = 1.4 MS: [M + H] = 376.2 | 1 |
| 73 | 1-[(2R,4R)-2-(6-chloro-1H-benzimidazol-2-yl)-1-methylpiperidin-4-yl]-3-[6-(trifluoromethyl)pyridin-3-yl]urea hydrochloride | 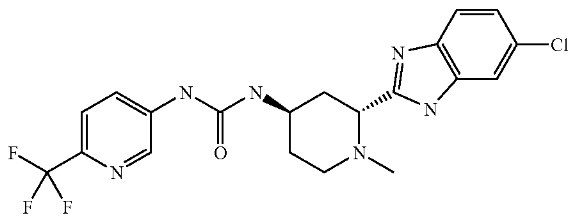 | 101.10 | HPLC Rt = 2.0 MS: [M + H] = 453.1 | 3 |
| 74 | N-[(2R,4R)-2-(1H-benzimidazol-2-yl)-1-methylpiperidin-4-yl]-3-pyridin-4-yl-1H-pyrazole-5-carboxamide hydrochloride | 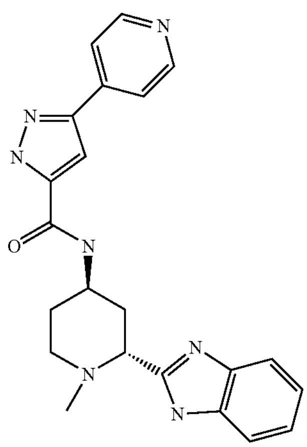 | 100.93 | HPLC Rt = 0.8 MS: [M + H] = 400.3 | 1 |
| 75 | 1-[(2R,4R)-2-(1H-benzimidazol-2-yl)-1-methylpiperidin-4-yl]-3-phenylurea hydrochloride | 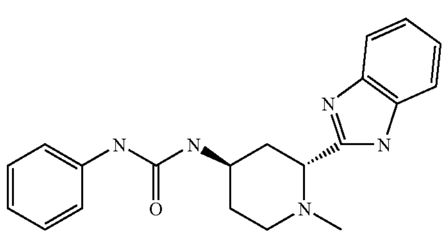 | 100.46 | HPLC Rt = 1.6 MS: [M + H] = 350.3 | 4 |
| 76 | 1-[(2R,4R)-2-(1H-benzimidazol-2-yl)-1-methylpiperidin-4-yl]-3-benzylurea hydrochloride | 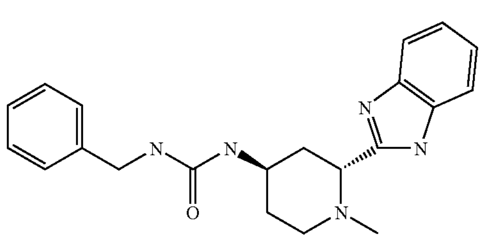 | 100.18 | HPLC Rt = 2.0 MS: [M + H] = 364.3 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 77 | 1-[(2R,4R)-2-(5,6-dimethyl-1H-benzimidazol-2-yl)-1-methylpiperidin-4-yl]-3-[6-(trifluoromethyl)pyridin-3-yl]urea hydrochloride | 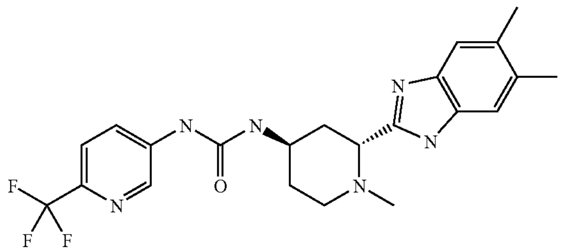 | 99.95 | HPLC Rt = 1.9 MS: [M + H] = 447.2 | 3 |
| 78 | N-[(2R,4R)-2-(1H-benzimidazol-2-yl)-1-methylpiperidin-4-yl]-2-(5-chloro-2-thienyl)acetamide hydrochloride | 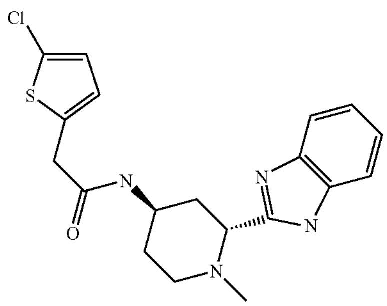 | 99.29 | HPLC Rt = 1.63 MS: [M + H] = 389.2 | 1 |
| 79 | N-{(2R,4R)-1-methyl-2-[6-(trifluoromethyl)-1H-benzimidazol-2-yl]piperidin-4-yl}-2,3-dihydro-1,4-benzodioxine-6-carboxamide hydrochloride | 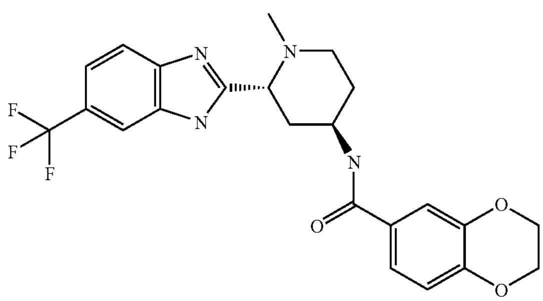 | 99.17 | (CD$_3$OD) δ 1.97 (m, 2H), 2.18 (m, 2H), 2.24 (s, 3H), 2.5 (m, 1H), 2.96 (m, 1H), 3.78 (m, 1H), 4.24 (m, 4H), 4.38 (m, 1H), 6.24 (d, 1H), 6.85 (d, 1H), 7.24 (m, 2H), 7.3 (s, 1H), 7.45 (s, 1H), 7.4 (b, 1H) HPLC Rt = 2.0 MS: [M + H] = 461.1 | 1 |
| 80 | 1-[(2R,4R)-2-(1H-benzimidazol-2-yl)-1-methylpiperidin-4-yl]-3-pyridin-3-ylurea hydrochloride | 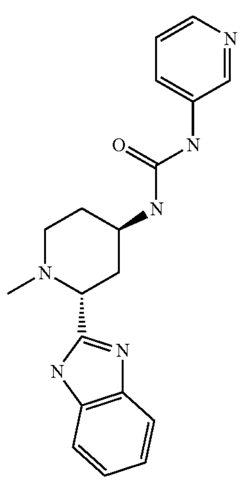 | 98.03 | HPLC Rt = 1.3 MS: [M + H] = 351.3 | 4 |

-continued

| EX. # | COMPOUND NAME | STRUCTURE | SMO CELL % INHIBITION @ 2 μM | ANALYTICAL DATA | EX# PREP |
|---|---|---|---|---|---|
| 81 | 1-[(2R,4R)-2-(1H-benzimidazol-2-yl)-1-methylpiperidin-4-yl]-3-(6-methylpyridin-3-yl)urea hydrochloride | 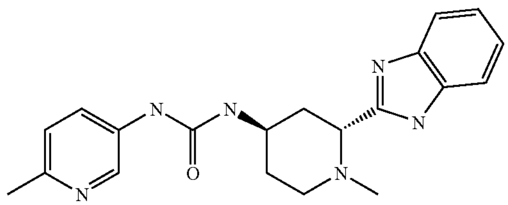 | 97.75 | HPLC Rt = 1.5 MS: [M + H] = 365.3 | 3 |
| 82 | N-[(2R,4R)-2-(1H-benzimidazol-2-yl)-1-cyclobutylpiperidin-4-yl]-2,3-dihydro-1,4-benzodioxine-6-carboxamide hydrochloride | 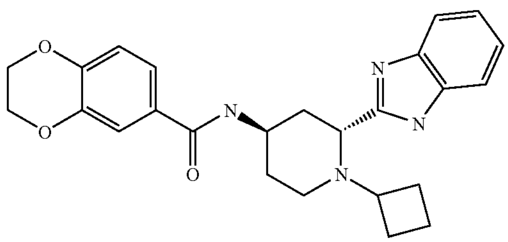 | 96.77 | HPLC Rt = 1.5 MS: [M + H] = 433.1 | 1 |
| 83 | 1-[(2R,4R)-2-(1H-benzimidazol-2-yl)-1-methylpiperidin-4-yl]-3-(6-methoxypyridin-3-yl)urea hydrochloride | 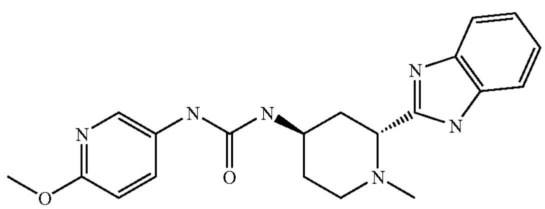 | 96.06 | HPLC Rt = 2.0 MS: [M + H] = 381.2 | 3 |
| 84 | 1-[(3R,5S)-5-(1H-benzimidazol-2-yl)-1-isopropylpyrrolidin-3-yl]-3-[4-chloro-3-(trifluoromethyl)phenyl]urea | 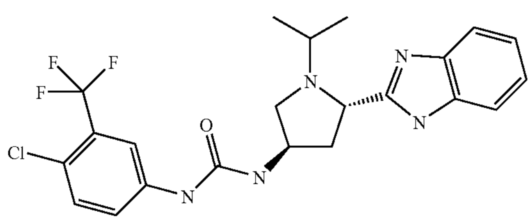 | 95.36 | HPLC Rt = 2.3 MS: [M + H] = 466 | 4 |
| 85 | 1-[(2R,4R)-2-(1H-benzimidazol-2-yl)-1-methylpiperidin-4-yl]-3-cyclopentylurea hydrochloride | 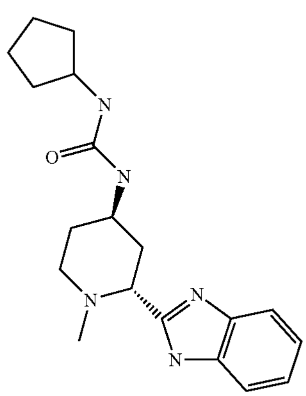 | 93.08 | HPLC Rt = 0.7 MS: [M + H] = 342.2 | 4 |

| EX. # | COMPOUND NAME | STRUCTURE | SMO CELL % INHIBITION @ 2 μM | ANALYTICAL DATA | EX# PREP |
|---|---|---|---|---|---|
| 86 | N-[(2R,4R)-2-(1H-benzimidazol-2-yl)-1-methylpiperidin-4-yl]-2,3-dihydro-1,4-benzodioxine-6-carboxamide hydrochloride | 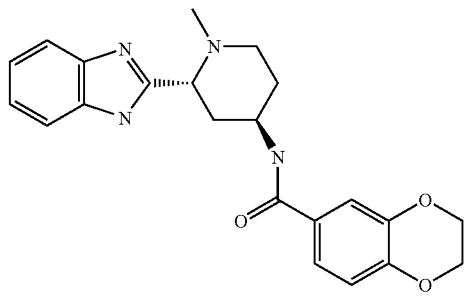 | 93.07 | HPLC Rt = 1.4 MS: [M + H] = 393 | 1 |
| 87 | N-[(2R,4R)-2-(1H-benzimidazol-2-yl)-1-methylpiperidin-4-yl]-2-oxo-1,2,3,4-tetrahydroquinoline-6-carboxamide hydrochloride | 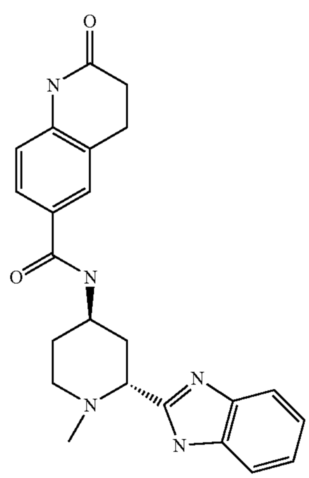 | 92.32 | HPLC Rt = 1.1 MS: [M + H] = 404.3 | 1 |
| 88 | 1-[(2R,4R)-2-(1H-benzimidazol-2-yl)-1-methylpiperidin-4-yl]-3-(3-cyanophenyl)urea hydrochloride | 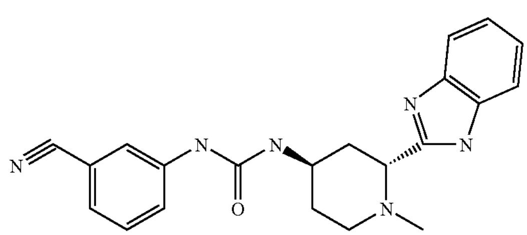 | 92.14 | HPLC Rt = 1.4 MS: [M + H] = 375.2 | 4 |
| 89 | N-[(2R,4R)-2-(1H-benzimidazol-2-yl)-1-(cyclopropylmethyl)piperidin-4-yl]-2,3-dihydro-1,4-benzodioxine-6-carboxamide hydrochloride | 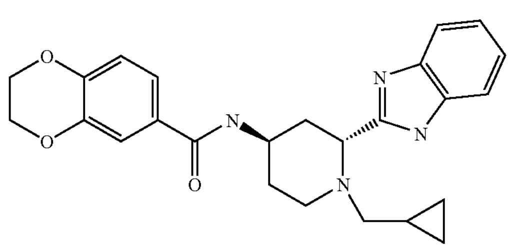 | 88.20 | HPLC Rt = 1.4 MS: [M + H] = 433 | 1 |

| EX. # | COMPOUND NAME | STRUCTURE | SMO CELL % INHIBITION @ 2 µM | ANALYTICAL DATA | EX# PREP |
|---|---|---|---|---|---|
| 90 | 1-[(2R,4R)-2-(1H-benzimidazol-2-yl)-1-methylpiperidin-4-yl]-3-(5-phenyl-2-thienyl)urea hydrochloride | 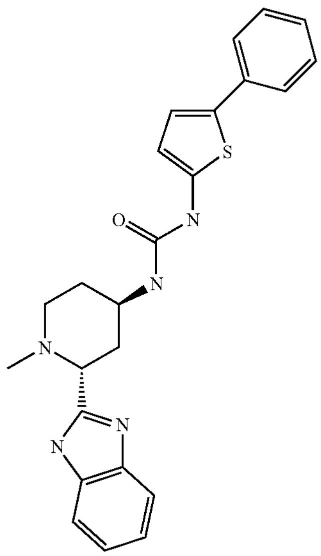 | 87.90 | HPLC Rt = 2.7 MS: [M + H] = 432.1 | 4 |
| 91 | N-[(2r,4r)-2-(1H-benzimidazol-2-yl)-1-methylpiperidin-4-yl]-2-methyl-6-(trifluoromethyl)nicotinamide hydrochloride | 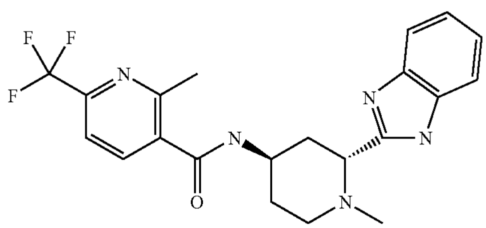 | 87.90 | HPLC Rt = 1.4 MS: [M + H] = 418.1 | 1 |
| 92 | N-[(2R,4R)-2-(1H-benzimidazol-2-yl)-1-methylpiperidin-4-yl]-4-(1,3-oxazol-5-yl)benzamide hydrochloride | 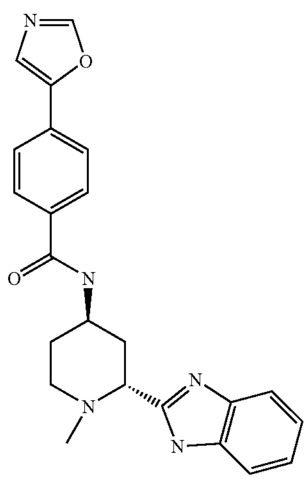 | 86.40 | HPLC Rt = 1.3 MS: [M + H] = 402.3 | 1 |
| 93 | 1-[(3S,5S)-5-(1H-benzimidazol-2-yl)-1-isopropylpyrrolidin-3-yl]-3-[4-chloro-3-(trifluoromethyl)phenyl]urea | 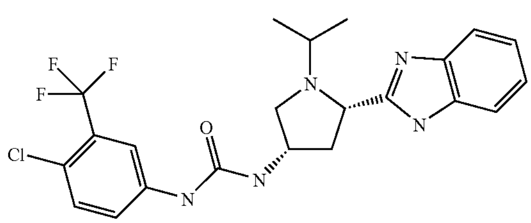 | 85.20 | HPLC Rt = 2.3 MS: [M + H] = 466 | 4 |

| EX. # | COMPOUND NAME | STRUCTURE | SMO CELL % INHIBITION @ 2 μM | ANALYTICAL DATA | EX# PREP |
|---|---|---|---|---|---|
| 94 | N-[(2R,4S)-2-(1H-benzimidazol-2-yl)-1-methylpiperidin-4-yl]-2,3-dihydro-1,4-benzodioxine-6-carboxamide hydrochloride | 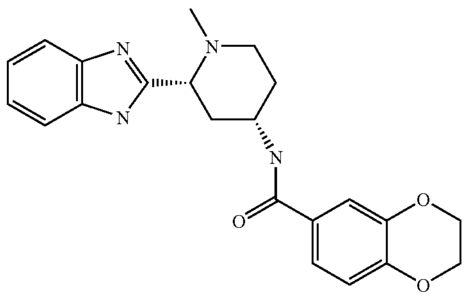 | 79.70 | HPLC Rt = 1.6 MS: [M + H] = 393.1 | 1 |
| 95 | N-[(2R,4R)-2-(1H-benzimidazol-2-yl)-1-methylpiperidin-4-yl]morpholine-4-carboxamide hydrochloride | 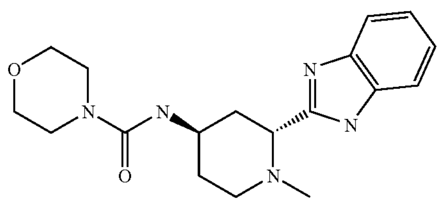 | 78.70 | HPLC Rt = 1.6 MS: [M + H] = 344.3 | 3 |
| 96 | 1-[(2R,4R)-2-(1H-benzimidazol-2-yl)-1-methylpiperidin-4-yl]-3-(5-methoxypyridin-3-yl)urea hydrochloride | 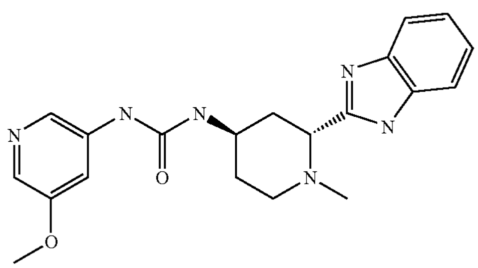 | 76.30 | HPLC Rt = 2.4 MS: [M + H] = 381.2 | 3 |
| 97 | N-[(2R,4R)-2-(1H-benzimidazol-2-yl)-1-methylpiperidin-4-yl]-2,3-dihydro[1,4]dioxino[2,3-b]pyridine-7-carboxamide hydrochloride | 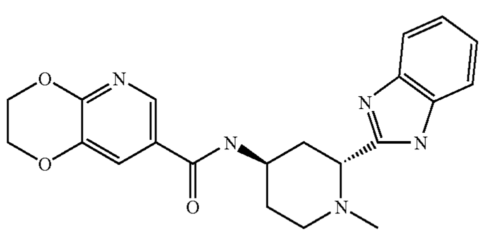 | 75.40 | HPLC Rt = 1.1 MS: [M + H] = 394.3 | 1 |
| 98 | 1-[(2R,4R)-2-(1H-benzimidazol-2-yl)-1-(2-phenylethyl)piperidin-4-yl]-3-(4-cyanophenyl)urea | 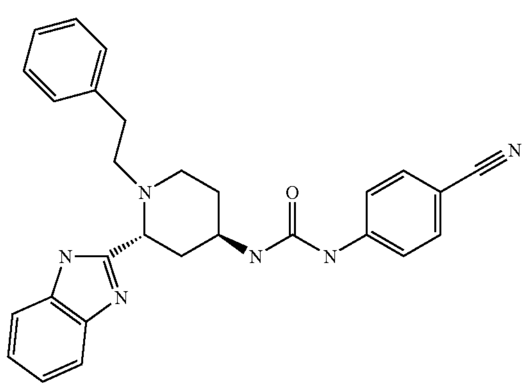 | 74.50 | $^1$H NMR (CD$_3$OD, 400 MHz) δ 1.83-1.87 (m, 1H), 1.99-2.13 (m, 3H), 2.42-2.46 (m, 1H), 2.58-2.70 (m, 3H), 2.78-2.82 (m, 1H), 3.14-3.18 (m, 2H), 3.91-3.94 (m, 1H), 4.08-4.10 (m, 1H), 6.95 (d, 2H), 7.15-7.10 (m, 3H), 7.21 (dd, 2H), 7.49-7.59 (m, 6H); HPLC Rt = 2.8 MS: [M + H] = 465 | 4 |

| EX. # | COMPOUND NAME | STRUCTURE | SMO CELL % INHIBITION @ 2 μM | ANALYTICAL DATA | EX# PREP |
|---|---|---|---|---|---|
| 99 | N-[(2R,4R)-2-(1H-benzimidazol-2-yl)piperidin-4-yl]-2,3-dihydro-1,4-benzodioxine-6-carboxamide trifluoroacetate | 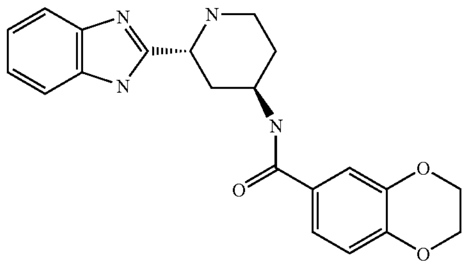 | 72.00 | HPLC Rt = 1.3 MS: [M + H] = 379 | 1 |
| 100 | N-[(2R,4R)-2-(1H-benzimidazol-2-yl)-1-methylpiperidin-4-yl]-3-oxo-3,4-dihydro-2H-1,4-benzoxazine-6-carboxamide hydrochloride | 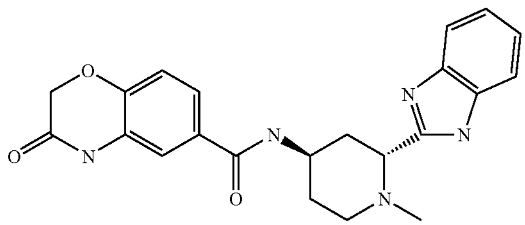 | 63.70 | HPLC Rt = 1.3 MS: [M + H] = 406 | 1 |
| 101 | 1-[(2R,4R)-2-(1H-benzimidazol-2-yl)-1-methylpiperidin-4-yl]-3-[5-(trifluoromethyl)pyridin-2-yl]urea hydrochloride | 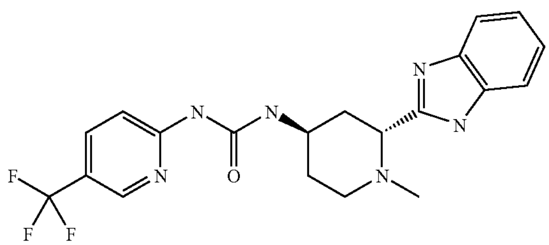 | 62.50 | HPLC Rt = 1.8 MS: [M + H] = 419.2 | 3 |
| 102 | N-[(2R,4R)-2-(1H-benzimidazol-2-yl)-1-methylpiperidin-4-yl]-4-fluoro-3-methoxybenzamide trifluoroacetate | 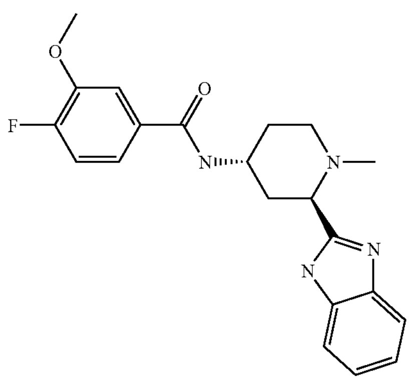 | 102.0 | HPLC Rt = 1.09 MS: [M + H] = 383.23 | 1 |
| 103 | N-[(2R,4R)-2-(1H-benzimidazol-2-yl)-1-methylpiperidin-4-yl]-6-methylquinoline-4-carboxamide trifluoroacetate | 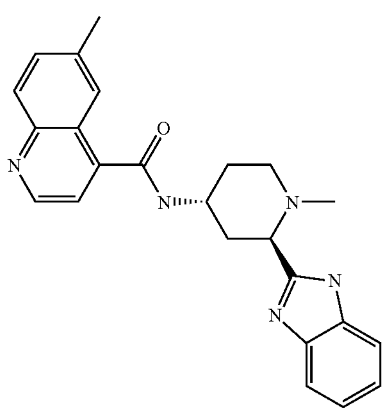 | 100.0 | HPLC Rt = 0.92 MS: [M + H] = 400.27 | 1 |

-continued

| EX. # | COMPOUND NAME | STRUCTURE | SMO CELL % INHIBITION @ 2 μM | ANALYTICAL DATA | EX# PREP |
|---|---|---|---|---|---|
| 104 | N-[(2R,4R)-2-(1H-benzimidazol-2-yl)-1-methylpiperidin-4-yl]-2-(1-benzofuran-2-yl)acetamide trifluoroacetate | 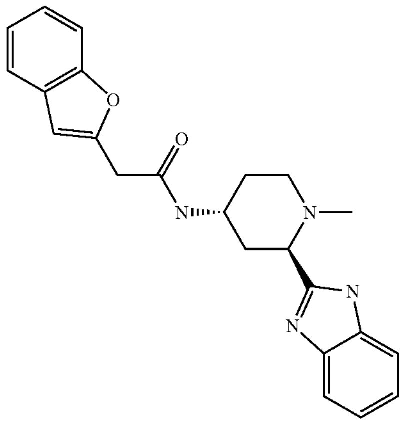 | 99.5 | HPLC Rt = 1.16 MS: [M + H] = 389.24 | 1 |
| 105 | (2S)-N-[(2R,4R)-2-(1H-benzimidazol-2-yl)-1-methylpiperidin-4-yl]-2,3-dihydro-1,4-benzodioxine-2-carboxamide trifluoroacetate | 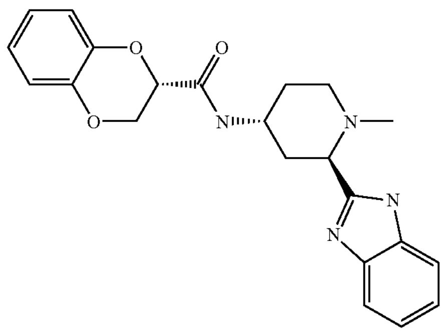 | 97.8 | HPLC Rt = 1.13 MS: [M + H] = 393.23 | 1 |
| 106 | N-[(2R,4R)-2-(1H-benzimidazol-2-yl)-1-methylpiperidin-4-yl]-2-(2H-1,2,3-benzotriazol-2-yl)acetamide trifluoroacetate | 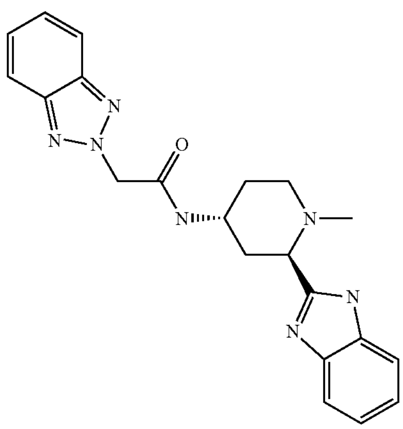 | 94.5 | HPLC Rt = 1.05 MS: [M + H] = 390.25 | 1 |
| 107 | N-[(2R,4R)-2-(1H-benzimidazol-2-yl)-1-methylpiperidin-4-yl]-2-(methylthio)benzamide trifluoroacetate | 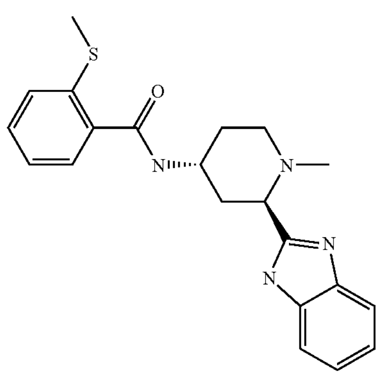 | 88.3 | HPLC Rt = 1.06 MS: [M + H] = 381.21 | 1 |

-continued

| EX. # | COMPOUND NAME | STRUCTURE | SMO CELL % INHIBITION @ 2 μM | ANALYTICAL DATA | EX# PREP |
|---|---|---|---|---|---|
| 108 | N-[(2R,4R)-2-(1H-benzimidazol-2-yl)-1-methylpiperidin-4-yl]-2-(2H-indazol-2-yl)acetamide trifluoroacetate | 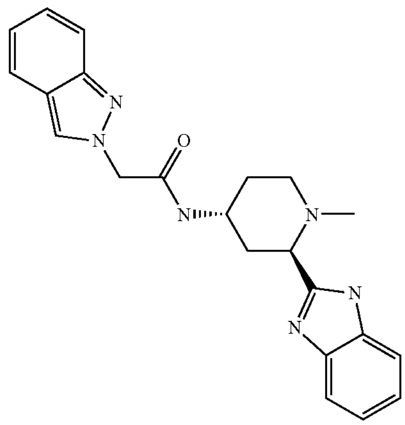 | 86.4 | HPLC Rt = 1.08 MS: [M + H] = 389.26 | 1 |
| 109 | N-[(2R,4R)-2-(1H-benzimidazol-2-yl)-1-methylpiperidin-4-yl]-2-(1H-indazol-1-yl)acetamide trifluoroacetate | 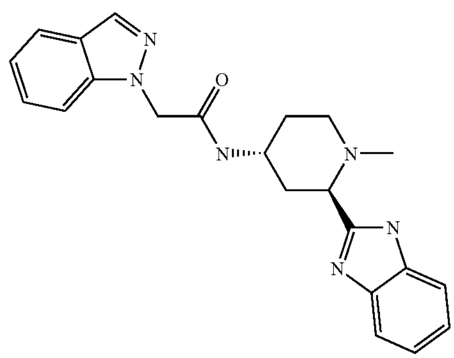 | 85.2 | HPLC Rt = 1.07 MS: [M + H] = 389.25 | 1 |
| 110 | N-[(2R,4R)-2-(1H-benzimidazol-2-yl)-1-methylpiperidin-4-yl]-2-phenylacetamide trifluoroacetate | 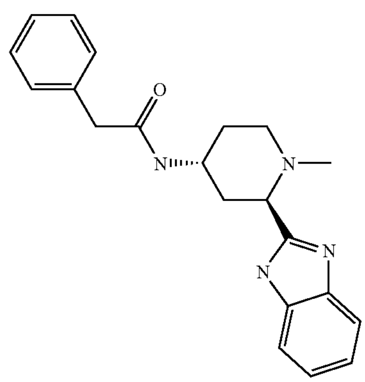 | 83.2 | HPLC Rt = 1.07 MS: [M + H] = 349.23 | 1 |
| 111 | N-[(2R,4R)-2-(1H-benzimidazol-2-yl)-1-methylpiperidin-4-yl]-4-methoxybenzamide trifluoroacetate | 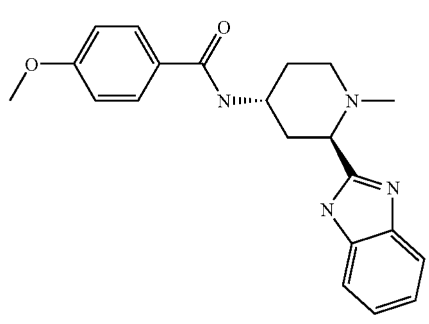 | 83.2 | HPLC Rt = 1.02 MS: [M + H] = 365.24 | 1 |

-continued

| EX. # | COMPOUND NAME | STRUCTURE | SMO CELL % INHIBITION @ 2 μM | ANALYTICAL DATA | EX# PREP |
|---|---|---|---|---|---|
| 112 | N-[(2R,4R)-2-(1H-benzimidazol-2-yl)-1-methylpiperidin-4-yl]-3-methoxybenzamide trifluoroacetate | 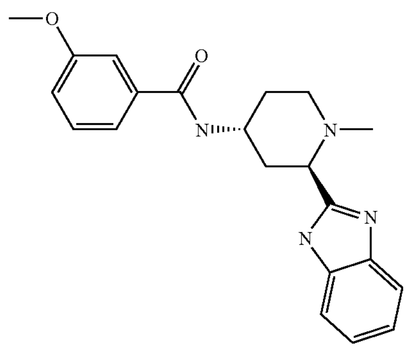 | 81.7 | HPLC Rt = 1.04 MS: [M + H] = 365.23 | 1 |
| 113 | N-[(2R,4R)-2-(1H-benzimidazol-2-yl)-1-methylpiperidin-4-yl]-1-methyl-1H-indole-2-carboxamide trifluoroacetate | 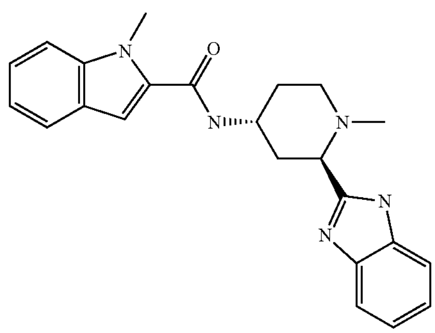 | 76.1 | HPLC Rt = 1.27 MS: [M + H] = 388.26 | 1 |
| 114 | N-[(2R,4R)-2-(1H-benzimidazol-2-yl)-1-methylpiperidin-4-yl]-2-(1,3-benzoxazol-2-yl)acetamide trifluoroacetate | 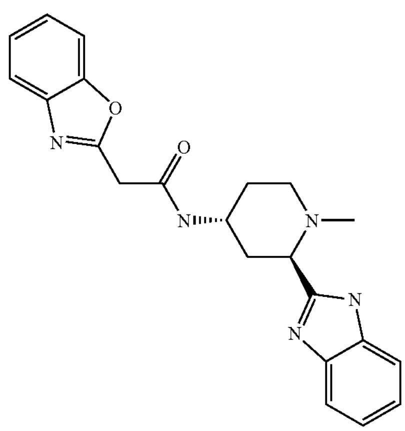 | 75.5 | HPLC Rt = 0.94 MS: [M + H] = 408.27 | 1 |
| 115 | N-[(2R,4R)-2-(1H-benzimidazol-2-yl)-1-methylpiperidin-4-yl]pyrazolo[1,5-a]pyridine-3-carboxamide trifluoroacetate | 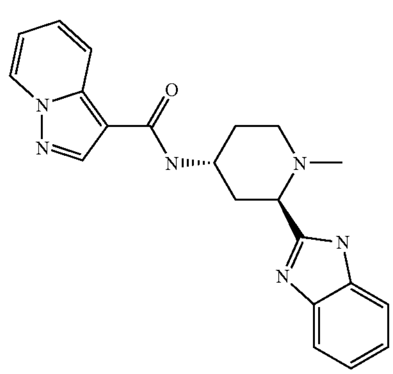 | 69.6 | HPLC Rt = 0.91 MS: [M + H] = 375.25 | 1 |

| EX. # | COMPOUND NAME | STRUCTURE | SMO CELL % INHIBITION @ 2 μM | ANALYTICAL DATA | EX# PREP |
|---|---|---|---|---|---|
| 116 | N-[(2R,4R)-2-(1H-benzimidazol-2-yl)-1-methylpiperidin-4-yl]-2-(2,3-dihydro-1-benzofuran-5-yl)acetamide trifluoroacetate | 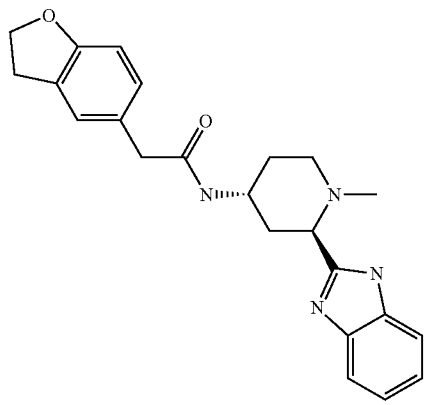 | 68.2 | HPLC Rt = 1.06 MS: [M + H] = 391.27 | 1 |
| 117 | N-[(2R,4R)-2-(1H-benzimidazol-2-yl)-1-methylpiperidin-4-yl]-3-fluoro-4-methoxybenzamide trifluoroacetate | 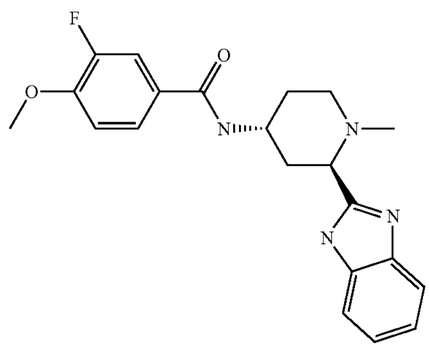 | 65.4 | HPLC Rt = 1.12 MS: [M + H] = 383.22 | 1 |
| 118 | N-[(2R,4R)-2-(1H-benzimidazol-2-yl)-1-methylpiperidin-4-yl]-7-methylpyrazolo[1,5-a]pyridine-2-carboxamide trifluoroacetate | 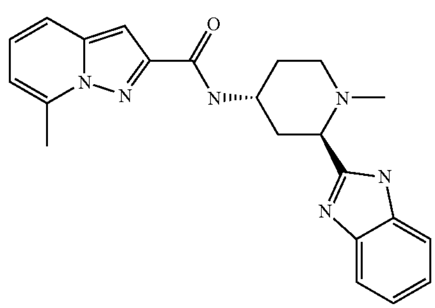 | 65.1 | HPLC Rt = 1.1 MS: [M + H] = 389.25 | 1 |
| 119 | N-[(2R,4R)-2-(1H-benzimidazol-2-yl)-1-methylpiperidin-4-yl]-2,1,3-benzoxadiazole-5-carboxamide trifluoroacetate | 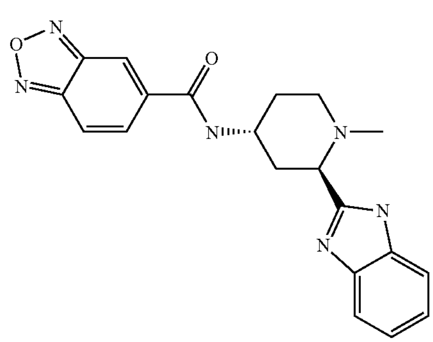 | 64.5 | HPLC Rt = 1.11 MS: [M + H] = 377.21 | 1 |

-continued

| EX. # | COMPOUND NAME | STRUCTURE | SMO CELL % INHIBITION @ 2 μM | ANALYTICAL DATA | EX# PREP |
|---|---|---|---|---|---|
| 120 | N-[(2R,4R)-2-(1H-benzimidazol-2-yl)-1-methylpiperidin-4-yl]-2-(2-fluorophenyl)acetamide trifluoroacetate | 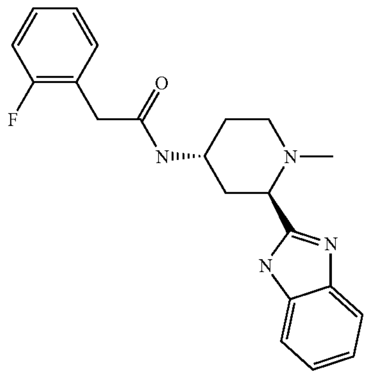 | 63.7 | HPLC Rt = 1.07 MS: [M + H] = 367.22 | 1 |
| 121 | N-[(2R,4R)-2-(1H-benzimidazol-2-yl)-1-methylpiperidin-4-yl]-4-cyanobenzamide trifluoroacetate | 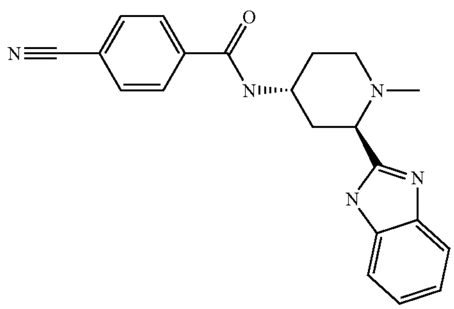 | 62.3 | HPLC Rt = 0.99 MS: [M + H] = 360.23 | 1 |
| 122 | N-[(2R,4R)-2-(1H-benzimidazol-2-yl)-1-methylpiperidin-4-yl]-2,2-difluoro-2-phenylacetamide trifluoroacetate | 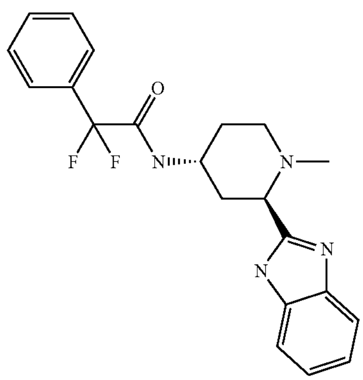 | 57.5 | HPLC Rt = 1.22 MS: [M + H] = 385.24 | 1 |
| 123 | N-[(2R,4R)-2-(1H-benzimidazol-2-yl)-1-methylpiperidin-4-yl]-2-(3-fluorophenyl)acetamide trifluoroacetate | 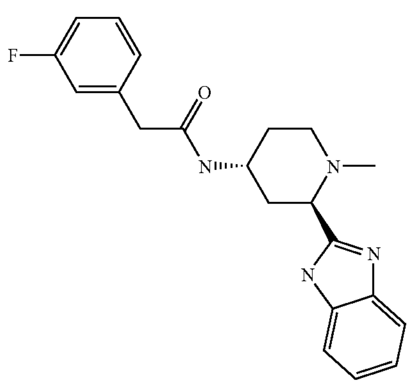 | 52.2 | HPLC Rt = 1.08 MS: [M + H] = 367.22 | 1 |

-continued

| EX. # | COMPOUND NAME | STRUCTURE | SMO CELL % INHIBITION @ 2 μM | ANALYTICAL DATA | EX# PREP |
|---|---|---|---|---|---|
| 124 | N-[(2R,4R)-2-(1H-benzimidazol-2-yl)-1-methylpiperidin-4-yl]-1-tert-butyl-3-methyl-1H-pyrazole-5-carboxamide trifluoroacetate | 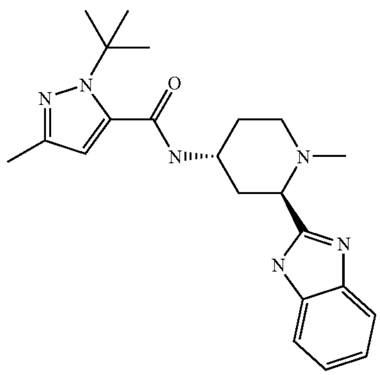 | 50.6 | HPLC Rt = 1.08 MS: [M + H] = 395.3 | 1 |
| 125 | N-[(2R,4R)-2-(1H-benzimidazol-2-yl)-1-cyclopropylpiperidin-4-yl]-2,3-dihydro-1,4-benzodioxine-6-carboxamide hydrochloride | 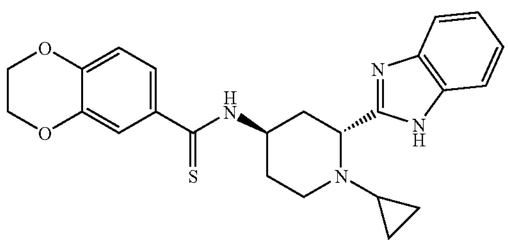 | 102.06 | (acetone-D6)' 0.3-0.5 (m, 4H), 1.8 (m, 2H), 2.16 (m, 2H), 2.48 (m, 1H), 2.88 (m, 1H), 3.14 (m, 1H), 4.28 (m, 4H), 4.4 (m, 1H), 4.5 (m, 1H), 6.8 (d, 1H), 7.1 (m, 2H), 7.4 (m, 2H), 7.42 (m, 1H), 7.53 (m, 1H) HPLC Rt = 1.7 MS: [M + H] = 419.2 | 2 |
| 126 | 1-[(2R,4R)-2-(6-chloro-1H-benzimidazol-2-yl)-1-methylpiperidin-4-yl]-3-(6-methylpyridin-3-yl)urea hydrochloride | 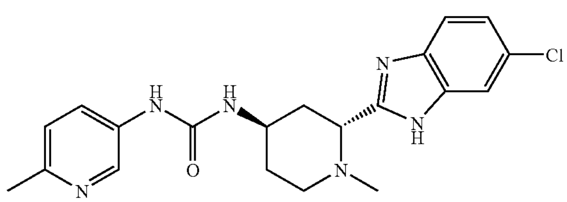 | 110.0 | HPLC Rt = 1.8 MS: [M + H] = 399.2 | 3 |
| 127 | 1-[(2R,4R)-2-(5-cyano-1H-benzimidazol-2-yl)-1-methylpiperidin-4-yl]-3-(6-methylpyridin-3-yl)urea hydrochloride | 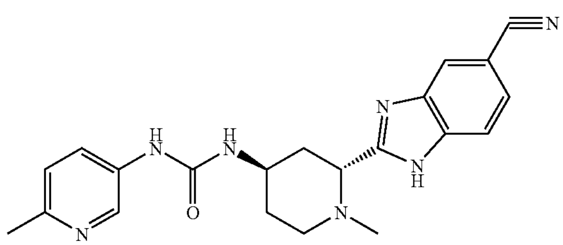 | 103.0 | HPLC Rt = 1.5 MS: [M + H] = 390.2 | 3 |
| 128 | 1-(6-methylpyridin-3-yl)-3-{(2R,4R)-1-methyl-2-[5-(trifluoromethyl)-1H-benzimidazol-2-yl]piperidin-4-yl}urea hydrochloride | 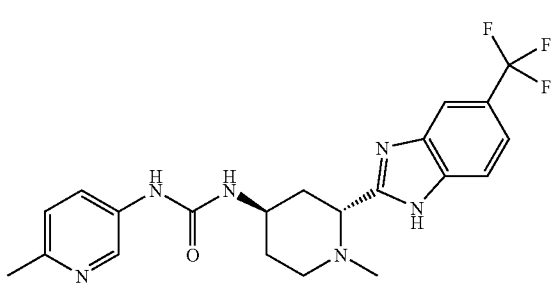 | 102.34 | (acetone-D6)' 1.8 (m, 1H), 2.04 (m, 1H), 2.18 (m, 2H), 2.22 (s, 3H), 2.40 (s, 3H), 2.62 (m, 1H), 3.0 (m, 1H), 3.94 (m, 1H), 4.18 (m, 1H), 6.4 (d, !H), 7.05 (d, 1H), 7.45 (d, 1H), 7.7 (d, 1H), 7.9 (m, 2H), 8.08 (s, 1H), 8.42 (s, 1H) HPLC Rt = 1.1 MS: [M + H] = 433.2 | 3 |

-continued

| EX. # | COMPOUND NAME | STRUCTURE | SMO CELL % INHIBITION @ 2 μM | ANALYTICAL DATA | EX# PREP |
|---|---|---|---|---|---|
| 129 | 1-[(2R,4R)-2-(5-methoxy-1H-benzimidazol-2-yl)-1-methylpiperidin-4-yl]-3-(6-methylpyridin-3-yl)urea hydrochloride | 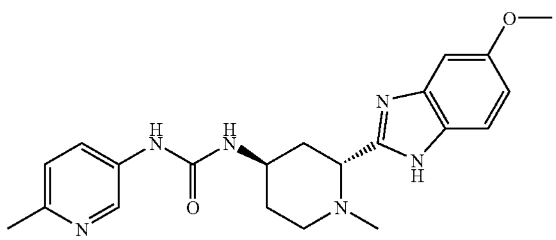 | 103.83 | HPLC Rt = 0.08 MS: [M + H] = 395.2 | 3 |
| 130 | 1-[(2R,4R)-1-methyl-2-(5-methyl-1H-benzimidazol-2-yl)piperidin-4-yl]-3-(6-methylpyridin-3-yl)urea hydrochloride | 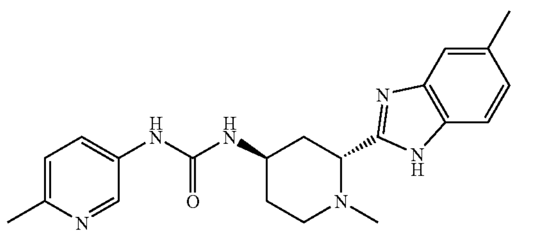 | 106.1 | HPLC Rt = 0.9 MS: [M + H] = 379.2 | 3 |
| 131 | 1-[(2R,4R)-2-(5,6-dimethyl-1H-benzimidazol-2-yl)-1-methylpiperidin-4-yl]-3-(6-methylpyridin-3-yl)urea hydrochloride | 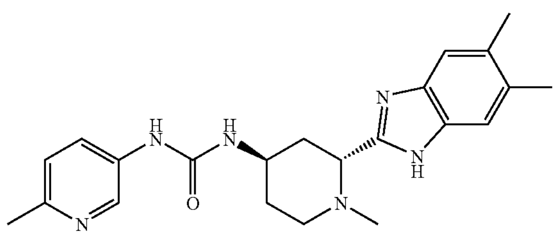 | 104.86 | HPLC Rt = 1.00 MS: [M + H] = 393.3 | 3 |
| 132 | 1-[(2R,4R)-2-(6-fluoro-1H-benzimidazol-2-yl)-1-methylpiperidin-4-yl]-3-(6-methylpyridin-3-yl)urea hydrochloride | 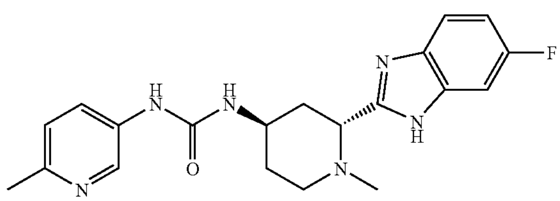 | 107.75 | HPLC Rt = 0.4 MS: [M + H] = 383.2 | 3 |
| 133 | 1-[(2R,4R)-2-(6-chloro-1H-benzimidazol-2-yl)-1-methylpiperidin-4-yl]-3-(6-methoxypyridin-3-yl)urea hydrochloride | 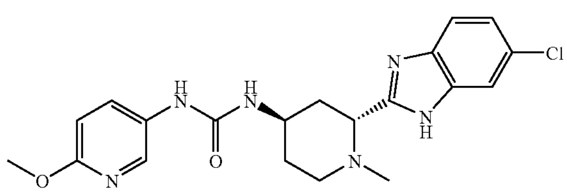 | 107.55 | HPLC Rt = 1.6 MS: [M + H] = 415 | 3 |
| 134 | 1-[(2R,4R)-2-(5-cyano-1H-benzimidazol-2-yl)-1-methylpiperidin-4-yl]-3-(6-methoxypyridin-3-yl)urea hydrochloride | 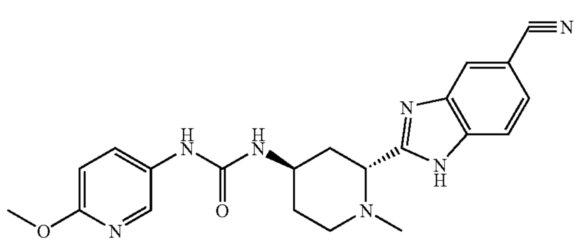 | 104.78 | HPLC Rt = 1.2 MS: [M + H] = 406.2 | 3 |

| EX. # | COMPOUND NAME | STRUCTURE | SMO CELL % INHIBITION @ 2 μM | ANALYTICAL DATA | EX# PREP |
|---|---|---|---|---|---|
| 135 | 1-(6-methoxypyridin-3-yl)-3-{(2R,4R)-1-methyl-2-[5-(trifluoromethyl)-1H-benzimidazol-2-yl]piperidin-4-yl}urea hydrochloride | 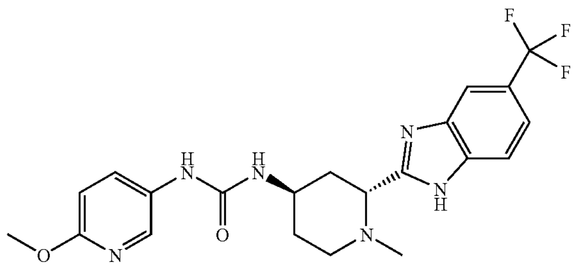 | 103.51 | HPLC Rt = 1.7 MS: [M + H] = 449.2 | 3 |
| 136 | 1-[(2R,4R)-2-(5-methoxy-1H-benzimidazol-2-yl)-1-methylpiperidin-4-yl]-3-(6-methoxypyridin-3-yl)urea hydrochloride | 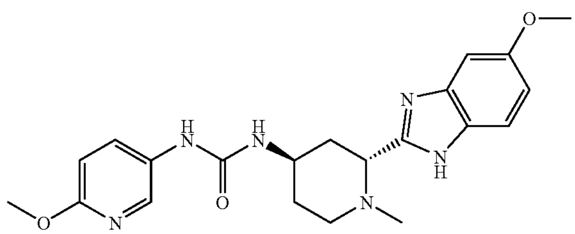 | 105.82 | HPLC Rt = 1.4 MS: [M + H] = 411.1 | 3 |
| 137 | 1-(6-methoxypyridin-3-yl)-3-[(2R,4R)-1-methyl-2-(5-methyl-1H-benzimidazol-2-yl)piperidin-4-yl]urea hydrochloride | 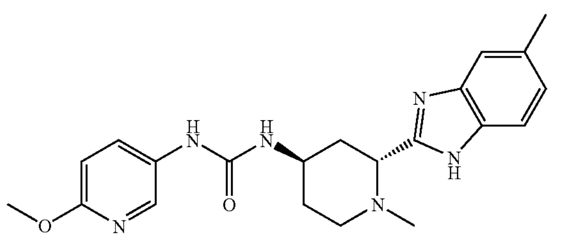 | 102.48 | (acetone-D6)' 1.8 (m, 1H), 1.9 (m, 1H), 2.08 (m, 2H), 2.38 (s, 3H), 2.42 (m, 1H), 2.84 (m, 1H), 3.68 (m, 1H), 3.8 (s, 3H), 4.18 (m, 1H), 6.22 (d, !H), 6.6 (d, 1H), 7.0 (d, 1H), 7.37 (s, 1H), 7.94 (m 1H), 7.8 (dd, 1H), 8.0 (s, 1H), 8.1 (s, 1H) HPLC Rt = 1.4 MS: [M + H] = 395.1 | 3 |
| 138 | 1-[(2R,4R)-2-(5,6-dimethyl-1H-benzimidazol-2-yl)-1-methylpiperidin-4-yl]-3-(6-methoxypyridin-3-yl)urea hydrochloride | 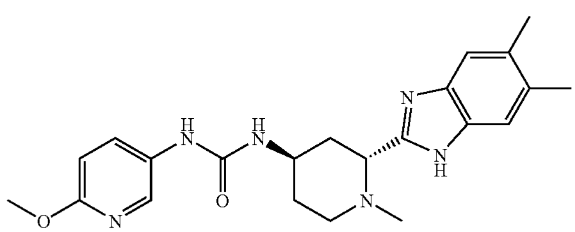 | 107.67 | HPLC Rt = 1.5 MS: [M + H] = 409.2 | 3 |
| 139 | 1-[(2R,4R)-2-(6-fluoro-1H-benzimidazol-2-yl)-1-methylpiperidin-4-yl]-3-(6-methoxypyridin-3-yl)urea hydrochloride | 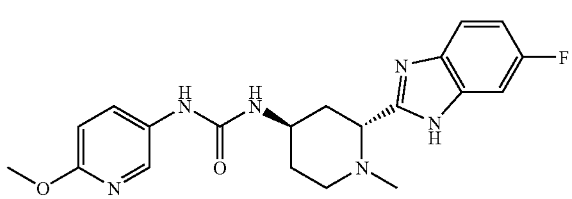 | 106.32 | (acetone-D6)' 1.8 (m, 1H), 1.85-2.0 (m, 2H), 2.05 (m, 1H), 2.1 (s, 3H), 2.42 (m, 1H), 2.82 (m, 1H), 3.64 (m, 1H), 3.8 (s, 3H), 4.18 (m, 1H), 6.17 (d, 1H), 6.6 (d, 1H), 7.0 (m, 1H), 7.2 (d, 1H), 7.5 (b, 1H), 7.82 (m, 2H), 8.2 (s, 1H) HPLC Rt = 1.2 MS: [M + H] = 399.2 | 3 |

-continued

| EX. # | COMPOUND NAME | STRUCTURE | SMO CELL % INHIBITION @ 2 μM | ANALYTICAL DATA | EX# PREP |
|---|---|---|---|---|---|
| 140 | N-[(2R,4R)-2-(1H-benzimidazol-2-yl)-1-methylpiperidin-4-yl]-2,3-dihydro-1,4-benzodioxine-6-carbothioamide hydrochloride | 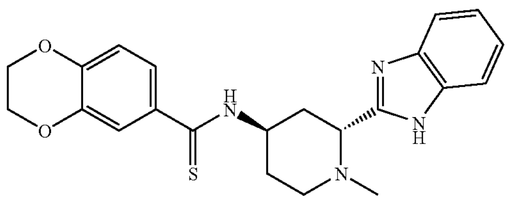 | 106.94 | HPLC Rt = 1.7 MS: [M + H] = 409.1 | 1 |
| 141 | N-[(2R,4R)-2-(1H-benzimidazol-2-yl)-1-methylpiperidin-4-yl]-5-fluoro-2,3-dihydro-1,4-benzodioxine-6-carboxamide trifluoroacetate | 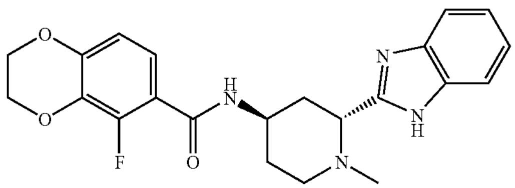 | 85.3 | HPLC Rt = 1.3 MS: [M + H] = 411.3 | 1 |
| 142 | N-[(2R,4R)-2-(5-chloro-1H-benzimidazol-2-yl)-1-methylpiperidin-4-yl]-5-fluoro-2,3-dihydro-1,4-benzodioxine-6-carboxamide triflouroacetate | 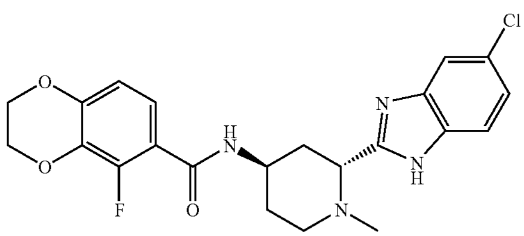 | 100.91 | HPLC Rt = 1.7 MS: [M + H] = 445.1 | 1 |
| 143 | 5-fluoro-N-[(2R,4R)-2-(5-methoxy-1H-benzimidazol-2-yl)-1-methylpiperidin-4-yl]-2,3-dihydro-1,4-benzodioxine-6-carboxamide triflouroacetate | 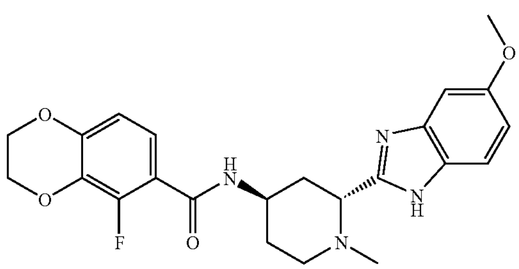 | 83.5 | HPLC Rt = 1.3 MS: [M + H] = 441.1 | 1 |
| 144 | N-[(2R,4R)-2-(1H-benzimidazol-2-yl)-1-methylpiperidin-4-yl]-5-chloro-2,3-dihydro-1,4-benzodioxine-6-carboxamide triflouroacetate | 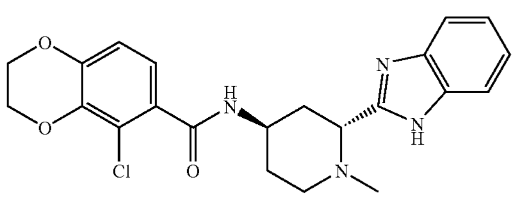 | 107.73 | HPLC Rt = 1.2 MS: [M + H] = 427.1 | 1 |
| 145 | 5-chloro-N-[(2R,4R)-2-(5-chloro-1H-benzimidazol-2-yl)-1-methylpiperidin-4-yl]-2,3-dihydro-1,4-benzodioxine-6-carboxamide triflouroacetate | 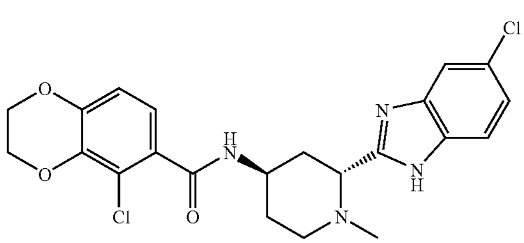 | 106.34 | HPLC Rt = 1.5 MS: [M + H] = 461 | 1 |

-continued

| EX. # | COMPOUND NAME | STRUCTURE | SMO CELL % INHIBITION @ 2 μM | ANALYTICAL DATA | EX# PREP |
|---|---|---|---|---|---|
| 146 | 5-chloro-N-[(2R,4R)-2-(5-methoxy-1H-benzimidazol-2-yl)-1-methylpiperidin-4-yl]-2,3-dihydro-1,4-benzodioxine-6-carboxamide triflouroacetate | 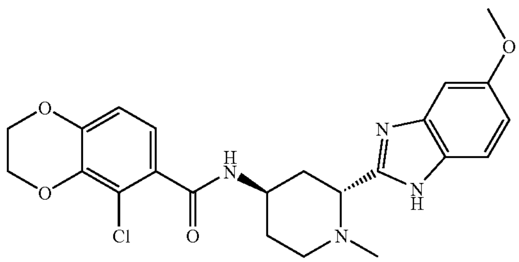 | 106.53 | HPLC Rt = 1.1 MS: [M + H] = 457.1 | 1 |
| 147 | N-[(2R,4R)-2-(1H-benzimidazol-2-yl)-1-methylpiperidin-4-yl]-7-chloro-2,3-dihydro-1,4-benzodioxine-6-carboxamide triflouroacetate | 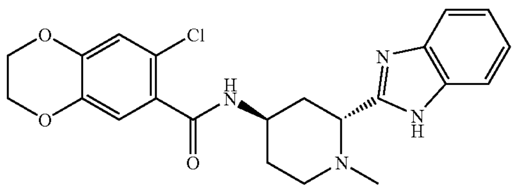 | 69.5 | HPLC Rt = 1.3 MS: [M + H] = 427.1 | |
| 148 | 7-chloro-N-[(2R,4R)-2-(5-chloro-1H-benzimidazol-2-yl)-1-methylpiperidin-4-yl]-2,3-dihydro-1,4-benzodioxine-6-carboxamide triflouroacetate | 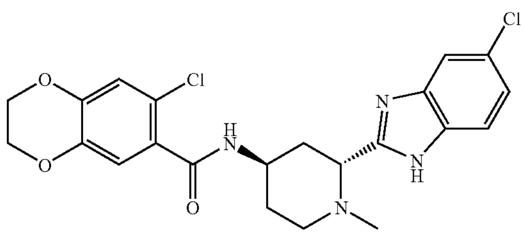 | 94.97 | HPLC Rt = 1.6 MS: [M + H] = 461 | 1 |
| 149 | 7-chloro-N-[(2R,4R)-2-(5-methoxy-1H-benzimidazol-2-yl)-1-methylpiperidin-4-yl]-2,3-dihydro-1,4-benzodioxine-6-carboxamide triflouroacetate | 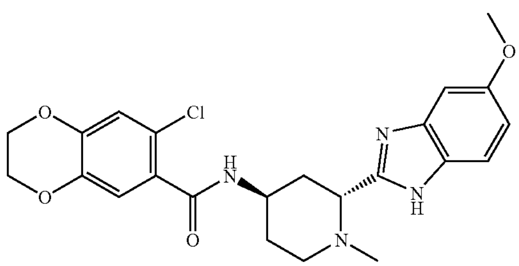 | 35.3 | HPLC Rt = 1.4 MS: [M + H] = 457.1 | 1 |
| 150 | 1-[(2R,4R)-2-(1H-benzimidazol-2-yl)-1-cyclobutylpiperidin-4-yl]-3-(6-methylpyridin-3-yl)urea triflouroacetate | 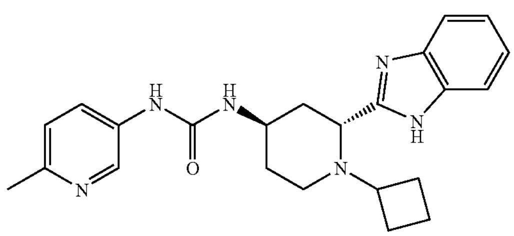 | 106.11 | HPLC Rt = 0.9 MS: [M + H] = 405.2 | 3 |
| 151 | 1-[(2R,4R)-1-cyclobutyl-2-(5-methyl-1H-benzimidazol-2-yl)piperidin-4-yl]-3-(6-methylpyridin-3-yl)urea triflouroacetate | 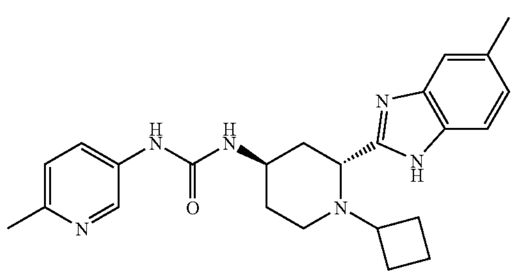 | 106.65 | HPLC Rt = 1.1 MS: [M + H] = 419.2 | 3 |

-continued

| EX. # | COMPOUND NAME | STRUCTURE | SMO CELL % INHIBITION @ 2 µM | ANALYTICAL DATA | EX# PREP |
|---|---|---|---|---|---|
| 152 | 1-[(2R,4R)-1-cyclobutyl-2-(5,6-dimethyl-1H-benzimidazol-2-yl)piperidin-4-yl]-3-(6-methylpyridin-3-yl)urea triflouroacetate | 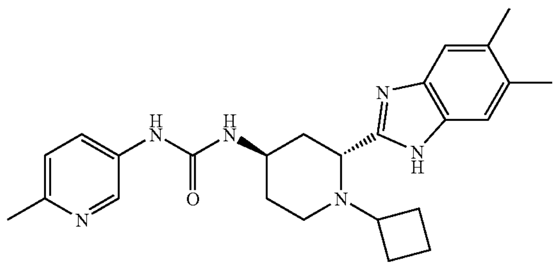 | 106.17 | HPLC Rt = 2.0 MS: [M + H] = 433.2 | 3 |
| 153 | 1-[(2R,4R)-1-cyclobutyl-2-(5-methoxy-1H-benzimidazol-2-yl)piperidin-4-yl]-3-(6-methylpyridin-3-yl)urea triflouroacetate | 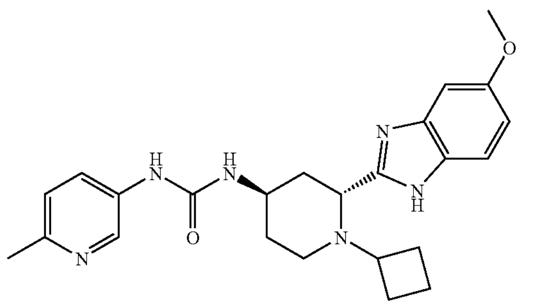 | 106.60 | HPLC Rt = 1.1 MS: [M + H] = 435.2 | 3 |

We claim:

1. A compound of Formula II(a),

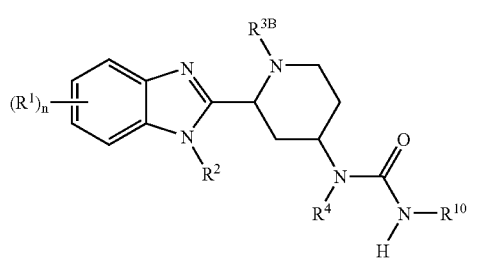

wherein:
each $R^1$ is independently halo, $(C_1-C_6)$alkyl, $(C_1-C_6)$alkoxy, —$CF_3$, —CN, or —$NR^{16}R^{17}$;
$R^2$ is hydrogen or $(C_1-C_6)$alkyl;
$R^{3B}$ is hydrogen, $(C_1-C_6)$alkyl, —$(CH_2)_t(C_6-C_{12})$aryl, or —$(CH_2)_t(C_3-C_{12})$carbocyclyl;
$R^4$ is hydrogen or $(C_1-C_6)$alkyl;
$R^{10}$ is —$(CH_2)_t(C_6-C_{12})$aryl or —$(CH_2)_t(4$ to 14 membered heterocyclyl), wherein each of said $(C_6-C_{12})$aryl and (4 to 14 membered heterocyclyl) is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —C(O)$(C_1-C_6$ alkyl), —C(O)$CF_3$, azido, (4 to 12 membered heterocyclyl), and —S(($C_1-C_6$)alkyl);
each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

2. A compound according to claim 1, wherein:
each $R^1$ is independently F, Cl, Br, —$CH_3$, —$OCH_3$, —$CF_3$, —CN, or —$NR^{16}R^{17}$;
$R^2$ is hydrogen;
$R^{3B}$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$CH_2$(phenyl);
$R^4$ is hydrogen; and
$R^{10}$ is phenyl, pyridyl, or 2,3-dihydro-1,4-benzodioxinyl, wherein each of said phenyl, pyridyl, and 2,3-dihydro-1,4-benzodioxinyl is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —C(O)$(C_1-C_6$ alkyl), —C(O)$CF_3$, azido, (4 to 12 membered heterocyclyl), and —S(($C_1-C_6$)alkyl); or
a pharmaceutically acceptable salt thereof.

3. A compound according to claim 2, wherein:
each $R^1$ is independently F, Cl, —$CH_3$, —$OCH_3$, —$CF_3$, —CN, or —$N(CH_3)_2$;
$R^{3B}$ is —$CH_3$; and
$R^{10}$ is phenyl, 2-pyridyl, 3-pyridyl, 4-pyridyl, or 2,3-dihydro-1,4-benzodioxin-6-yl, wherein each of said phenyl, 2-pyridyl, 3-pyridyl, 4-pyridyl, and 2,3-dihydro-1,4-benzodioxin-6-yl is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$alkoxy, —$NO_2$, —$(CH_2)_t(C_6-C_{12})$aryl, —C(O)$(C_1-C_6$ alkyl), —C(O)$CF_3$, azido, (4 to 12 membered heterocyclyl), and —S(($C_1-C_6$)alkyl); or
a pharmaceutically acceptable salt thereof.

4. A compound according to claim 3, wherein $R^{10}$ is phenyl, 3-pyridyl, or 2,3-dihydro-1,4-benzodioxin-6-yl, wherein each of said phenyl, 3-pyridyl, and 2,3-dihydro-1,4-benzodioxin-6-yl is optionally substituted with from 1 to 5 substituents each of which is independently selected from $(C_1-C_6)$alkyl, —CN, halo, —$CF_3$, —$OCF_3$, —$NR^{16}R^{17}$, $(C_1-C_6)$ alkoxy, —NO₂, —(CH₂)ₜ(C₆-C₁₂)aryl, —C(O)(C₁-C₆ alkyl), —C(O)CF₃, azido, (4 to 12 membered heterocyclyl), and —S((C₁-C₆)alkyl); or a pharmaceutically acceptable salt thereof.

5. A compound according to claim 4, wherein $R^{10}$ is phenyl optionally substituted with from 1 to 5 substituents each of which is independently selected from $(C_1-C_6)$alkyl, —CN, halo, —CF₃, —OCF₃, —NR¹⁶R¹⁷, $(C_1-C_6)$alkoxy, —NO₂, —(CH₂)ₜ(C₆-C₁₂)aryl, —C(O)(C₁-C₆ alkyl), —C(O)CF₃, azido, (4 to 12 membered heterocyclyl), and —S((C₁-C₆)alkyl); or a pharmaceutically acceptable salt thereof.

6. A compound according to claim 5, wherein $R^{10}$ is phenyl optionally substituted with from 1 to 5 substituents each of which is independently selected from —CH₃, —CN, —F, —Cl, —Br, —CF₃, —OCF₃, —NR¹⁶R¹⁷, —OCH₃, and —NO₂; or a pharmaceutically acceptable salt thereof.

7. A compound of Formula III(a),

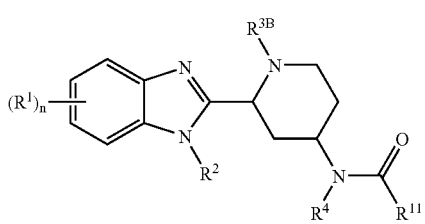

III(a)

wherein:
each $R^1$ is independently halo, $(C_1-C_6)$alkyl, $(C_1-C_6)$alkoxy, —CF₃, —CN, or —NR¹⁶R¹⁷;
$R^2$ is hydrogen or $(C_1-C_6)$alkyl;
$R^{3B}$ is hydrogen, $(C_1-C_6)$alkyl, —(CH₂)ₜ(C₆-C₁₂)aryl, or —(CH₂)ₜ(C₃-C₁₂)carbocyclyl;
$R^4$ is hydrogen or $(C_1-C_6)$alkyl;
$R^{11}$ is —(CH₂)ₜ(C₆-C₁₂)aryl or —(CH₂)ₜ(4 to 14 membered heterocyclyl), wherein each of said (C₆-C₁₂)aryl and (4 to 14 membered heterocyclyl) is optionally substituted with from 1 to 5 substituents each of which is independently selected from $(C_1-C_6)$alkyl, —CN, halo, —CF₃, —OCF₃, —NR¹⁶R¹⁷, $(C_1-C_6)$alkoxy, —NO₂, —(CH₂)ₜ(C₆-C₁₂)aryl, —C(O)(C₁-C₆ alkyl), —C(O)CF₃, azido, (4 to 12 membered heterocyclyl), and —S((C₁-C₆)alkyl);
each $R^{16}$ and $R^{17}$ is independently selected from hydrogen and $(C_1-C_6)$alkyl;
n is 0, 1, 2, 3, or 4; and
each t is independently 0, 1, or 2; or
a pharmaceutically acceptable salt thereof.

8. A compound of Formula IV(a)

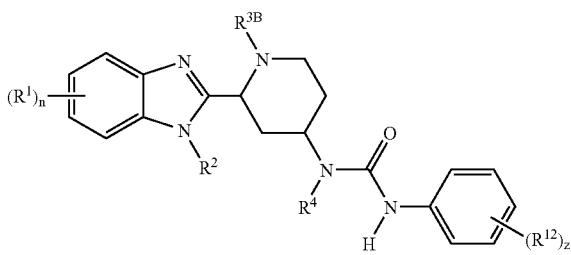

IV(a)

wherein:
each $R^1$ is independently halo, $(C_1-C_6)$alkyl, $(C_1-C_6)$alkoxy, —CF₃, —CN, or —NR¹⁶R¹⁷;
$R^2$ is hydrogen or $(C_1-C_6)$alkyl;
$R^{3B}$ is hydrogen, $(C_1-C_6)$alkyl, —(CH₂)ₜ(C₆-C₁₂)aryl, or —(CH₂)ₜ(C₃-C₁₂)carbocyclyl;
$R^4$ is hydrogen or $(C_1-C_6)$alkyl;
each $R^{12}$ is independently selected from —(CH₂)ₜ(C₆-C₁₂)aryl, —(CH₂)ₜ(4 to 14 membered heterocyclyl), $(C_1-C_6)$alkyl, —CN, halo, —CF₃, —OCF₃, —NR¹⁶R¹⁷, $(C_1-C_6)$alkoxy, —NO₂, —(CH₂)ₜ(C₆-C₁₂)aryl, —C(O)(C₁-C₆ alkyl), —C(O)CF₃, azido, (4 to 12 membered heterocyclyl), and —S((C₁-C₆)alkyl);
each $R^{16}$ and $R^{17}$ is independently selected from hydrogen and $(C_1-C_6)$alkyl;
n is 0, 1, 2, 3, or 4;
each t is independently 0, 1, or 2; and
z is 0, 1, 2, 3, 4, or 5; or
a pharmaceutically acceptable salt thereof.

9. A compound according to claim 8, wherein:
$R^2$ is hydrogen;
$R^{3B}$ is —CH₃;
$R^4$ is hydrogen; and
each $R^{12}$ is independently selected from —CN, —F, —Cl, —Br, —CF₃, —OCF₃, —NR¹⁶R¹⁷, —OCH₃, and —NO₂; or
a pharmaceutically acceptable salt thereof.

10. A compound according to claim 9, wherein:
each $R^1$ is independently halo, —CH₃, —OCH₃, —CF₃, —CN, or —N(CH₃)₂;
$R^{12}$ is —CN, —F, —Cl, —Br, —CF₃, —OCF₃, —OCH₃, or —NO₂; and
z is 1; or
a pharmaceutically acceptable salt thereof.

11. A compound according to claim 10, wherein:
$R^{12}$ is —CN, —F, —Cl, —Br, or —CF₃; and
n is 0; or
a pharmaceutically acceptable salt thereof.

12. A compound according to claim 11, wherein $R^{12}$ is —CN, or a pharmaceutically acceptable salt thereof.

13. A compound selected from:
1-[(2R,4R)-2-(1H-benzimidazol-2-yl)-1-methylpiperidin-4-yl]-3-(4-cyanophenyl)urea;
1-[(2R,4R)-2-(1H-benzimidazol-2-yl)-1-methylpiperidin-4-yl]-3-(4-chlorophenyl)urea;
1-[(2R,4R)-2-(1H-benzimidazol-2-yl)-1-methylpiperidin-4-yl]-3-(6-fluoropyridin-3-yl)urea;
N-[(2R,4R)-2-(1H-benzimidazol-2-yl)-1-methylpiperidin-4-yl]chromane-6-carboxamide;
N-[(2R,4R)-2-(6-chloro-1H-benzimidazol-2-yl)-1-methylpiperidin-4-yl]-2,3-dihydro-1,4-benzodioxine-6-carboxamide;
1-{(2R,4R)-1-methyl-2-[5-(trifluoromethyl)-1H-benzimidazol-2-yl]piperidin-4-yl}-3-[6-(trifluoromethyl)pyridin-3-yl]urea;
1-[(2R,4R)-2-(1H-benzimidazol-2-yl)-1-methylpiperidin-4-yl]-3-(4-methoxyphenyl)urea;
N-[(2R,4R)-2-(6-methoxy-1H-benzimidazol-2-yl)-1-methylpiperidin-4-yl]-2,3-dihydro-1,4-benzodioxine-6-carboxamide;
1-[(2R,4R)-2-(1H-benzimidazol-2-yl)-1-isobutylpiperidin-4-yl]-3-(4-cyanophenyl)urea; and
1-[(2R,4R)-2-(1H-benzimidazol-2-yl)-1-methylpiperidin-4-yl]-3-(6-fluoro-5-methylpyridin-3-yl)urea; or
a pharmaceutically acceptable salt thereof.

14. A compound which is
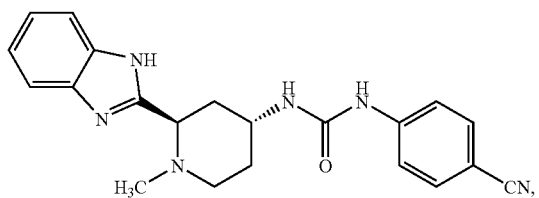
or a pharmaceutically acceptable salt thereof.
15. A compound which is
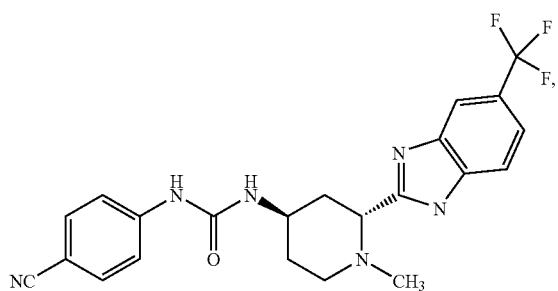
or a pharmaceutically acceptable salt thereof.
16. A compound which is
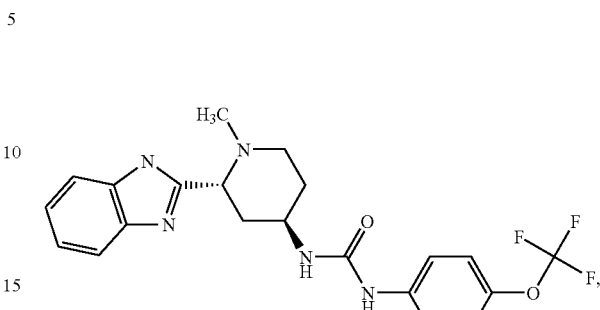
or a pharmaceutically acceptable salt thereof.
17. A pharmaceutical composition, comprising an effective amount of at least one compound according to claim 1, and a pharmaceutically acceptable carrier.
* * * * *